US012004750B2

(12) United States Patent
Connor

(10) Patent No.: US 12,004,750 B2
(45) Date of Patent: Jun. 11, 2024

(54) METHODS FOR CREATING AN EXPANDABLE TWO-PART INTRASACULAR ANEURYSM OCCLUSION DEVICE FROM A TUBULAR MESH

(71) Applicant: Robert A. Connor, St. Paul, MN (US)

(72) Inventor: Robert A. Connor, St. Paul, MN (US)

(73) Assignee: Aneuclose LLC, Ham Lake, MN (US)

( * ) Notice: Subject to any disclaimer, the term of this patent is extended or adjusted under 35 U.S.C. 154(b) by 0 days.

(21) Appl. No.: 18/519,055

(22) Filed: Nov. 26, 2023

(65) Prior Publication Data

US 2024/0090903 A1 Mar. 21, 2024

Related U.S. Application Data

(63) Continuation-in-part of application No. 18/374,602, filed on Sep. 28, 2023, now Pat. No. 11,944,316, which is a continuation-in-part of application No. 18/135,153, filed on Apr. 15, 2023, said application No. 18/519,055 is a continuation-in-part of application No. 18/135,153, filed on Apr. 15, 2023, which is a continuation-in-part of application No. 17/970,510, filed on Oct. 20, 2022, said application No. 18/374,602 is a continuation-in-part of application No. 17/970,510, filed on Oct. 20, 2022, said application No. 18/519,055 is a continuation-in-part of application No. 17/970,510, filed on Oct. 20, 2022, and a continuation-in-part of application No. 17/965,502, filed on Oct. 13, 2022, now abandoned, said application No. 18/374,602 is a continuation-in-part of application No. 17/965,502, filed on Oct. 13, 2022, now abandoned, said application No. 18/135,153 is a continuation-in-part
(Continued)

(51) Int. Cl.
*A61B 17/12* (2006.01)

(52) U.S. Cl.
CPC .. *A61B 17/12172* (2013.01); *A61B 17/12113* (2013.01); *A61B 17/12177* (2013.01); *A61B 2017/1205* (2013.01)

(58) Field of Classification Search
CPC ........ A61B 17/12113; A61B 17/12118; A61B 17/12172; A61B 17/12186; A61B 17/177; A61B 17/12168
See application file for complete search history.

(56) References Cited

U.S. PATENT DOCUMENTS

| 6,454,780 B1 * | 9/2002 | Wallace | A61B 17/12022 606/151 |
| 6,605,102 B1 * | 8/2003 | Mazzocchi | A61B 17/12022 606/200 |

(Continued)

*Primary Examiner* — Darwin P Erezo
*Assistant Examiner* — Christina C Lauer

(57) ABSTRACT

This invention can be embodied in a method and device for therapeutically-occluding a cerebral aneurysm. A method embodiment includes radially-constraining a tubular mesh to form proximal and distal convex portions of the mesh, collapsing the proximal portion into a concave (e.g. bowl) shape, and expanding the distal portion of the mesh within an aneurysm sac by filling it with embolic members and/or material. The expanded distal portion of the mesh holds the concave proximal portion securely against the aneurysm neck and conforms to the wall contours of even an irregularly-shaped aneurysm sac.

2 Claims, 4 Drawing Sheets

Related U.S. Application Data of application No. 17/965,502, filed on Oct. 13, 2022, now abandoned, said application No. 17/970,510 is a continuation-in-part of application No. 17/965,502, filed on Oct. 13, 2022, now abandoned, which is a continuation-in-part of application No. 17/829,313, filed on May 31, 2022, now abandoned, said application No. 18/519,055 is a continuation-in-part of application No. 17/829,313, filed on May 31, 2022, now abandoned, said application No. 17/970,510 is a continuation-in-part of application No. 17/829,313, filed on May 31, 2022, now abandoned, said application No. 18/135,153 is a continuation-in-part of application No. 17/829,313, filed on May 31, 2022, now abandoned, said application No. 18/374,602 is a continuation-in-part of application No. 17/829,313, filed on May 31, 2022, now abandoned, which is a continuation-in-part of application No. 17/485,390, filed on Sep. 25, 2021, now Pat. No. 11,471,164, said application No. 17/970,510 is a continuation-in-part of application No. 17/476,845, filed on Sep. 16, 2021, now Pat. No. 11,583,289, said application No. 17/829,313 is a continuation-in-part of application No. 17/476,845, filed on Sep. 16, 2021, now Pat. No. 11,583,289, said application No. 17/965,502 is a continuation-in-part of application No. 17/476,845, filed on Sep. 16, 2021, now Pat. No. 11,583,289, said application No. 17/829,313 is a continuation-in-part of application No. 17/472,674, filed on Sep. 12, 2021, now abandoned, and a continuation-in-part of application No. 17/467,680, filed on Sep. 7, 2021, now abandoned, and a continuation-in-part of application No. 17/466,497, filed on Sep. 3, 2021, now Pat. No. 11,357,511, and a continuation-in-part of application No. 17/353,652, filed on Jun. 21, 2021, now abandoned, and a continuation-in-part of application No. 17/220,002, filed on Apr. 1, 2021, now Pat. No. 11,464,518, which is a continuation-in-part of application No. 17/214,827, filed on Mar. 27, 2021, now Pat. No. 11,484,322, said application No. 17/829,313 is a continuation-in-part of application No. 17/214,827, filed on Mar. 27, 2021, now Pat. No. 11,484,322, said application No. 17/220,002 is a continuation-in-part of application No. 17/211,446, filed on Mar. 24, 2021, now abandoned, said application No. 17/829,313 is a continuation-in-part of application No. 17/211,446, filed on Mar. 24, 2021, now abandoned, said application No. 17/220,002 is a continuation-in-part of application No. 16/693,267, filed on Nov. 23, 2019, now abandoned, and a continuation-in-part of application No. 16/660,929, filed on Oct. 23, 2019, now Pat. No. 11,471,163, said application No. 16/693,267 is a continuation-in-part of application No. 16/660,929, filed on Oct. 23, 2019, now Pat. No. 11,471,163, and a continuation-in-part of application No. 16/541,241, filed on Aug. 15, 2019, now abandoned, said application No. 16/660,929 is a continuation-in-part of application No. 16/541,241, filed on Aug. 15, 2019, now abandoned, said application No. 16/693,267 is a continuation-in-part of application No. 15/865,822, filed on Jan. 9, 2018, now Pat. No. 10,716,573, said application No. 16/660,929 is a continuation-in-part of application No. 15/865,822, filed on Jan. 9, 2018, now Pat. No. 10,716,573, said application No. 16/541,241 is a continuation-in-part of application No. 15/865,822, filed on Jan. 9, 2018, now Pat. No. 10,716,573, said application No. 16/660,929 is a continuation-in-part of application No. 15/861,482, filed on Jan. 3, 2018, now abandoned, said application No. 16/693,267 is a continuation-in-part of application No. 15/861,482, filed on Jan. 3, 2018, now abandoned, said application No. 15/865,822 is a continuation-in-part of application No. 15/081,909, filed on Mar. 27, 2016, now abandoned, said application No. 15/861,482 is a continuation-in-part of application No. 15/080,915, filed on Mar. 25, 2016, now Pat. No. 10,028,747, which is a continuation-in-part of application No. 14/526,600, filed on Oct. 29, 2014, now abandoned, said application No. 15/865,822 is a continuation-in-part of application No. 14/526,600, filed on Oct. 29, 2014, now abandoned, said application No. 15/081,909 is a continuation-in-part of application No. 14/526,600, filed on Oct. 29, 2014, now abandoned, said application No. 15/861,482 is a continuation-in-part of application No. 14/526,600, filed on Oct. 29, 2014, now abandoned, which is a continuation-in-part of application No. 12/989,048, filed as application No. PCT/US2009/002537 on Apr. 24, 2009, now Pat. No. 8,974,487.

(60) Provisional application No. 63/119,774, filed on Dec. 1, 2020, provisional application No. 62/794,607, filed on Jan. 19, 2019, provisional application No. 62/794,609, filed on Jan. 19, 2019, provisional application No. 62/720,173, filed on Aug. 21, 2018, provisional application No. 62/589,754, filed on Nov. 22, 2017, provisional application No. 62/472,519, filed on Mar. 16, 2017, provisional application No. 62/444,860, filed on Jan. 11, 2017, provisional application No. 61/897,245, filed on Oct. 30, 2013, provisional application No. 61/126,047, filed on May 1, 2008, provisional application No. 61/126,027, filed on May 1, 2008.

(56) References Cited

U.S. PATENT DOCUMENTS

| | | |
|---|---|---|
| 8,597,320 B2 | 12/2013 | Sepetka et al. |
| 8,998,947 B2 | 4/2015 | Aboytes et al. |
| 9,039,726 B2 | 5/2015 | Becking |
| 9,078,658 B2 | 7/2015 | Hewitt et al. |
| 9,492,174 B2 | 11/2016 | Hewitt et al. |
| 9,585,669 B2 | 3/2017 | Becking et al. |
| 9,629,635 B2 | 4/2017 | Hewitt et al. |
| 9,918,720 B2 | 3/2018 | Marchand et al. |
| 9,955,976 B2 | 5/2018 | Hewitt et al. |
| 10,130,372 B2 | 11/2018 | Griffin |
| 10,136,896 B2 | 11/2018 | Hewitt et al. |
| 10,238,393 B2 | 3/2019 | Marchand et al. |
| 10,265,075 B2 | 4/2019 | Porter et al. |
| 10,285,711 B2 | 5/2019 | Griffin |
| 10,314,593 B2 | 6/2019 | Bardsley et al. |
| 10,327,781 B2 | 6/2019 | Divino et al. |
| 10,398,441 B2 | 9/2019 | Warner et al. |
| 10,478,194 B2 | 11/2019 | Rhee et al. |
| 10,610,231 B2 | 4/2020 | Marchand et al. |
| 10,653,425 B1 | 5/2020 | Gorochow et al. |
| 10,716,574 B2 | 7/2020 | Lorenzo et al. |
| 10,729,447 B2 | 8/2020 | Shimizu et al. |
| 10,751,066 B2 | 8/2020 | Lorenzo |
| 10,813,645 B2 | 10/2020 | Hewitt et al. |
| 10,905,430 B2 | 2/2021 | Lorenzo et al. |
| 10,939,914 B2 | 3/2021 | Hewitt et al. |
| 10,939,915 B2 | 3/2021 | Gorochow et al. |

(56) References Cited

U.S. PATENT DOCUMENTS

| | | |
|---|---|---|
| 10,980,545 B2 | 4/2021 | Bowman et al. |
| 11,013,516 B2 | 5/2021 | Franano et al. |
| 11,033,275 B2 | 6/2021 | Franano et al. |
| 11,045,203 B2 | 6/2021 | Sepetka et al. |
| 11,051,825 B2 | 7/2021 | Gorochow |
| 11,058,430 B2 | 7/2021 | Gorochow et al. |
| 11,058,431 B2 | 7/2021 | Pereira et al. |
| 11,071,551 B2 | 7/2021 | Garza et al. |
| 11,076,860 B2 | 8/2021 | Lorenzo |
| 11,076,861 B2 | 8/2021 | Gorochow et al. |
| 11,123,077 B2 | 9/2021 | Lorenzo et al. |
| 11,154,302 B2 | 10/2021 | Lorenzo et al. |
| 11,166,731 B2 | 11/2021 | Wolfe et al. |
| 11,179,159 B2 | 11/2021 | Cox et al. |
| 11,185,335 B2 | 11/2021 | Badruddin et al. |
| 11,202,636 B2 | 12/2021 | Zaidat et al. |
| 11,278,292 B2 | 3/2022 | Gorochow et al. |
| 11,305,387 B2 | 4/2022 | Pulugurtha et al. |
| 11,317,921 B2 | 5/2022 | Hewitt et al. |
| 11,337,706 B2 | 5/2022 | Soto Del Valle et al. |
| 11,389,174 B2 | 7/2022 | Griffin |
| 11,389,309 B2 | 7/2022 | Ruvalcaba et al. |
| 11,413,046 B2 | 8/2022 | Xu et al. |
| 11,426,175 B2 | 8/2022 | Morita et al. |
| 11,457,926 B2 | 10/2022 | Gorochow et al. |
| 11,471,162 B2 | 10/2022 | Griffin |
| 11,497,504 B2 | 11/2022 | Xu et al. |
| 11,498,165 B2 | 11/2022 | Patel et al. |
| 11,517,321 B2 | 12/2022 | Mauger et al. |
| 11,523,831 B2 | 12/2022 | Gorochow et al. |
| 11,559,309 B2 | 1/2023 | Rangwala et al. |
| 11,583,282 B2 | 2/2023 | Gorochow et al. |
| 11,589,872 B2 | 2/2023 | Mauger |
| 11,596,412 B2 | 3/2023 | Xu et al. |
| 11,602,350 B2 | 3/2023 | Gorochow et al. |
| 11,607,226 B2 | 3/2023 | Pedroso et al. |
| 11,890,020 B2 * | 2/2024 | Lorenzo ............ A61B 17/12168 |
| 2002/0169473 A1 | 11/2002 | Sepetka et al. |
| 2006/0064151 A1 * | 3/2006 | Guterman ........ A61B 17/12022 623/1.3 |
| 2006/0155323 A1 | 7/2006 | Porter et al. |
| 2008/0281350 A1 | 11/2008 | Sepetka et al. |
| 2011/0022149 A1 | 1/2011 | Cox et al. |
| 2011/0208227 A1 | 8/2011 | Becking |
| 2012/0165919 A1 | 6/2012 | Cox et al. |
| 2012/0283768 A1 | 11/2012 | Cox et al. |
| 2012/0316598 A1 | 12/2012 | Becking et al. |
| 2013/0245667 A1 | 9/2013 | Marchand et al. |
| 2014/0052233 A1 | 2/2014 | Cox et al. |
| 2014/0135811 A1 | 5/2014 | Divino et al. |
| 2014/0135812 A1 | 5/2014 | Divino et al. |
| 2014/0200607 A1 | 7/2014 | Sepetka et al. |
| 2014/0330299 A1 | 11/2014 | Rosenbluth et al. |
| 2014/0358178 A1 | 12/2014 | Hewitt et al. |
| 2015/0272589 A1 | 10/2015 | Lorenzo |
| 2015/0313605 A1 | 11/2015 | Griffin |
| 2016/0022445 A1 | 1/2016 | Ruvalcaba et al. |
| 2016/0249934 A1 | 9/2016 | Hewitt et al. |
| 2016/0249935 A1 | 9/2016 | Hewitt et al. |
| 2016/0249937 A1 | 9/2016 | Marchand et al. |
| 2016/0367260 A9 | 12/2016 | Hewitt et al. |
| 2017/0079661 A1 | 3/2017 | Bardsley et al. |
| 2017/0079662 A1 | 3/2017 | Rhee et al. |
| 2017/0095254 A1 | 4/2017 | Hewitt et al. |
| 2017/0128077 A1 | 5/2017 | Hewitt et al. |
| 2017/0156734 A1 | 6/2017 | Griffin |
| 2017/0224350 A1 | 8/2017 | Shimizu et al. |
| 2017/0258473 A1 | 9/2017 | Plaza et al. |
| 2017/0281194 A1 | 10/2017 | Divino et al. |
| 2018/0000489 A1 | 1/2018 | Marchand et al. |
| 2018/0070955 A1 | 3/2018 | Greene et al. |
| 2018/0206849 A1 | 7/2018 | Hewitt et al. |
| 2018/0242979 A1 | 8/2018 | Lorenzo |
| 2018/0303486 A1 | 10/2018 | Rosenbluth et al. |
| 2019/0008522 A1 | 1/2019 | Lorenzo |
| 2019/0053811 A1 | 2/2019 | Garza et al. |
| 2019/0059909 A1 | 2/2019 | Griffin |
| 2019/0192166 A1 | 6/2019 | Hewitt et al. |
| 2019/0192168 A1 | 6/2019 | Lorenzo et al. |
| 2019/0223878 A1 | 7/2019 | Lorenzo et al. |
| 2019/0223881 A1 | 7/2019 | Hewitt et al. |
| 2019/0269411 A1 | 9/2019 | Bardsley et al. |
| 2019/0269414 A1 | 9/2019 | Griffin |
| 2019/0274691 A1 | 9/2019 | Sepetka et al. |
| 2019/0282242 A1 | 9/2019 | Divino et al. |
| 2019/0290286 A1 | 9/2019 | Divino et al. |
| 2019/0298379 A1 | 10/2019 | Porter et al. |
| 2019/0343532 A1 | 11/2019 | Divino et al. |
| 2019/0343664 A1 | 11/2019 | Ruvalcaba et al. |
| 2019/0365385 A1 | 12/2019 | Gorochow et al. |
| 2020/0029973 A1 | 1/2020 | Walzman |
| 2020/0038032 A1 | 2/2020 | Rhee et al. |
| 2020/0038034 A1 | 2/2020 | Maguire et al. |
| 2020/0113576 A1 | 4/2020 | Gorochow et al. |
| 2020/0155333 A1 | 5/2020 | Franano et al. |
| 2020/0187952 A1 | 6/2020 | Walsh et al. |
| 2020/0187953 A1 | 6/2020 | Hamel et al. |
| 2020/0205841 A1 | 7/2020 | Aboytes et al. |
| 2020/0281603 A1 | 9/2020 | Marchand et al. |
| 2020/0289124 A1 | 9/2020 | Rangwala et al. |
| 2020/0289125 A1 | 9/2020 | Dholakia et al. |
| 2020/0289126 A1 | 9/2020 | Hewitt et al. |
| 2020/0305885 A1 | 10/2020 | Soto Del Valle et al. |
| 2020/0305886 A1 | 10/2020 | Soto Del Valle et al. |
| 2020/0323534 A1 | 10/2020 | Shimizu et al. |
| 2020/0367893 A1 | 11/2020 | Xu et al. |
| 2020/0367896 A1 | 11/2020 | Zaidat et al. |
| 2020/0367898 A1 | 11/2020 | Gorochow et al. |
| 2020/0367900 A1 | 11/2020 | Pedroso et al. |
| 2020/0367904 A1 | 11/2020 | Becking et al. |
| 2020/0367906 A1 | 11/2020 | Xu et al. |
| 2020/0375606 A1 | 12/2020 | Lorenzo |
| 2020/0375607 A1 | 12/2020 | Soto Del Valle et al. |
| 2020/0397447 A1 | 12/2020 | Lorenzo et al. |
| 2020/0405347 A1 | 12/2020 | Walzman |
| 2021/0007754 A1 | 1/2021 | Milhous et al. |
| 2021/0007755 A1 | 1/2021 | Lorenzo et al. |
| 2021/0052279 A1 | 2/2021 | Porter et al. |
| 2021/0085333 A1 | 3/2021 | Gorochow et al. |
| 2021/0106337 A1 | 4/2021 | Hewitt et al. |
| 2021/0106338 A1 | 4/2021 | Gorochow |
| 2021/0128160 A1 | 5/2021 | Li et al. |
| 2021/0128162 A1 | 5/2021 | Rhee et al. |
| 2021/0128165 A1 | 5/2021 | Pulugurtha et al. |
| 2021/0128167 A1 | 5/2021 | Patel et al. |
| 2021/0128168 A1 | 5/2021 | Nguyen et al. |
| 2021/0128169 A1 | 5/2021 | Li et al. |
| 2021/0129275 A1 | 5/2021 | Nguyen et al. |
| 2021/0137526 A1 | 5/2021 | Lee et al. |
| 2021/0145449 A1 | 5/2021 | Gorochow |
| 2021/0153871 A1 | 5/2021 | Griffin |
| 2021/0153872 A1 | 5/2021 | Nguyen et al. |
| 2021/0169495 A1 | 6/2021 | Gorochow et al. |
| 2021/0169498 A1 | 6/2021 | Gorochow |
| 2021/0177429 A1 | 6/2021 | Lorenzo |
| 2021/0186518 A1 | 6/2021 | Gorochow et al. |
| 2021/0196284 A1 | 7/2021 | Gorochow et al. |
| 2021/0228214 A1 | 7/2021 | Bowman et al. |
| 2021/0244420 A1 | 8/2021 | Aboytes et al. |
| 2021/0259699 A1 | 8/2021 | Rosenbluth et al. |
| 2021/0275184 A1 | 9/2021 | Hewitt et al. |
| 2021/0275187 A1 | 9/2021 | Franano et al. |
| 2021/0275779 A1 | 9/2021 | Northrop |
| 2021/0282784 A1 | 9/2021 | Sepetka et al. |
| 2021/0282785 A1 | 9/2021 | Dholakia et al. |
| 2021/0282789 A1 | 9/2021 | Vu et al. |
| 2021/0330331 A1 | 10/2021 | Lorenzo |
| 2021/0338247 A1 | 11/2021 | Gorochow |
| 2021/0338250 A1 | 11/2021 | Gorochow et al. |
| 2021/0346032 A1 | 11/2021 | Patterson et al. |
| 2021/0353299 A1 | 11/2021 | Hamel et al. |
| 2021/0353300 A1 | 11/2021 | Kottenmeier et al. |
| 2021/0378681 A1 | 12/2021 | Aboytes et al. |
| 2022/0022884 A1 | 1/2022 | Wolfe et al. |

(56) References Cited

U.S. PATENT DOCUMENTS

| | | |
|---|---|---|
| 2022/0022886 A1 | 1/2022 | Becking et al. |
| 2022/0031334 A1 | 2/2022 | Aguilar |
| 2022/0039804 A1 | 2/2022 | Rangwala et al. |
| 2022/0054141 A1 | 2/2022 | Zaidat et al. |
| 2022/0087681 A1 | 3/2022 | Xu et al. |
| 2022/0104829 A1 | 4/2022 | Gorochow et al. |
| 2022/0151632 A1 | 5/2022 | Walsh et al. |
| 2022/0175389 A1 | 6/2022 | Wallace et al. |
| 2022/0192678 A1 | 6/2022 | Hewitt et al. |
| 2022/0202425 A1 | 6/2022 | Gorochow et al. |
| 2022/0211383 A1 | 7/2022 | Pereira et al. |
| 2022/0225997 A1 | 7/2022 | Soto Del Valle et al. |
| 2022/0249098 A1 | 8/2022 | Milhous et al. |
| 2022/0257258 A1 | 8/2022 | Hewitt et al. |
| 2022/0257260 A1 | 8/2022 | Hewitt et al. |
| 2022/0313274 A1 | 10/2022 | Griffin |
| 2022/0330947 A1 | 10/2022 | Henkes et al. |
| 2022/0370078 A1 | 11/2022 | Chen et al. |
| 2023/0016312 A1 | 1/2023 | Xu et al. |
| 2023/0017150 A1 | 1/2023 | Lee et al. |
| 2023/0031965 A1 | 2/2023 | Sivapatham |
| 2023/0039246 A1 | 2/2023 | Hossan et al. |
| 2023/0039773 A1 | 2/2023 | Monstadt et al. |
| 2023/0061363 A1 | 3/2023 | Yee et al. |
| 2023/0107778 A1 | 4/2023 | Cox et al. |
| 2023/0114169 A1 | 4/2023 | Hewitt et al. |
| 2023/0157696 A1 | 5/2023 | Carrillo |
| 2023/0165587 A1 | 6/2023 | Carrillo |
| 2023/0190292 A1 | 6/2023 | Choubey et al. |
| 2023/0225735 A1 | 7/2023 | Kulak et al. |
| 2023/0240686 A1 | 8/2023 | Ashby et al. |
| 2023/0252631 A1 | 8/2023 | Kashyap et al. |
| 2023/0263528 A1 | 8/2023 | Jones |
| 2023/0277184 A1 | 9/2023 | Rashidi et al. |
| 2023/0285031 A1 | 9/2023 | Mayer et al. |

\* cited by examiner

| | |
|---|---|
| 101 | forming a longitudinal tubular mesh, wherein the mesh has a proximal end, a distal end, a longitudinal axis between the proximal end and the distal end, and radial cross-sections which are orthogonal to the longitudinal axis |
| 102 | radially-constraining the proximal end and the distal end of the mesh |
| 103 | dividing the mesh into a convex proximal portion of the mesh and a convex distal portion by radially-constraining a middle location on the mesh, wherein the middle location is somewhere between the proximal and distal ends |
| 104 | collapsing the proximal portion onto itself by moving the middle location in a proximal direction toward the proximal end of the mesh |
| 105 | delivering the mesh through a catheter to a cerebral aneurysm |
| 106 | inserting the mesh into the sac of the aneurysm, wherein the distal end of the mesh is closer to the dome of the aneurysm sac than the proximal end of the mesh, and wherein the proximal end of the mesh is closer to the neck of the aneurysm than the distal end of the mesh |
| 107 | expanding the distal portion by inserting embolic members and/or embolic material into the distal portion |

Fig. 1

METHODS FOR CREATING AN EXPANDABLE TWO-PART INTRASACULAR ANEURYSM OCCLUSION DEVICE FROM A TUBULAR MESH

CROSS-REFERENCE TO RELATED APPLICATIONS

This application is a continuation-in-part of U.S. patent application Ser. No. 18/374,602 filed on 2023 Sep. 28, a continuation-in-part of U.S. patent application Ser. No. 18/135,153 filed on 2023 Apr. 15, a continuation-in-part of U.S. patent application Ser. No. 17/970,510 filed on 2022 Oct. 20, a continuation-in-part of U.S. patent application Ser. No. 17/965,502 filed on 2022 Oct. 13, and a continuation-in-part of U.S. patent application Ser. No. 17/829,313 filed on 2022 May 31.

U.S. patent application Ser. No. 18/374,602 was a continuation-in-part of U.S. patent application Ser. No. 18/135,153 filed on 2023 Apr. 15, a continuation-in-part of U.S. patent application Ser. No. 17/970,510 filed on 2022 Oct. 20, a continuation-in-part of U.S. patent application Ser. No. 17/965,502 filed on 2022 Oct. 13, and a continuation-in-part of U.S. patent application Ser. No. 17/829,313 filed on 2022 May 31.

U.S. patent application Ser. No. 18/135,153 was a continuation-in-part of U.S. patent application Ser. No. 17/970,510 filed on 2022 Oct. 20, a continuation-in-part of U.S. patent application Ser. No. 17/965,502 filed on 2022 Oct. 13, and a continuation-in-part of U.S. patent application Ser. No. 17/829,313 filed on 2022 May 31. U.S. patent application Ser. No. 17/970,510 was a continuation-in-part of U.S. patent application Ser. No. 17/965,502 filed on 2022 Oct. 13, a continuation-in-part of U.S. patent application Ser. No. 17/829,313 filed on 2022 May 31, and a continuation-in-part of U.S. patent application Ser. No. 17/476,845 filed on 2021 Sep. 16.

U.S. patent application Ser. No. 17/829,313 was a continuation-in-part of U.S. patent application Ser. No. 17/485,390 filed on 2021 Sep. 25, was a continuation-in-part of U.S. patent application Ser. No. 17/476,845 filed on 2021 Sep. 16, was a continuation-in-part of U.S. patent application Ser. No. 17/472,674 filed on 2021 Sep. 12, was a continuation-in-part of U.S. patent application Ser. No. 17/467,680 filed on 2021 Sep. 7, was a continuation-in-part of U.S. patent application Ser. No. 17/466,497 filed on 2021 Sep. 3, was a continuation-in-part of U.S. patent application Ser. No. 17/353,652 filed on 2021 Jun. 21, was a continuation-in-part of U.S. patent application Ser. No. 17/220,002 filed on 2021 Apr. 1, was a continuation-in-part of U.S. patent application Ser. No. 17/214,827 filed on 2021 Mar. 27, was a continuation-in-part of U.S. patent application Ser. No. 17/211,446 filed on 2021 Mar. 24, was a continuation-in-part of U.S. patent application Ser. No. 16/693,267 filed on 2019 Nov. 23, and was a continuation-in-part of U.S. patent application Ser. No. 16/660,929 filed on 2019 Oct. 23.

U.S. patent application Ser. No. 17/220,002 was a continuation-in-part of U.S. patent application Ser. No. 17/214,827 filed on 2021 Mar. 27. U.S. patent application Ser. No. 17/220,002 was a continuation-in-part of U.S. patent application Ser. No. 17/211,446 filed on 2021 Mar. 24. U.S. patent application Ser. No. 17/220,002 claimed the priority benefit of U.S. provisional patent application 63/119,774 filed on 2020 Dec. 1. U.S. patent application Ser. No. 17/220,002 was a continuation-in-part of U.S. patent application Ser. No. 16/693,267 filed on 2019 Nov. 23. U.S. patent application Ser. No. 17/220,002 was a continuation-in-part of U.S. patent application Ser. No. 16/660,929 filed on 2019 Oct. 23.

U.S. patent application Ser. No. 16/693,267 was a continuation-in-part of U.S. patent application Ser. No. 16/660,929 filed on 2019 Oct. 23. U.S. patent application Ser. No. 16/693,267 claimed the priority benefit of U.S. provisional patent application 62/794,609 filed on 2019 Jan. 19. U.S. patent application Ser. No. 16/693,267 claimed the priority benefit of U.S. provisional patent application 62/794,607 filed on 2019 Jan. 19. U.S. patent application Ser. No. 16/693,267 was a continuation-in-part of U.S. patent application Ser. No. 16/541,241 filed on 2019 Aug. 15. U.S. patent application Ser. No. 16/693,267 was a continuation-in-part of U.S. patent application Ser. No. 15/865,822 filed on 2018 Jan. 9 which issued as U.S. patent Ser. No. 10/716,573 on 2020 Jul. 21. U.S. patent application Ser. No. 16/693,267 was a continuation-in-part of U.S. patent application Ser. No. 15/861,482 filed on 2018 Jan. 3.

U.S. patent application Ser. No. 16/660,929 claimed the priority benefit of U.S. provisional patent application 62/794,609 filed on 2019 Jan. 19. U.S. patent application Ser. No. 16/660,929 claimed the priority benefit of U.S. provisional patent application 62/794,607 filed on 2019 Jan. 19. U.S. patent application Ser. No. 16/660,929 was a continuation-in-part of U.S. patent application Ser. No. 16/541,241 filed on 2019 Aug. 15. U.S. patent application Ser. No. 16/660,929 was a continuation-in-part of U.S. patent application Ser. No. 15/865,822 filed on 2018 Jan. 9 which issued as U.S. patent Ser. No. 10/716,573 on 2020 Jul. 21. U.S. patent application Ser. No. 16/660,929 was a continuation-in-part of U.S. patent application Ser. No. 15/861,482 filed on 2018 Jan. 3.

U.S. patent application Ser. No. 16/541,241 claimed the priority benefit of U.S. provisional patent application 62/794,609 filed on 2019 Jan. 19. U.S. patent application Ser. No. 16/541,241 claimed the priority benefit of U.S. provisional patent application 62/794,607 filed on 2019 Jan. 19. U.S. patent application Ser. No. 16/541,241 claimed the priority benefit of U.S. provisional patent application 62/720,173 filed on 2018 Aug. 21. U.S. patent application Ser. No. 16/541,241 was a continuation-in-part of U.S. patent application Ser. No. 15/865,822 filed on 2018 Jan. 9 which issued as U.S. patent Ser. No. 10/716,573 on 2020 Jul. 21

U.S. patent application Ser. No. 15/865,822 claimed the priority benefit of U.S. provisional patent application 62/589,754 filed on 2017 Nov. 22. U.S. patent application Ser. No. 15/865,822 claimed the priority benefit of U.S. provisional patent application 62/472,519 filed on 2017 Mar. 16. U.S. patent application Ser. No. 15/865,822 was a continuation-in-part of U.S. patent application Ser. No. 15/081,909 filed on 2016 Mar. 27. U.S. patent application Ser. No. 15/865,822 was a continuation-in-part of U.S. patent application Ser. No. 14/526,600 filed on 2014 Oct. 29.

U.S. patent application Ser. No. 15/861,482 claimed the priority benefit of U.S. provisional patent application 62/589,754 filed on 2017 Nov. 22. U.S. patent application Ser. No. 15/861,482 claimed the priority benefit of U.S. provisional patent application 62/472,519 filed on 2017 Mar. 16. U.S. patent application Ser. No. 15/861,482 claimed the priority benefit of U.S. provisional patent application 62/444,860 filed on 2017 Jan. 11. U.S. patent application Ser. No. 15/861,482 was a continuation-in-part of U.S. patent application Ser. No. 15/080,915 filed on 2016 Mar. 25 which issued as U.S. patent Ser. No. 10/028,747 on 2018 Jul. 24. U.S. patent application Ser. No. 15/861,482 was a continuation-in-part of U.S. patent application Ser. No. 14/526,600 filed on 2014 Oct. 29.

U.S. patent application Ser. No. 15/081,909 was a continuation-in-part of U.S. patent application Ser. No. 14/526,600 filed on 2014 Oct. 29. U.S. patent application Ser. No. 15/080,915 was a continuation-in-part of U.S. patent application Ser. No. 14/526,600 filed on 2014 Oct. 29. U.S. patent application Ser. No. 14/526,600 claimed the priority benefit of U.S. provisional patent application 61/897,245 filed on 2013 Oct. 30. U.S. patent application Ser. No. 14/526,600 was a continuation-in-part of U.S. patent application Ser. No. 12/989,048 filed on 2010 Oct. 21 which issued as U.S. Pat. No. 8,974,487 on 2015 Mar. 10. U.S. patent application Ser. No. 12/989,048 claimed the priority benefit of U.S. provisional patent application 61/126,047 filed on 2008 May 1. U.S. patent application Ser. No. 12/989,048 claimed the priority benefit of U.S. provisional patent application 61/126,027 filed on 2008 May 1.

The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to devices and methods for occluding a cerebral aneurysm.

INTRODUCTION

An aneurysm is an abnormal bulging of a blood vessel wall. The vessel from which the aneurysm protrudes is the parent vessel. Saccular aneurysms look like a sac protruding out from the parent vessel. Saccular aneurysms have a neck and can be prone to rupture. Fusiform aneurysms are a form of aneurysm in which a blood vessel is expanded circumferentially in all directions. Fusiform aneurysms generally do not have a neck and are less prone to rupturing than saccular aneurysms. As an aneurysm grows larger, its walls generally become thinner and weaker. This decrease in wall integrity, particularly for saccular aneurysms, increases the risk of the aneurysm rupturing and hemorrhaging blood into the surrounding tissue, with serious and potentially fatal health outcomes.

Cerebral aneurysms, also called brain aneurysms or intracranial aneurysms, are aneurysms that occur in the intercerebral arteries that supply blood to the brain. The majority of cerebral aneurysms form at the junction of arteries at the base of the brain that is known as the Circle of Willis where arteries come together and from which these arteries send branches to different areas of the brain. Although identification of intact aneurysms is increasing due to increased use of outpatient imaging such as outpatient MRI scanning, many cerebral aneurysms still remain undetected unless they rupture. If they do rupture, they often cause stroke, disability, and/or death. The prevalence of cerebral aneurysms is generally estimated to be in the range of 1%-5% of the general population or approximately 3-15 million people in the U.S. alone. Approximately 30,000 people per year suffer a ruptured cerebral aneurysm in the U.S. alone. Approximately one-third to one-half of people who suffer a ruptured cerebral aneurysm die within one month of the rupture. Sadly, even among those who survive, approximately one-half suffer significant and permanent deterioration of brain function. Better alternatives for cerebral aneurysm treatment are needed.

REVIEW OF THE RELEVANT ART

U.S. Pat. No. 8,998,947 (Aboytes et al., Apr. 7, 2015, "Devices and Methods for the Treatment of Vascular Defects") discloses an expandable implant that with a first configuration in which the first portion and the second portion are substantially linearly aligned and a second configuration in which the second portion at least partially overlaps the first portion. U.S. patent application 20200205841 (Aboytes et al., Jul. 2, 2020, "Devices, Systems, and Methods for the Treatment of Vascular Defects") and U.S. patent application 20210378681 (Aboytes et al., Dec. 9, 2021, "Devices, Systems, and Methods for the Treatment of Vascular Defects") disclose aneurysm occlusion devices with a first configuration in which a first portion and a second portion are substantially linearly aligned and a second configuration in which the second portion at least partially overlaps the first portion. U.S. patent application 20210244420 (Aboytes et al., Aug. 12, 2021, "Devices and Methods for the Treatment of Vascular Defects") discloses aneurysm occlusion devices with a first configuration in which a first portion and a second portion are substantially linearly aligned and a second configuration in which the second portion at least partially overlaps the first portion.

U.S. patent application 20220031334 (Aguilar, Feb. 3, 2022, "Expandable Devices for Treating Body Lumens") discloses an occlusive device comprising an expandable mesh including an outer mesh and an inner mesh disposed within the outer mesh. U.S. patent application 20230240686 (Ashby et al., Aug. 3, 2023, "Occlusive Devices with Spiral Struts for Treating Vascular Defects") discloses an occlusive device with a plurality of spiral struts. U.S. patent Ser. No. 11/185,335 (Badruddin et al., Nov. 30, 2021, "System for and Method of Treating Aneurysms") discloses an apparatus for treating an aneurysm with an occlusion element disposed on a wire, wherein the occlusion element includes a cover for covering a neck of an aneurysm and an inner anchoring member. U.S. patent application 20170079661 (Bardsley et al., Mar. 23, 2017, "Occlusive Devices"), U.S. patent Ser. No. 10/314,593 (Bardsley et al., Jun. 11, 2019, "Occlusive Devices"), and U.S. patent application 20190269411 (Bardsley et al., Sep. 5, 2019, "Occlusive Devices") disclose an implant with a single- or dual-layer braided body with variable porosity.

U.S. patent application 20110208227 (Becking, Aug. 25, 2011, "Filamentary Devices for Treatment of Vascular Defects") discloses braid-balls for aneurysm occlusion. U.S. patent application 20120316598 (Becking et al., Dec. 13, 2012, "Multiple Layer Filamentary Devices for Treatment of Vascular Defects") and U.S. Pat. No. 9,585,669 (Becking et al., Mar. 17, 2017, "Multiple Layer Filamentary Devices for Treatment of Vascular Defects") disclose braid balls for aneurysm occlusion. U.S. Pat. No. 9,039,726 (Becking, May 26, 2015, "Filamentary Devices for Treatment of Vascular Defects") discloses braid-balls for aneurysm occlusion. U.S. patent application 20200367904 (Becking et al., Nov. 26, 2020, "Multiple Layer Filamentary Devices for Treatment of Vascular Defects") and U.S. patent application 20220022886 (Becking et al., Jan. 27, 2022, "Multiple Layer Filamentary Devices for Treatment of Vascular Defects") disclose braid-balls suitable for aneurysm occlusion.

U.S. patent application 20210228214 (Bowman et al., Jul. 29, 2021, "Devices for Vascular Occlusion") discloses a method of using and delivering an occlusive device. U.S. patent application 20230157696 (Carrillo, May 25, 2023, "Aneurysm Treatment Device and Associated Systems and Methods of Use") discloses an aneurysm treatment device with a tip portion, a body portion, and a base portion. U.S. patent application 20230165587 (Carrillo, Jun. 1, 2023, "Expandable Devices for Treating Body Lumens") discloses an expandable cage with a plurality of mesh stents which receives embolic material therein. U.S. patent application 20220370078 (Chen et al., Nov. 24, 2022, "Vaso-Occlusive Devices") discloses a vaso-occlusive structure made with a gold-platinum-tungsten alloy. U.S. patent application 20230190292 (Choubey et al., Jun. 22, 2023, "Occlusive Devices with Petal-Shaped Regions for Treating Vascular Defects") discloses an occlusive device for treating an aneurysm with a mesh formed from a tubular braid, including a petal-shaped region formed from a flattened section of the tubular braid.

U.S. patent application 20120165919 (Cox et al., Jun. 28, 2012, "Methods and Devices for Treatment of Vascular Defects") and U.S. patent application 20140052233 (Cox et al., Feb. 20, 2014, "Methods and Devices for Treatment of Vascular Defects") disclose an expandable wire body support structure having a low profile radially constrained state, an expanded relaxed state with a substantially spherical or globular configuration having a smooth outer surface, and a porous permeable layer comprising a braided wire occlusive mesh. U.S. patent application 20120283768 (Cox et al., Nov. 8, 2012, "Method and Apparatus for the Treatment of Large and Giant Vascular Defects") discloses the deployment of multiple permeable shell devices within a single vascular defect. U.S. patent Ser. No. 11/179,159 (Cox et al., Nov. 23, 2021, "Methods and Devices for Treatment of Vascular Defects") discloses a device comprising a first hub, a second hub, a support structure having a longitudinal axis, the support structure disposed between the first hub and the second hub, the support structure including a plurality of struts, and a layer of material disposed over the plurality of struts, wherein the first hub is cylindrical and connected to an end of each of the struts of the plurality of struts. U.S. patent application 20230107778 (Cox et al., Apr. 6, 2023, "Methods and Devices for Treatment of Vascular Defects") discloses an expandable body comprising a plurality of elongate filamentary elements each having a first end and a second end, wherein the elements extend from a first end of the device to a second end of the device and back to the first end of the device. U.S. patent application 20110022149 (Cox et al., Jan. 27, 2011, "Methods and Devices for Treatment of Vascular Defects") discloses a device with first ends secured to a first ring and second ends secured to a second ring with the first and second rings being disposed substantially concentric to the longitudinal axis.

U.S. patent application 20200289125 (Dholakia et al., Sep. 17, 2020, "Filamentary Devices Having a Flexible Joint for Treatment of Vascular Defects") discloses an implant with a first permeable shell having a proximal end with a concave or recessed section and a second permeable shell having a convex section that mates with the concave or recessed section. U.S. patent application 20210282785 (Dholakia et al., Sep. 16, 2021, "Devices Having Multiple Permeable Shells for Treatment of Vascular Defects") a device with a plurality of permeable shells connected by a plurality of coils.

U.S. patent applications 20140135811 (Divino et al., May 15, 2014, "Occlusive Devices"), 20140135812 (Divino et al., May 15, 2014, "Occlusive Devices"), 20190282242 (Divino et al., Sep. 19, 2019, "Occlusive Devices"), and 20190290286 (Divino et al., Sep. 26, 2019, "Occlusive Devices") and also U.S. patent Ser. No. 10/327,781 (Divino et al., Jun. 25, 2019, "Occlusive Devices") disclose multiple expandable structures, wherein each of the expandable structures has a unique shape or porosity profile. U.S. patent application 20170281194 (Divino et al., Oct. 5, 2017, "Embolic Medical Devices") discloses an occlusive device with an elongate member having opposing first and second side edges which extend longitudinally along the member and a member width, wherein this member has a collapsed configuration in which the first and second side edges are curled toward each other about a longitudinal axis of the member. U.S. patent application 20190343532 (Divino et al., Nov. 14, 2019, "Occlusive Devices") discloses a device with at least one expandable structure which is adapted to transition from a compressed configuration to an expanded configuration when released into an aneurysm.

U.S. patent application 20200155333 (Franano et al., May 21, 2020, "Ballstent Device and Methods of Use") discloses a rounded, thin-walled, expandable metal structure and a flexible, elongated delivery device. U.S. patent Ser. No. 11/013,516 (Franano et al., May 25, 2021, "Expandable Body Device and Method of Use") discloses a single-lobed, thin-walled, expandable body comprising gold, platinum, or silver. U.S. patent Ser. No. 11/033,275 (Franano et al., Jun. 15, 2021, "Expandable Body Device and Method of Use") discloses devices, designs, methods of manufacturing and using hollow gold structures that can be folded, wrapped, and compressed. U.S. patent application 20210275187 (Franano et al., Sep. 9, 2021, "Expandable Body Device and Method of Use") discloses medical devices comprising a single-lobed, thin-walled, expandable body. U.S. patent application 20190053811 (Garza et al., Feb. 21, 2019, "Flow Attenuation Device") and U.S. patent Ser. No. 11/071,551 (Garza et al., Jul. 27, 2021, "Flow Attenuation Device") disclose an embolic device for treating aneurysms with a desired porosity only at discrete sections.

U.S. patent application 20190365385 (Gorochow et al., Dec. 5, 2019, "Aneurysm Device and Delivery System") and U.S. patent Ser. No. 10/939,915 (Gorochow et al., Mar. 9, 2021, "Aneurysm Device and Delivery System") discloses a braid, wherein translating the braid causes a delivery portion to expand and form a distal sack as well as invert into itself. U.S. patent application 20200113576 (Gorochow et al., Apr. 16, 2020, "Folded Aneurysm Treatment Device and Delivery Method") and U.S. patent application 20210196284 (Gorochow et al., Jul. 1, 2021, "Folded Aneurysm Treatment Device and Delivery Method") disclose an implant having a braided section that folds to form an outer occlusive sack extending across a neck of an aneurysm to engage a wall of the aneurysm from within a sac of the aneurysm and an inner occlusive sack forming a trough nested within the outer occlusive sack. The implant can be closed at one or more of the braid ends to define a substantially enclosed bowl-shaped volume.

U.S. patent Ser. No. 10/653,425 (Gorochow et al., May 19, 2020, "Layered Braided Aneurysm Treatment Device"), U.S. patent application 20200367893 (Xu et al., Nov. 26, 2020, "Layered Braided Aneurysm Treatment Device"), U.S. patent application 20200367898 (Gorochow et al., Nov.

26, 2020, "Layered Braided Aneurysm Treatment Device"), U.S. patent Ser. No. 11/413,046 (Xu et al., Aug. 16, 2022, "Layered Braided Aneurysm Treatment Device"), and U.S. patent application 20200367900 (Pedroso et al., Nov. 26, 2020, "Layered Braided Aneurysm Treatment Device With Corrugations") disclose a tubular braid comprising an open end, a pinched end, and a predetermined shape; wherein, in the predetermined shape, the tubular braid comprises: a first segment extending from the open end to a first inversion, a second segment encircled by the open end such that the second segment is only partially surrounded by the first segment and extending from the first inversion to a second inversion, and a third segment surrounded by the second segment and extending from the second inversion to the pinched end.

U.S. patent application 20210085333 (Gorochow et al., Mar. 25, 2021, "Inverting Braided Aneurysm Treatment System and Method"), U.S. patent Ser. No. 11/278,292 (Gorochow et al., Mar. 22, 2022, "Inverting Braided Aneurysm Treatment System and Method"), and U.S. patent application 20220104829 (Gorochow et al., Apr. 7, 2022, "Inverting Braided Aneurysm Treatment System and Method") disclose a tubular braid with an intrasaccular section, an intravascular section, a pinched section, and a predetermined shape. U.S. patent application 20210169495 (Gorochow et al., Jun. 10, 2021, "Intrasaccular Inverting Braid with Highly Flexible Fill Material") and U.S. patent Ser. No. 11/602,350 (Gorochow et al., Mar. 14, 2023, "Intrasaccular Inverting Braid with Highly Flexible Fill Material") disclose a tubular braided implant which is delivered as a single layer braid, inverted into itself during deployment to form at least two nested sacks and includes additional braid material that can fill the innermost sack.

U.S. patent application 20210186518 (Gorochow et al., Jun. 24, 2021, "Implant Having an Intrasaccular Section and Intravascular Section") and U.S. patent Ser. No. 11/457,926 (Gorochow et al., Oct. 4, 2022, "Implant Having an Intrasaccular Section and Intravascular Section") disclose a tubular braid with an intrasaccular section, an intravascular section, a pinched section, and a predetermined shape. U.S. patent Ser. No. 11/058,430 (Gorochow et al., Jul. 13, 2021, "Aneurysm Device and Delivery System") discloses a braid with a proximal expandable portion for positioning inside an aneurysm and sealing across the neck of the aneurysm. U.S. patent Ser. No. 11/076,861 (Gorochow et al., Aug. 3, 2021, "Folded Aneurysm Treatment Device and Delivery Method") discloses an implant with a fold which defines an annular ridge and a radiopaque marker band. U.S. patent application 20210106338 (Gorochow, Apr. 15, 2021, "Spiral Delivery System for Embolic Braid") discloses a braided implant having a spiral segment. U.S. patent application 20210145449 (Gorochow, May 20, 2021, "Implant Delivery System with Braid Cup Formation") discloses an implant system with an engagement wire, a pull wire, and a braided implant having a distal ring thereon. U.S. patent application 20210169498 (Gorochow, Jun. 10, 2021, "Delivery of Embolic Braid") discloses a braided implant delivery system which attaches a braided implant having a band to a delivery tube, positions the braided implant within an aneurysm, and then releases the band from the delivery tube. U.S. patent Ser. No. 11/051,825 (Gorochow, Jul. 6, 2021, "Delivery System for Embolic Braid") discloses a braided implant which is attached to a releasing component that can be detachably engaged with a delivery tube and a pull wire.

U.S. patent application 20210338250 (Gorochow et al., Nov. 4, 2021, "Intrasaccular Flow Diverter") and U.S. patent Ser. No. 11/523,831 (Gorochow et al., Dec. 13, 2022, "Intrasaccular Flow Diverter") disclose an interior fill braid physically which is inverted over itself to form a proximal inverted end and an opposite free end and a dome braid disposed distally of and secured to the interior fill braid. U.S. patent application 20220202425 (Gorochow et al., Jun. 30, 2022, "Semispherical Braided Aneurysm Treatment System and Method") discloses a tubular braid with three segments and two inversions, one of the three segments extending between the two inversions and forming a sack. U.S. patent application 20210338247 (Gorochow, Nov. 4, 2021, "Double Layer Braid") discloses a double layered braid for treating an aneurysm. U.S. patent Ser. No. 11/583,282 (Gorochow et al., Feb. 21, 2023, "Layered Braided Aneurysm Treatment Device") discloses a method for shaping a tubular braid into a predetermined shape. U.S. patent application 20180070955 (Greene et al., Mar. 15, 2018, "Embolic Containment") discloses a method of treating a neurovascular arteriovenous malformation with liquid embolic and dimethyl sulfoxide.

U.S. patent applications 20150313605 (Griffin, Nov. 5, 2015, "Occlusion Device") and 20190059909 (Griffin, Feb. 28, 2019, "Occlusion Device") and also U.S. patent Ser. No. 10/130,372 (Griffin, Nov. 20, 2018, "Occlusion Device") and U.S. Pat. No. 11,389,174 (Griffin, Jul. 19, 2022, "Occlusion Device") disclose an occlusion device with a substantially solid marker having a proximal end, and a distal end; and a low profile resilient mesh body attached to the distal end of the marker. U.S. patent application 20170156734 (Griffin, Jun. 8, 2017, "Occlusion Device"), U.S. patent Ser. No. 10/285,711 (Griffin, May 14, 2019, "Occlusion Device"), U.S. patent application 20190269414 (Griffin, Sep. 5, 2019, "Occlusion Device"), U.S. patent application 20210153871 (Griffin, May 27, 2021, "Occlusion Device"), and U.S. patent application 20220313274 (Griffin, Oct. 6, 2022, "Occlusion Device") disclose a continuous compressible mesh structure comprising axial mesh carriages configured end to end, wherein each end of each carriage is a pinch point in the continuous mesh structure. U.S. patent Ser. No. 11/471,162 (Griffin, Oct. 18, 2022, "Occlusion Device") discloses an occlusion device for implantation into a body lumen or aneurysm which has a continuous compressible mesh structure comprising axial mesh carriages configured end to end, wherein each end of each carriage is a pinch point in the continuous mesh structure.

U.S. patent application 20200187953 (Hamel et al., Jun. 18, 2020, "Devices, Systems, and Methods for the Treatment of Vascular Defects") discloses a mesh comprising a first end portion, a second end portion, and a length extending between the first and second end portions, and a first lateral edge, a second lateral edge, and a width extending between the first and second lateral edges. U.S. patent application 20210353299 (Hamel et al., Nov. 18, 2021, "Devices, Systems, and Methods for the Treatment of Vascular Defects") discloses a mesh that is curved along its length with an undulating contour across at least a portion of one or both of its length or its width. U.S. patent application 20220330947 (Henkes et al., Oct. 20, 2022, "Implant for the Treatment of Aneurysms") discloses an implant which is rolled up relative to a radial axis in order to form a balled-up configuration.

U.S. patent application 20140358178 (Hewitt et al., Dec. 4, 2014, "Filamentary Devices for Treatment of Vascular Defects"), U.S. Pat. No. 9,078,658 (Hewitt et al., Jul. 14, 2015, "Filamentary Devices for Treatment of Vascular Defects"), U.S. patent application 20160249934 (Hewitt et al., Sep. 1, 2016, "Filamentary Devices for Treatment of Vascular Defects"), U.S. Pat. No. 9,955,976 (Hewitt et al., May 1, 2018, "Filamentary Devices for Treatment of Vascular Defects"), U.S. patent application 20180206849 (Hewitt et al., Jul. 26, 2018, "Filamentary Devices for the Treatment of Vascular Defects"), U.S. patent application 20210007754 (Milhous et al., Jan. 14, 2021, "Filamentary Devices for Treatment of Vascular Defects"), U.S. patent Ser. No. 10/939,914 (Hewitt et al., Mar. 9, 2021, "Filamentary Devices for the Treatment of Vascular Defects"), and U.S. patent application 20210275184 (Hewitt et al., Sep. 9, 2021, "Filamentary Devices for Treatment of Vascular Defects") disclose occlusion devices with permeable shells made of woven braided mesh having a variable mesh density and/or porosity. U.S. patent application 20160249935 (Hewitt et al., Sep. 1, 2016, "Devices for Therapeutic Vascular Procedures"), U.S. patent application 20160367260 (Hewitt et al., Dec. 22, 2016, "Devices for Therapeutic Vascular Procedures"), U.S. Pat. No. 9,629,635 (Hewitt et al., Apr. 25, 2017, "Devices for Therapeutic Vascular Procedures"), and U.S. patent application 20170128077 (Hewitt et al., May 11, 2017, "Devices for Therapeutic Vascular Procedures") disclose a self-expanding resilient permeable shell and a metallic coil secured to the distal end of the permeable shell.

U.S. Pat. No. 9,492,174 (Hewitt et al., Nov. 15, 2016, "Filamentary Devices for Treatment of Vascular Defects"), U.S. patent application 20170095254 (Hewitt et al., Apr. 6, 2017, "Filamentary Devices for Treatment of Vascular Defects"), U.S. patent Ser. No. 10/136,896 (Hewitt et al., Nov. 27, 2018, "Filamentary Devices for Treatment of Vascular Defects"), U.S. patent application 20190192166 (Hewitt et al., Jun. 27, 2019, "Filamentary Devices for Treatment of Vascular Defects"), U.S. patent application 20200289124 (Rangwala et al., Sep. 17, 2020, "Filamentary Devices for Treatment of Vascular Defects"), U.S. patent Ser. No. 10/813,645 (Hewitt et al., Oct. 27, 2020, "Filamentary Devices for Treatment of Vascular Defects"), and U.S. patent application 20210106337 (Hewitt et al., Apr. 15, 2021, "Filamentary Devices for Treatment of Vascular Defects") disclose a self-expanding permeable shell having a radially constrained elongated state configured for delivery within a catheter lumen, an expanded state with a globular and longitudinally shortened configuration relative to the radially constrained state, and a plurality of elongate filaments that are woven together.

U.S. patent application 20190223881 (Hewitt et al., Jul. 25, 2019, "Devices for Therapeutic Vascular Procedures") discloses a self-expanding resilient permeable shell made from elongate resilient filaments with a distal region that extends beyond the distal end of the permeable shell. U.S. patent application 20200289126 (Hewitt et al., Sep. 17, 2020, "Filamentary Devices for Treatment of Vascular Defects"), U.S. patent Ser. No. 11/317,921 (Hewitt et al., May 3, 2022, "Filamentary Devices for Treatment of Vascular Defects"), and U.S. patent application 20220257258 (Hewitt et al., Aug. 18, 2022, "Filamentary Devices for Treatment of Vascular Defects") disclose a permeable shell or mesh with a stiffer proximal portion at the neck of an aneurysm. U.S. patent application 20220192678 (Hewitt et al., Jun. 23, 2022, "Filamentary Devices for Treatment of Vascular Defects") discloses an implant having a first permeable shell having a proximal hub and an open distal end and a second permeable shell having a distal hub and an open proximal end. U.S. patent application 20220257260 (Hewitt et al., Aug. 18, 2022, "Filamentary Devices for Treatment of Vascular Defects") discloses an implant having multiple mesh layers. U.S. patent application 20230114169 (Hewitt et al., Apr. 13, 2023, "Devices for Treatment of Vascular Defects") discloses a permeable woven implant with a radially-constrained state for delivery within a catheter and an expanded state thereafter.

U.S. patent application 20230039246 (Hossan et al., Feb. 9, 2023, "Non-Braided Biodegrable Flow Diverting Device for Endovascular Treatment of Aneurysm and Associated Fabrication Method") discloses a biodegradable flow-diverting device that regulates blood flow into an aneurysmal sac. U.S. patent application 20230263528 (Jones, Aug. 24, 2023, "Intrasacular Flow Diverter and Related Methods") discloses an intrasacular flow diverter with a plurality of wires which are coiled to form a collapsible, substantially spherical frame. U.S. patent application 20230252631 (Kashyap et al., Aug. 10, 2023, "Neural Network Apparatus for Identification, Segmentation, and Treatment Outcome Prediction for Aneurysms") discloses using using medical imaging and a neural network to predict outcomes from the potential use of one or more different intrasaccular implant devices. U.S. patent application 20210353300 (Kottenmeier et al., Nov. 18, 2021, "Systems and Methods for Treatment of Defects in the Vasculature") discloses aneurysm occlusion methods and systems including an expandable stent.

U.S. patent application 20230225735 (Kulak et al., Jul. 20, 2023, "Expandable Devices for Treating Body Lumens") discloses a tubular mesh which curves along its longitudinal dimension when implanted in an aneurysm cavity. U.S. patent application 20210137526 (Lee et al., May 13, 2021, "Embolic Devices for Occluding Body Lumens") discloses an embolic device with a first segment forming a first three-dimensional structure, wherein the first three-dimensional structure defines a cavity; and a second segment forming a second three-dimensional structure; wherein the cavity of the first three-dimensional structure is configured to accommodate at least a majority of the second three-dimensional structure. U.S. patent application 20230017150 (Lee et al., Jan. 19, 2023, "Hydrogel Stent and Embolization Device for Cerebral Aneurysm") discloses a hydrogel stent for occluding a cerebral aneurysm.

U.S. patent application 20210128169 (Li et al., May 6, 2021, "Devices, Systems, and Methods for Treatment of Intracranial Aneurysms") and U.S. patent application 20210153872 (Nguyen et al., May 27, 2021, "Devices, Systems, and Methods for Treatment of Intracranial Aneurysms") disclose delivering an occlusive member to an aneurysm cavity and deforming a shape of the occlusive member via introduction of an embolic element to a space between the occlusive member and an inner surface of the aneurysm wall. U.S. patent application 20210128160 (Li et al., May 6, 2021, "Systems and Methods for Treating Aneurysms"), U.S. patent application 20210128167 (Patel et al., May 6, 2021, "Systems and Methods for Treating Aneurysms"), U.S. patent application 20210128168 (Nguyen et al., May 6, 2021, "Systems and Methods for Treating Aneurysms") and disclose delivering an occlusive member (e.g., an expandable braid) to an aneurysm sac in conjunction with an embolic element (e.g., coils, embolic material).

U.S. patent application 20190192168 (Lorenzo et al., Jun. 27, 2019, "Aneurysm Device and Delivery Method") and U.S. patent Ser. No. 10/716,574 (Lorenzo et al., Jul. 21, 2020, "Aneurysm Device and Delivery Method") discloses a self-expanding braid for treating an aneurysm, including a method for inverting and buckling a proximal segment. U.S. patent application 20190223878 (Lorenzo et al., Jul. 25, 2019, "Aneurysm Device and Delivery System") and U.S. patent application 20200397447 (Lorenzo et al., Dec. 24, 2020, "Aneurysm Device and Delivery System") discloses an expandable segment which radially expands inside an outer occlusive sack. U.S. patent application 20210007755 (Lorenzo et al., Jan. 14, 2021, "Intrasaccular Aneurysm Treatment Device with Varying Coatings") discloses an aneurysm intrasaccular implant with coated regions. U.S. patent Ser. No. 10/905,430 (Lorenzo et al., Feb. 2, 2021, "Aneurysm Device and Delivery System") discloses an expandable segment which radially expands inside an outer occlusive sack.

U.S. patent applications 20150272589 (Lorenzo, Oct. 1, 2015, "Aneurysm Occlusion Device") and 20190008522 (Lorenzo, Jan. 10, 2019, "Aneurysm Occlusion Device") and also U.S. patent Ser. No. 11/076,860 (Lorenzo, Aug. 3, 2021, "Aneurysm Occlusion Device") disclose a tubular structure which is constrained by a control ring. U.S. patent application 20180242979 (Lorenzo, Aug. 30, 2018, "Aneurysm Device and Delivery System") and U.S. patent Ser. No. 10/751,066 (Lorenzo, Aug. 25, 2020, "Aneurysm Device and Delivery System") disclose a self-expanding braided tubular member. U.S. patent application 20200375606 (Lorenzo, Dec. 3, 2020, "Aneurysm Method and System") discloses a braided implant which is invertible about the distal implant end. U.S. patent application 20210177429 (Lorenzo, Jun. 17, 2021, "Aneurysm Method and System") discloses a vaso-occlusive device with at least two nested sacks. U.S. patent Ser. No. 11/123,077 (Lorenzo et al., Sep. 21, 2021, "Intrasaccular Device Positioning and Deployment System") discloses implant deployment systems including a braided implant that can be detachably attached to a delivery tube by an expansion ring. U.S. patent application 20210330331 (Lorenzo, Oct. 28, 2021, "Aneurysm Occlusion Device") and U.S. patent Ser. No. 11/154,302 (Lorenzo et al., Oct. 26, 2021, "Aneurysm Occlusion Device") disclose an occlusion device with a substantially annular body disposed on the proximal end region of the device. U.S. patent application 20200038034 (Maguire et al., Feb. 6, 2020, "Vessel Occluder") discloses a vessel occluder with an expandable mesh portion having a flexible membrane that expands within a cavity of the expandable mesh portion.

U.S. patent application 20130245667 (Marchand et al., Sep. 19, 2013, "Filamentary Devices and Treatment of Vascular Defects") discloses a self-expanding resilient permeable shell wherein filaments are bundled and secured to each other at a proximal end. U.S. patent application 20160249937 (Marchand et al., Sep. 1, 2016, "Multiple Layer Filamentary Devices for Treatment of Vascular Defects"), U.S. Pat. No. 9,918,720 (Marchand et al., Mar. 20, 2018, "Multiple Layer Filamentary Devices for Treatment of Vascular Defects"), and U.S. patent Ser. No. 10/238,393 (Marchand et al., Mar. 26, 2019, "Multiple Layer Filamentary Devices for Treatment of Vascular Defects") disclose a permeable shell and an inner structure configured to occlude blood flow. U.S. patent application 20180000489 (Marchand et al., Jan. 4, 2018, "Filamentary Devices for Treatment of Vascular Defects") discloses a self-expanding resilient permeable shell having a plurality of elongate resilient filaments with a woven structure. U.S. patent Ser. No. 10/610,231 (Marchand et al., Apr. 7, 2020, "Filamentary Devices for Treatment of Vascular Defects") discloses a self-expanding resilient permeable shell with a plurality of elongate resilient filaments with a woven structure, wherein the plurality of filaments includes small filaments and large filaments, and wherein the small filaments have a transverse dimension which is smaller than the transverse dimension of the large filaments. U.S. patent application 20200281603 (Marchand et al., Sep. 10, 2020, "Filamentary Devices for Treatment of Vascular Defects") discloses a permeable shell including a really swell polymer.

U.S. patent Ser. No. 11/517,321 (Mauger et al., Dec. 6, 2022, "System and Methods for Embolized Occlusion of Neurovascular Aneurysms") discloses an occlusion device with a reinforcing portion with no porosity. U.S. patent Ser. No. 11/589,872 (Mauger, Feb. 28, 2023, "Vascular Occlusion Devices Utilizing Thin Film Nitinol Foils") discloses an implantable occlusion device wherein mesh components are wrapped around a support structure and slot that enables a disc to be wrapped around the support structure with overlapping portions. U.S. patent application 20230285031 (Mayer et al, Sep. 14, 2023, "Device for Restricting Blood Flow to Aneurysms") discloses a non-occlusive device with a coilable section and a docking section. U.S. patent application 20220249098 (Milhous et al., Aug. 11, 2022, "Filamentary Devices for Treatment of Vascular Defects") discloses a permeable implant with a plurality of scaffolding filaments. U.S. patent application 20230039773 (Monstadt et al., Feb. 9, 2023, "Implant for Treating Aneurysms") discloses an implant which is preset to a specific structure.

U.S. patent Ser. No. 11/426,175 (Morita et al., Aug. 30, 2022, "Expansile Member") discloses an occlusive system comprising: a catheter; a shell deliverable through the catheter, a delivery pusher detachably connected to the shell and configured to navigate the shell through the catheter, wherein the shell has a globular shaped portion. U.S. patent application 20210129275 (Nguyen et al., May 6, 2021, "Devices, Systems, and Methods for Treating Aneurysms") discloses methods of manufacturing an occlusive device including conforming a mesh to a forming assembly and setting a shape of the mesh based on the forming assembly. U.S. patent application 20210275779 (Northrop, Sep. 9, 2021, "Actuating Elements for Bending Medical Devices") discloses an actuating element causes a tube to bend. U.S. patent Ser. No. 11/498,165 (Patel et al., Nov. 15, 2022, "Systems and Methods for Treating Aneurysms") discloses an occlusive implant with a conduit which receives a liquid embolic.

U.S. patent application 20210346032 (Patterson et al., Nov. 11, 2021, "Devices for Treatment of Vascular Defects") discloses an expandable stent for placement in a parent vessel proximal, near, or adjacent an aneurysm. U.S. patent Ser. No. 11/607,226 (Pedroso et al., Mar. 21, 2023, "Layered Braided Aneurysm Treatment Device with Corrugations") discloses an implant with a proximal inversion and two segments. U.S. patent Ser. No. 11/058,431 (Pereira et al., Jul. 13, 2021, "Systems and Methods for Treating Aneurysms") discloses an inverted mesh tube having an outer layer and an inner layer, wherein the outer layer transitions to the inner layer at an inversion fold located at or adjacent to the distal end of the occlusion element. U.S. patent application 20170258473 (Plaza et al., Sep. 14, 2017, "Systems and Methods for Delivery of Stents and Stent-Like Devices") discloses an elongate tubular member having a lumen, an expandable stent, and a delivery device which is placed in a cerebral vessel adjacent to an aneurysm.

U.S. patent applications 20060155323 (Porter et al., Jul. 13, 2006, "Intra-Aneurysm Devices") and 20190298379 (Porter et al., Oct. 3, 2019, "Intra-Aneurysm Devices") and also U.S. patent Ser. No. 10/265,075 (Porter et al., Apr. 23, 2019, "Intra-Aneurysm Devices") disclose an occlusive device having a neck and a dome. U.S. patent application 20210052279 (Porter et al., Feb. 25, 2021, "Intra-Aneurysm Devices") discloses a device including an upper member that sits against the dome of an aneurysm, a lower member that sits in the neck of the aneurysm, and a means of adjusting the overall dimensions of the device. U.S. patent application 20210128165 (Pulugurtha et al., May 6, 2021, "Systems and Methods for Treating Aneurysms") and U.S. patent Ser. No. 11/305,387 (Pulugurtha et al., Apr. 19, 2022, "Systems and Methods for Treating Aneurysms") disclose a distal conduit coupled to an occlusive member with a first lumen extending therethrough and a proximal conduit with a second lumen extending therethrough.

U.S. patent application 20220039804 (Rangwala et al., Feb. 10, 2022, "Flow-Diverting Implant and Delivery Method") discloses a saddle-shaped braided mesh diverter that covers the neck of an aneurysm. U.S. patent Ser. No. 11/559,309 (Rangwala et al., Jan. 24, 2023, "Filamentary Devices for Treatment of Vascular Defects") discloses a permeable implant whose proximal portion is stiffer. U.S. patent application 20230277184 (Rashidi et al., Sep. 7, 2023, "Occlusive Devices with Thrombogenic Inserts") discloses an expandable mesh which spans a neck of the aneurysm with an insert configured to promote thrombosis.

U.S. patent application 20170079662 (Rhee et al., Mar. 23, 2017, "Occlusive Devices") discloses an implant with a frame and a mesh component, wherein the mesh component has a first porosity and the frame has a second porosity. U.S. patent Ser. No. 10/478,194 (Rhee et al., Nov. 19, 2019, "Occlusive Devices") and U.S. patent application 20200038032 (Rhee et al., Feb. 6, 2020, "Occlusive Devices") disclose an implant with a frame and a mesh component, wherein the mesh component has a first porosity and the frame has a second porosity. U.S. patent application 20210128162 (Rhee et al., May 6, 2021, "Devices, Systems, and Methods for Treatment of Intracranial Aneurysms") discloses introduction of an embolic element to a space between an occlusive member and an inner surface of the aneurysm wall.

U.S. patent application 20140330299 (Rosenbluth et al., Nov. 6, 2014, "Embolic Occlusion Device and Method"), U.S. patent application 20180303486 (Rosenbluth et al., Oct. 25, 2018, "Embolic Occlusion Device and Method"), and U.S. patent application 20210259699 (Rosenbluth et al., Aug. 26, 2021, "Embolic Occlusion Device and Method") disclose an occlusion device with a tubular braided member having a first end and a second end and extending along a longitudinal axis, the tubular braided member having a repeating pattern of larger diameter portions and smaller diameter portions arrayed along the longitudinal axis. U.S. patent applications 20160022445 (Ruvalcaba et al., Jan. 28, 2016, "Occlusive Device") and 20190343664 (Ruvalcaba et al., Nov. 14, 2019, "Occlusive Device") U.S. patent Ser. No. 11/389,309 (Ruvalcaba et al., Jul. 19, 2022, "Occlusive Device") disclose an aneurysm embolization device having a single, continuous piece of material that is shape set into a plurality of distinct structural components.

U.S. patent application 20020169473 (Sepetka et al., Nov. 14, 2002, "Devices and Methods for Treating Vascular Malformations") discloses a device with a primary coil to provide structural integrity and secondary windings to fill interstitial spaces. U.S. patent application 20080281350 (Sepetka et al., Nov. 13, 2008, "Aneurysm Occlusion Devices") discloses an implantable occlusion device with a concave or cup-shaped shape after implantation. U.S. Pat. No. 8,597,320 (Sepetka et al., Dec. 3, 2013, "Devices and Methods for Treating Vascular Malformations") discloses a method of filling an aneurysm by advancing a device with a proximal collar and a distal collar through a vascular system and then positioning the device within an aneurysm. U.S. patent application 20140200607 (Sepetka et al., Jul. 17, 2014, "Occlusive Device"), U.S. patent application 20190274691 (Sepetka et al., Sep. 12, 2019, "Occlusive Device"), and U.S. patent Ser. No. 11/045,203 (Sepetka et al., Jun. 29, 2021, "Occlusive Device") disclose multiple sequentially deployed occlusive devices that are connected together to create an extended length. U.S. patent application 20210282784 (Sepetka et al., Sep. 16, 2021, "Occlusive Device") discloses a device comprising a plurality of braided wires and an embolic coil.

U.S. patent application 20170224350 (Shimizu et al., Aug. 10, 2017, "Devices for Vascular Occlusion"), U.S. patent Ser. No. 10/729,447 (Shimizu et al., Aug. 4, 2020, "Devices for Vascular Occlusion"), U.S. patent application 20200323534 (Shimizu et al., Oct. 15, 2020, "Devices for Vascular Occlusion"), U.S. patent Ser. No. 10/980,545 (Bowman et al., Apr. 20, 2021, "Devices for Vascular Occlusion"), U.S. patent application 20210228214 (Bowman et al., Jul. 29, 2021, "Devices for Vascular Occlusion"), and U.S. patent application 20210228214 (Bowman et al., Jul. 29, 2021, "Devices for Vascular Occlusion") disclose an occlusive device, an occlusive device delivery system, method of using, method of delivering an occlusive device, and method of making an occlusive device to treat various intravascular conditions. U.S. patent application 20230031965 (Sivapatham, Feb. 2, 2023, "Intrasaccular Stent Device for Aneurysm Treatment") discloses a system for treating an aneurysm in a blood vessel comprising a catheter, a guidewire, a delivery wire, an intrasaccular stent/retaining device removably attached to the delivery wire, and endovascular coiling.

U.S. patent application 20200305886 (Soto Del Valle et al, Oct. 1, 2020, "Aneurysm Treatment Device") and U.S. patent application 20220225997 (Soto Del Valle et al., Jul. 21, 2022, "Aneurysm Treatment Device") disclose a device with an expandable sack with a free open end and an elongated looping portion. U.S. patent application 20200305885 (Soto Del Valle et al, Oct. 1, 2020, "Aneurysm Treatment Device") discloses an occlusion device that expands to form a cup shape within an aneurysm sac. U.S. patent application 20200375607 (Soto Del Valle et al., Dec. 3, 2020, "Aneurysm Device and Delivery System") discloses a method of expanding mesh segments to form an outer occlusive sack and an inner occlusive sack. U.S. patent Ser. No. 11/337,706 (Soto Del Valle et al., May 24, 2022, "Aneurysm Treatment Device") discloses an implant having an elongated portion and an expandable braided sack portion.

U.S. patent application 20210282789 (Vu et al., Sep. 16, 2021, "Multiple Layer Devices for Treatment of Vascular Defects") discloses a first permeable shell and a second permeable shell, where the second permeable shell sits within an interior cavity of the first permeable shell. U.S. patent application 20220175389 (Wallace et al., Jun. 9, 2022, "Vaso-Occlusive Devices Including a Friction Element") discloses a vaso-occlusive implant with a friction element between a soft braided member and a coil. U.S. patent application 20200187952 (Walsh et al., Jun. 18, 2020, "Intrasaccular Flow Diverter for Treating Cerebral Aneurysms") and U.S. patent application 20220151632 (Walsh et al., May 19, 2022, "Intrasaccular Flow Diverter for Treating Cerebral Aneurysms") disclose a stabilizing frame with two parts, the first part sized to anchor within the sac of the aneurysm and the exterior part sized to anchor against a region of the blood vessel wall adjacent the aneurysm neck.

U.S. patent application 20200029973 (Walzman, Jan. 30, 2020, "Mash Cap for Ameliorating Outpouchings") discloses an embolic device comprising a control element, a catheter element, a delivery microcatheter hypotube, a detachment element, a mesh disc, a distal opening, and at least one attached extension arm. U.S. patent application 20200405347 (Walzman, Dec. 31, 2020, "Mesh Cap for Ameliorating Outpouchings") discloses a self-expandable occluding device which covers the neck of an outpouching and serves as a permanent embolic plug. U.S. patent Ser. No. 10/398,441 (Warner et al., Sep. 3, 2019, "Vascular Occlusion") discloses a vascular treatment system with a containment device, a pusher, and a stopper ring. U.S. patent Ser. No. 11/166,731 (Wolfe et al., Nov. 9, 2021, "Systems and Methods for Treating Aneurysms") discloses an inverted mesh tube having an outer layer and an inner layer, the outer layer transitioning to the inner layer at an inversion fold.

U.S. patent application 20200367906 (Xu et al., Nov. 26, 2020, "Aneurysm Treatment With Pushable Ball Segment") and U.S. patent application 20230016312 (Xu et al., Jan. 19, 2023, "Aneurysm Treatment with Pushable Implanted Braid") disclose a braided implant with a retractable dual proximal layer. U.S. patent application 20220087681 (Xu et al., Mar. 24, 2022, "Inverting Braided Aneurysm Implant with Dome Feature") discloses an implant with a dome feature configured to press into aneurysm walls near the aneurysm's dome and facilitate securement of the braid across the aneurysm's neck. U.S. patent Ser. No. 11/497,504 (Xu et al., Nov. 15, 2022, "Aneurysm Treatment with Pushable Implanted Braid") discloses a braided implant with a retractable dual proximal layer. U.S. patent Ser. No. 11/596,412 (Xu et al., Mar. 7, 2023, "Aneurysm Device and Delivery System") discloses a braid with a proximal portion which goes across an aneurysm neck and an expandable distal portion. U.S. patent application 20230061363 (Yee et al., Mar. 2, 2023, "Embolic Device with Improved Neck Coverage") discloses an embolic device with a flexible structure which has a series of alternating narrow portions and link portions.

U.S. patent application 20200367896 (Zaidat et al., Nov. 26, 2020, "Systems and Methods for Treating Aneurysms") discloses an apparatus for treating an aneurysm in a blood vessel with a first tubular mesh having a first end and a second end coupled together at a proximal end of the occlusion element. U.S. patent Ser. No. 11/202,636 (Zaidat et al., Dec. 21, 2021, "Systems and Methods for Treating Aneurysms"), U.S. patent application 20220022884 (Wolfe et al., Jan. 27, 2022, "Systems and Methods for Treating Aneurysms"), and U.S. patent application 20220211383 (Pereira et al., Jul. 7, 2022, "Systems and Methods for Treating Aneurysms") disclose an apparatus for treating an aneurysm including an occlusion element configured to be releasably coupled to an elongate delivery shaft and a distal end, a proximal end, and a longitudinal axis extending between the distal end and the proximal end. U.S. patent application 20220054141 (Zaidat et al., Feb. 24, 2022, "Systems and Methods for Treating Aneurysms") discloses an apparatus for treating an aneurysm in a blood vessel with a first tubular mesh having a first end and a second end coupled together at a proximal end of the occlusion element.

SUMMARY OF THE INVENTION

This invention can be embodied in a method and device for therapeutically-occluding a cerebral aneurysm. A method embodiment comprises forming and expanding a two-part intrasacular device for treating a cerebral aneurysm. In an example, the first step of the method can be radially-constraining a tubular mesh, thereby forming a proximal convex portion of the mesh and a distal convex portion of the mesh. The next step can be collapsing the proximal portion into a concave (e.g. bowl) shape, wherein the distal portion of the mesh is nested within the concavity of the proximal portion of the mesh. A last step can be expanding the distal portion of the mesh within an aneurysm sac by filling it with embolic members and/or material.

The expanded distal portion of the mesh holds the bowl-shaped proximal portion securely against the aneurysm neck and conforms to the wall contours of even an irregularly-shaped aneurysm sac. In these respects, this device can be more effective at aneurysm occlusion than prior art comprising either a bowl-shaped intrasacular mesh alone or a globular-shaped intrasacular mesh alone.

BRIEF INTRODUCTION TO THE FIGURES

FIG. 1 shows a seven-step method for treating a cerebral aneurysm, including forming a two-part mesh and expanding a distal portion of that mesh within the aneurysm sac.

DETAILED DESCRIPTION OF THE FIGURES

Figure 2:
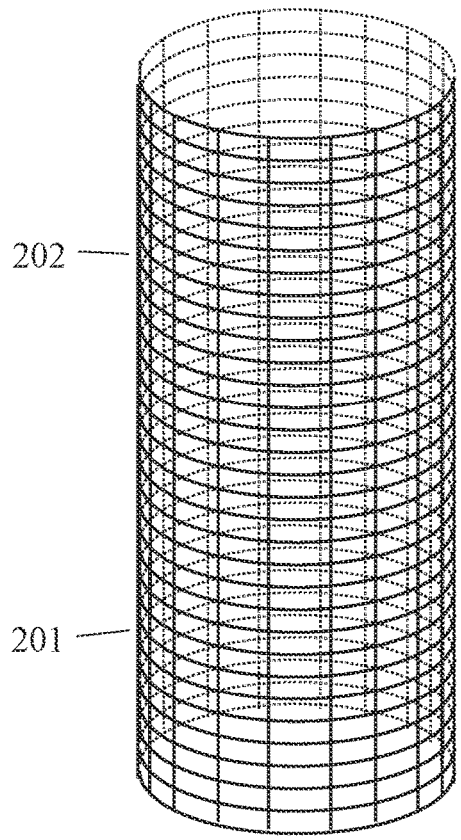
FIGS. 2-5 show four sequential views of a mesh device for treating a cerebral aneurysm, including forming that device from a tubular mesh and expanding of a distal portion of that device within the aneurysm sac.

FIGS. 1-13 show methods and devices for therapeutic occlusion of a cerebral aneurysm with an intrasacular two-part mesh. A proximal portion of the mesh covers the aneurysm neck from inside the aneurysm sac. A distal portion of the mesh is expanded by being filled with embolic members and/or material in order to fill the sac even an irregularly-shaped aneurysm. Some of these figures illustrate methods for forming this device from a tubular mesh. Some of these figures show the structure and components of devices. Before discussing the specific examples shown in these figures, it is useful to provide an introductory discussion of key concepts and components of the method and device embodiments of this invention. The key concepts and components provided in the following introductory section can be applied where relevant to the examples shown later in the figures.

In an example, a method for treating a cerebral aneurysm can comprise: forming a longitudinal tubular mesh, wherein the mesh has a proximal end, a distal end, a longitudinal axis between the proximal end and the distal end, and radial cross-sections which are orthogonal to the longitudinal axis; radially-constraining the proximal end and the distal end of the mesh; dividing the mesh into a convex proximal portion of the mesh and a convex distal portion by radially-constraining a middle location on the mesh, wherein the middle location is somewhere between the proximal and distal ends; collapsing the proximal portion onto itself by moving the middle location and the proximal end of the mesh closer together; delivering the mesh through a catheter to a cerebral aneurysm; inserting the mesh into the sac of the aneurysm, wherein the distal end of the mesh is closer to the dome of the aneurysm sac than the proximal end of the mesh, and wherein the proximal end of the mesh is closer to the neck of the aneurysm than the distal end of the mesh; and expanding the distal portion by inserting embolic members and/or embolic material into the distal portion.

In an example, a method for treating a cerebral aneurysm can comprise: forming a longitudinal tubular mesh, wherein the mesh has a proximal end, a distal end, a longitudinal axis between the proximal end and the distal end, and radial cross-sections which are orthogonal to the longitudinal axis; radially-constraining the proximal end and the distal end of the mesh; dividing the mesh into a convex proximal portion of the mesh and a convex distal portion by radially-constraining a middle location on the mesh, wherein the middle location is somewhere between the proximal and distal ends; delivering the mesh through a catheter to a cerebral aneurysm; inserting the mesh into the sac of the aneurysm, wherein the distal end of the mesh is closer to the dome of the aneurysm sac than the proximal end of the mesh, and wherein the proximal end of the mesh is closer to the neck of the aneurysm than the distal end of the mesh; collapsing the proximal portion onto itself by moving the middle location and the proximal end of the mesh closer together; and expanding the distal portion by inserting embolic members and/or embolic material into the distal portion.

In an example, a method for treating a cerebral aneurysm can comprise: forming a longitudinal tubular mesh, wherein the mesh has a proximal end, a distal end, a longitudinal axis between the proximal end and the distal end, and radial cross-sections which are orthogonal to the longitudinal axis; radially-constraining the proximal end and the distal end of the mesh; dividing the mesh into a convex proximal portion of the mesh and a convex distal portion by radially-constraining a middle location on the mesh, wherein the middle location is somewhere between the proximal and distal ends; collapsing the proximal portion onto itself by moving the middle location and the proximal end of the mesh closer together; delivering the mesh through a catheter to a cerebral aneurysm; and inserting the mesh into the sac of the aneurysm, wherein the distal end of the mesh is closer to the dome of the aneurysm sac than the proximal end of the mesh, and wherein the proximal end of the mesh is closer to the neck of the aneurysm than the distal end of the mesh.

In an example, a method for treating a cerebral aneurysm can comprise: radially-constraining a proximal end and a distal end of a longitudinal tubular mesh, wherein the mesh has a longitudinal axis between the proximal end and the distal end, and radial cross-sections which are orthogonal to the longitudinal axis; dividing the mesh into a convex proximal portion of the mesh and a convex distal portion by radially-constraining a middle location on the mesh, wherein the middle location is somewhere between the proximal and distal ends; collapsing the proximal portion onto itself by moving the middle location and the proximal end of the mesh closer together; delivering the mesh through a catheter to a cerebral aneurysm; inserting the mesh into the sac of the aneurysm, wherein the distal end of the mesh is closer to the dome of the aneurysm sac than the proximal end of the mesh, and wherein the proximal end of the mesh is closer to the neck of the aneurysm than the distal end of the mesh; and expanding the distal portion by inserting embolic members and/or embolic material into the distal portion.

In an example, a method for treating a cerebral aneurysm can comprise: forming a longitudinal tubular mesh, wherein the mesh has a proximal end, a distal end, a longitudinal axis between the proximal end and the distal end, and radial cross-sections which are orthogonal to the longitudinal axis; radially-constraining the proximal end and the distal end of the mesh; dividing the mesh into a convex proximal portion of the mesh and a convex distal portion by radially-constraining a middle location on the mesh, wherein the middle location is somewhere between the proximal and distal ends; collapsing the proximal portion onto itself by moving the middle location and the proximal end of the mesh closer together; delivering the mesh through a catheter to a cerebral aneurysm; inserting the mesh into the sac of the aneurysm, wherein the distal end of the mesh is closer to the dome of the aneurysm sac than the proximal end of the mesh, and wherein the proximal end of the mesh is closer to the neck of the aneurysm than the distal end of the mesh; and inserting embolic members and/or embolic material into the distal portion.

In an example, a method for treating a cerebral aneurysm can comprise: forming a tubular mesh; radially-constraining a proximal end and a distal end of the mesh; dividing the mesh into a proximal portion of the mesh and a distal portion by radially-constraining a middle location on the mesh, wherein the middle location is somewhere between the proximal and distal ends; collapsing the proximal portion onto itself in a proximal direction; delivering the mesh through a catheter to a cerebral aneurysm; inserting the mesh into the sac of the aneurysm; and expanding the distal portion by inserting embolic members and/or embolic material into the distal portion.

In an example, a method for treating a cerebral aneurysm can comprise: forming a tubular mesh; radially-constraining a proximal end and a distal end of the mesh; dividing the mesh into a proximal portion of the mesh and a distal portion by radially-constraining a middle location on the mesh, wherein the middle location is somewhere between the proximal and distal ends; collapsing the proximal portion; delivering the mesh through a catheter to a cerebral aneurysm; inserting the mesh into the sac of the aneurysm; and inserting embolic members and/or embolic material into the distal portion.

In an example, a method for treating a cerebral aneurysm can comprise: radially-constraining a proximal end and a distal end of a tubular mesh; dividing the mesh into a proximal portion of the mesh and a distal portion by radially-constraining a middle location on the mesh, wherein the middle location is somewhere between the proximal and distal ends; collapsing the proximal portion; delivering the mesh through a catheter to a cerebral aneurysm; and inserting the mesh into the sac of the aneurysm.

In an example, a method for treating a cerebral aneurysm can comprise: closing a proximal end and a distal end of a tubular mesh; dividing the mesh into a proximal portion and a distal portion by radially-constraining a middle location on the mesh, wherein the middle location is somewhere between the proximal and distal ends; collapsing the proximal portion; delivering the mesh through a catheter to a cerebral aneurysm; and inserting the mesh into the sac of the aneurysm.

In an example, a device for treating a cerebral aneurysm can comprise: a proximal portion and a distal portion of a longitudinal mesh; a proximal annular member which radially-constrains the proximal end of the mesh; a distal annular member which radially-constrains the distal end of the mesh; a middle annular member which radially-constrains a middle location of the mesh, wherein the middle location is somewhere between the proximal and distal ends of the mesh; and embolic members and/or embolic material which is inserted into the distal portion of the mesh, wherein the mesh is configured to be inserted into an aneurysm sac, and wherein insertion of the embolic members and/or embolic material expands the distal portion of the mesh to conform to the walls of even an irregularly-shaped aneurysm sac.

In an example, a device for treating a cerebral aneurysm can comprise: a concave (e.g. bowl-shaped) proximal portion and a convex (e.g. globular) distal portion of a longitudinal mesh; a proximal annular member (e.g. ring, band, or cylinder) which radially-constrains the proximal end of the mesh; a distal annular member (e.g. ring, band, or cylinder) which radially-constrains the distal end of the mesh; a middle annular member (e.g. ring, band, or cylinder) which radially-constrains a middle location of the mesh, wherein the middle location is somewhere between the proximal and distal ends of the mesh; and embolic members and/or embolic material which is inserted into the distal portion of the mesh, wherein the mesh is configured to be inserted into an aneurysm sac, and wherein insertion of the embolic members and/or embolic material expands the distal portion of the mesh to conform to the walls of even an irregularly-shaped aneurysm sac.

In an example, a device for treating a cerebral aneurysm can comprise: a concave (e.g. bowl-shaped and/or hemispherical) proximal portion of a mesh; a convex (e.g. ball-shaped and/or spherical) distal portion of the mesh which is nested within the concavity of the proximal portion; a proximal annular member (e.g. ring, band, or cylinder) which radially-constrains the proximal end of the mesh; a distal annular member (e.g. ring, band, or cylinder) which radially-constrains the distal end of the mesh; a middle annular member (e.g. ring, band, or cylinder) which radially-constrains a middle location of the mesh between the proximal portion and the distal portion; and embolic members and/or embolic material which is inserted into the distal portion of the mesh, wherein the mesh is configured to be inserted into an aneurysm sac, and wherein insertion of the embolic members and/or embolic material expands the distal portion of the mesh to conform to the walls of even an irregularly-shaped aneurysm sac.

In an example, a method for treating a cerebral aneurysm can comprise forming a longitudinal tubular mesh, wherein the mesh has a proximal end, a distal end, a longitudinal axis between the proximal end and the distal end, and radial cross-sections which are orthogonal to the longitudinal axis. In an example, a method can comprise forming a tubular mesh comprising an orthogonal array of longitudinal and circular wires, tubes, or strands. In an example, a method can comprise forming a tubular mesh which is made entirely from the same material. In an example, a method can comprise forming a tubular mesh whose durometer level decreases with distance from its proximal end.

In an example, a method can comprise forming a honeycomb tubular mesh with hexagonal openings and/or holes. In an example, a method can comprise forming a tubular mesh whose proximal portion is made from a metal and whose distal portion is made from a polymer. In an example, a method can comprise forming a tubular mesh whose density decreases with distance from its proximal end. In an example, a method can comprise forming a tubular mesh by electroforming. In an example, a method can comprise forming a tubular mesh whose proximal portion is made from a first mix of metal and polymer components and whose distal portion is made from a second mix of metal and polymer components, wherein the second mix has a lower percentage of polymers than the first mix. In an example, a method can comprise forming a tubular mesh with uniform elasticity. In an example, a method can comprise forming a tubular mesh by sheet cutting.

In an example, a method can comprise forming a tubular mesh whose proximal portion is made from a first material and whose distal portion is made from a second material, wherein the second material is less elastic than the first material. In an example, a method can comprise forming a tubular mesh with uniform density. In an example, a method can comprise forming a tubular mesh from wires, tubes, or strands with different diameters. In an example, a method can comprise forming a tubular mesh whose proximal portion has openings or pores with a first average size and whose distal portion has openings or pores with a second average size, wherein the second average size is less than the first average size.

In an example, a method can comprise forming a tubular mesh with a tapered and/or frustal shape. In an example, a method can comprise forming a tubular mesh from polymer strands. In an example, a method can comprise forming a tubular mesh whose cross-sectional size increases with distance from its proximal end. In an example, a method can comprise forming a tubular mesh with hexagonal openings and/or holes. In an example, a method can comprise forming a tubular mesh from gold.

In an example, a method can comprise forming a tubular mesh whose porosity increases with distance from its proximal end. In an example, a method can comprise forming a tubular mesh with hexagonal openings and/or holes between braided or woven wires, tubes, or strands. In an example, a method can comprise forming a tubular mesh from silk. In an example, a method can comprise forming a tubular mesh whose thickness increases with distance from its proximal end. In an example, a method can comprise forming a tubular mesh from cellulose. In an example, a method can comprise forming a tubular mesh whose elasticity decreases with distance from its proximal end. In an example, a method can comprise forming a tubular mesh comprising longitudinal wires, tubes, or strands and circular wires, tubes, or strands.

In an example, a method can comprise forming a tubular mesh whose proximal portion is made from wires, tubes, or strands with a first average diameter and whose distal portion is made from wires, tubes, or strands with a second average diameter. In an example, a method can comprise forming a tubular mesh whose durometer level increases with distance from its proximal end.

In an example, a method can comprise forming a honeycomb tubular mesh with hexagonal openings and/or holes between braided or woven wires, tubes, or strands. In an example, a method can comprise forming a tubular mesh whose distal portion is made from a metal and whose proximal portion is made from a polymer. In an example, a method can comprise forming a tubular mesh whose length (e.g. longitudinal axis) is between 1.5 and 2.5 times its width (e.g. cross-sectional diameter). In an example, a method can comprise forming a tubular mesh by extrusion. In an example, a method can comprise forming a tubular mesh whose proximal portion is made from a first material and whose distal portion is made from a second material.

In an example, a method can comprise forming a tubular mesh with uniform porosity. In an example, a method can comprise forming a tubular mesh by weaving. In an example, a method can comprise forming a tubular mesh whose proximal portion is made from a first material and whose distal portion is made from a second material, wherein the second material has a higher durometer level than the first material. In an example, a method can comprise forming a tubular mesh with a single layer. In an example, a method can comprise forming a tubular mesh from helical wires, tubes, or strands. In an example, a method can comprise forming a tubular mesh whose proximal portion has a first weave density and whose distal portion has a second weave density.

In an example, a method can comprise forming a tubular mesh with quadrilateral openings and/or holes. In an example, a method can comprise forming a tubular mesh from polymer yarns or threads. In an example, a method can comprise forming a tubular mesh whose cross-sectional size decreases with distance from its proximal end. In an example, a method can comprise forming a tubular mesh with quadrilateral openings and/or holes between braided or woven wires, tubes, or strands.

In an example, a method can comprise forming a tubular mesh from tungsten. In an example, a method can comprise forming a tubular mesh whose porosity decreases with distance from its proximal end. In an example, a method can comprise forming a tubular mesh with helical wires, tubes, or strands. In an example, a method can comprise forming a tubular mesh from PDMS. In an example, a method can comprise forming a tubular mesh whose thickness decreases with distance from its proximal end. In an example, a method can comprise forming a tubular mesh from chitin. In an example, a method can comprise forming a tubular mesh whose elasticity increases with distance from its proximal end.

In an example, a method can comprise forming a tubular mesh comprising longitudinal wires, tubes, or strands and helical wires, tubes, or strands. In an example, a method can comprise forming a tubular mesh whose proximal portion is made from wires, tubes, or strands with a first average diameter and whose distal portion is made from wires, tubes, or strands with a second average diameter, wherein the second average diameter is greater than the first average diameter.

In an example, a method can comprise forming a tubular mesh whose thickness decreases with distance from its proximal end. In an example, a method can comprise forming a tubular mesh by 3D printing. In an example, a method can comprise forming a tubular mesh whose proximal portion is made from a first mix of metal and polymer components and whose distal portion is made from a second mix of metal and polymer components. In an example, a method can comprise forming a tubular mesh whose length (e.g. longitudinal axis) is between 2.5 and 3.5 times its width (e.g. cross-sectional diameter). In an example, a method can comprise forming a tubular mesh by knitting.

In an example, a method can comprise forming a tubular mesh whose proximal portion is made from a first material and whose distal portion is made from a second material, wherein the second material is more elastic than the first material. In an example, a method can comprise forming a tubular mesh with uniform a durometer level. In an example, a method can comprise forming a tubular mesh by welding. In an example, a method can comprise forming a tubular mesh whose proximal portion has openings or pores with a first average size and whose distal portion has openings or pores with a second average size.

In an example, a method can comprise forming a tubular mesh with two or more layers. In an example, a method can comprise forming a tubular mesh from metal wires. In an example, a method can comprise forming a tubular mesh whose proximal portion has a first weave density and whose distal portion has a second weave density, wherein the second weave density is greater than the first weave density. In an example, a method can comprise forming a tubular mesh with square openings and/or holes. In an example, a method can comprise forming a tubular mesh from nitinol. In an example, a method can comprise forming a tubular mesh whose elasticity increases with distance from its proximal end. In an example, a method can comprise forming a tubular mesh with square openings and/or holes between braided or woven wires, tubes, or strands.

In an example, a method can comprise forming a tubular mesh from nickel. In an example, a method can comprise forming a tubular mesh whose durometer level increases with distance from its proximal end. In an example, a method can comprise forming a tubular mesh with a circular cross-sectional shape. In an example, a method can comprise forming a tubular mesh from silicone.

In an example, a method can comprise forming a tubular mesh whose density increases with distance from its proximal end. In an example, a method can comprise forming a tubular mesh from collagen. In an example, a method can comprise forming a tubular mesh whose porosity decreases with distance from its proximal end. In an example, a method can comprise forming a tubular mesh comprising helical wires, tubes, or strands and circular wires, tubes, or strands. In an example, a method can comprise forming a tubular mesh whose proximal portion is made from wires, tubes, or strands with a first average diameter and whose distal portion is made from wires, tubes, or strands with a second average diameter, wherein the second average diameter is less than the first average diameter.

In an example, a method can comprise forming a tubular mesh whose thickness increases with distance from its proximal end. In an example, a method can comprise forming a tubular mesh by braiding. In an example, a method can comprise forming a tubular mesh whose proximal portion is made from a first mix of metal and polymer components and whose distal portion is made from a second mix of metal and polymer components, wherein the second mix has a greater percentage of polymers than the first mix.

In an example, a method can comprise forming a tubular mesh with a uniform cross-sectional size. In an example, a method can comprise forming a tubular mesh by laser cutting. In an example, a method can comprise forming a tubular mesh whose proximal portion is made from a first material and whose distal portion is made from a second material, wherein the second material has a lower durometer level than the first material. In an example, a method can comprise forming a tubular mesh with uniform thickness.

In an example, a method can comprise forming a tubular mesh from wires, tubes, or strands with a uniform diameter. In an example, a method can comprise forming a tubular mesh whose proximal portion has openings or pores with a first average size and whose distal portion has openings or pores with a second average size, wherein the second average size is greater than the first average size. In an example, a method can comprise forming a tubular mesh with a columnar shape. In an example, a method can comprise forming a tubular mesh from metal tubes. In an example, a method can comprise forming a tubular mesh whose proximal portion has a first weave density and whose distal portion has a second weave density, wherein the second weave density is less than the first weave density.

In an example, a method can comprise forming a tubular mesh with triangular openings and/or holes. In an example, a method can comprise forming a tubular mesh from platinum. In an example, a method can comprise forming a tubular mesh whose elasticity decreases with distance from its proximal end. In an example, a method can comprise forming a tubular mesh with triangular openings and/or holes between braided or woven wires, tubes, or strands. In an example, a method can comprise forming a tubular mesh from Dacron. In an example, a method can comprise forming a tubular mesh whose durometer level decreases with distance from its proximal end.

In an example, a method can comprise forming a tubular mesh with an oval or elliptical circular cross-sectional shape. In an example, a method can comprise forming a tubular mesh from carboxy methyl cellulose. In an example, a method can comprise forming a tubular mesh whose density decreases with distance from its proximal end. In an example, a method can comprise forming a tubular mesh from polyetherether ketone. In an example, a method can comprise forming a tubular mesh whose porosity increases with distance from its proximal end.

In an example, a method for treating a cerebral aneurysm can comprise radially-constraining the proximal end and the distal end of the mesh. In an example, a method can comprise (separately) closing both ends of a tubular mesh. In an example, a method can comprise (separately) tying both ends of a tubular mesh. In an example, a method can comprise inverting the distal end of a tubular mesh, wherein the length of the inverted portion is less than 33% of the length of the entire mesh before inversion. In an example, a method can comprise inverting the distal end of a tubular into the mesh in a proximal direction and then radially-constraining that end.

In an example, a method can comprise inverting the proximal end of a tubular mesh, wherein the length of the inverted portion is less than 33% of the length of the entire mesh before inversion. In an example, a method can comprise inverting the proximal end of a tubular into the mesh in a distal direction and then radially-constraining that end. In an example, a method can comprise placing an inner cylindrical member inside a tubular mesh at a given location and placing an outer cylindrical member around the tubular mesh at that location, wherein the inner cylindrical member keeps a passage open within the mesh at that location and the outer cylindrical member radially-constrains the mesh at that location, and wherein the inner cylindrical member and the outer cylindrical member are coaxial.

In an example, a method can comprise radially-constraining (e.g. binding or closing) the proximal end of a tubular mesh with an annular member. In an example, a method can comprise radially-constraining (e.g. binding or closing) the proximal end of a tubular mesh with a metal band. In an example, a method can comprise radially-constraining (e.g. binding or closing) the proximal end of a tubular mesh with a filament or strand. In an example, a method can comprise radially-constraining (e.g. binding or closing) the distal end of a tubular mesh with a ring.

In an example, a method can comprise radially-constraining (e.g. binding or closing) the distal end of a tubular mesh with an elastic band. In an example, a method can comprise radially-constraining (e.g. binding or closing) the distal end of a tubular mesh with a cylinder. In an example, a method can comprise radially-constraining a tubular mesh with a ring around a location on the longitudinal axis of the mesh. In an example, a method can comprise radially-constraining a tubular mesh with an elastic band around a location on the longitudinal axis of the mesh. In an example, a method can comprise radially-constraining a tubular mesh with a cylinder around a location on the longitudinal axis of the mesh.

In an example, a method can comprise radially-constraining and inverting the proximal end of a tubular mesh with a band. In an example, a method can comprise radially-constraining and inverting the proximal end of a tubular mesh with a wire which is wound. In an example, a method can comprise radially-constraining and inverting the distal end of a tubular mesh with an annular member. In an example, a method can comprise radially-constraining and inverting the distal end of a tubular mesh with a metal band. In an example, a method can comprise radially-constraining and inverting the distal end of a tubular mesh with a filament or strand. In an example, a method can comprise radially-constraining the proximal end of a tubular mesh and then inverting that end into the mesh in a distal direction.

In an example, a method can comprise (separately) crimping shut both ends of a tubular mesh. In an example, a method can comprise inverting the distal end of a tubular mesh. In an example, a method can comprise inverting the distal end of a tubular mesh, wherein the length of the inverted portion is less than 25% of the length of the entire mesh before inversion. In an example, a method can comprise inverting the proximal end of a tubular mesh. In an example, a method can comprise inverting the proximal end of a tubular mesh, wherein the length of the inverted portion is less than 25% of the length of the entire mesh before inversion.

In an example, a method can comprise placing an inner annular member inside a tubular mesh at a given location and placing an outer annular member around the tubular mesh at that location, wherein the inner annular member keeps a passage open within the mesh at that location and the outer annular member radially-constrains the mesh at that location. In an example, a method can comprise placing an inner cylindrical member inside a tubular mesh at a given location and placing an outer cylindrical member around the tubular mesh at that location, wherein the inner cylindrical member keeps a passage open within the mesh at that location and the outer cylindrical member radially-constrains the mesh at that location, and wherein the mesh is pinched or crimped between the inner cylindrical member and the outer cylindrical member. In an example, a method can comprise radially-constraining (e.g. binding or closing) the proximal end of a tubular mesh with a ring. In an example, a method can comprise radially-constraining (e.g. binding or closing) the proximal end of a tubular mesh with an elastic band.

In an example, a method can comprise radially-constraining (e.g. binding or closing) the proximal end of a tubular mesh with a cylinder. In an example, a method can comprise radially-constraining (e.g. binding or closing) the distal end of a tubular mesh with a band. In an example, a method can comprise radially-constraining (e.g. binding or closing) the distal end of a tubular mesh with a wire which is wound.

In an example, a method can comprise radially-constraining a tubular mesh with an outer annular member which goes around the outside the tubular mesh at a location, but keeping a pathway open within the tubular mesh at that location with an inner annular member. In an example, a method can comprise radially-constraining a tubular mesh with a band around a location on the longitudinal axis of the mesh. In an example, a method can comprise radially-constraining a tubular mesh with a wire which is wound around a location on the longitudinal axis of the mesh. In an example, a method can comprise radially-constraining and inverting the proximal end of a tubular mesh with an annular member.

In an example, a method can comprise radially-constraining and inverting the proximal end of a tubular mesh with a metal band. In an example, a method can comprise radially-constraining and inverting the proximal end of a tubular mesh with a filament or strand. In an example, a method can comprise radially-constraining and inverting the distal end of a tubular mesh with a ring. In an example, a method can comprise radially-constraining and inverting the distal end of a tubular mesh with an elastic band. In an example, a method can comprise radially-constraining and inverting the distal end of a tubular mesh with a cylinder. In an example, a method can comprise (separately) soldering or melting shut both ends of a tubular mesh.

In an example, a method can comprise inverting the distal end of a tubular mesh, wherein the length of the inverted portion is less than 50% of the length of the entire mesh before inversion. In an example, a method can comprise inverting the distal end of a tubular mesh, wherein the length of the inverted portion is less than 10% of the length of the entire mesh before inversion. In an example, a method can comprise inverting the proximal end of a tubular mesh, wherein the length of the inverted portion is less than 50% of the length of the entire mesh before inversion.

In an example, a method can comprise inverting the proximal end of a tubular mesh, wherein the length of the inverted portion is less than 10% of the length of the entire mesh before inversion. In an example, a method can comprise placing an inner annular member inside a tubular mesh at a given location and placing an outer annular member around the tubular mesh at that location, wherein the inner annular member keeps a passage open within the mesh at that location and the outer annular member radially-constrains the mesh at that location, and wherein the inner annular member and the outer annular member are coaxial.

In an example, a method can comprise placing an inner ring inside a tubular mesh at a given location and placing an outer ring around the tubular mesh at that location, wherein the inner ring keeps a passage open within the mesh at that location and the outer ring radially-constrains the mesh at that location, and wherein the mesh is pinched or crimped between the inner ring and the outer ring. In an example, a method can comprise radially-constraining (e.g. binding or closing) the proximal end of a tubular mesh with a band. In an example, a method can comprise radially-constraining (e.g. binding or closing) the proximal end of a tubular mesh with a wire which is wound.

In an example, a method can comprise radially-constraining (e.g. binding or closing) the distal end of a tubular mesh with an annular member. In an example, a method can comprise radially-constraining (e.g. binding or closing) the distal end of a tubular mesh with a metal band. In an example, a method can comprise radially-constraining (e.g. binding or closing) the distal end of a tubular mesh with a filament or strand. In an example, a method can comprise radially-constraining a tubular mesh with an annular member around a location on the longitudinal axis of the mesh.

In an example, a method can comprise radially-constraining a tubular mesh with a metal band around a location on the longitudinal axis of the mesh. In an example, a method can comprise radially-constraining a tubular mesh with a filament or strand around a location on the longitudinal axis of the mesh. In an example, a method can comprise radially-constraining and inverting the proximal end of a tubular mesh with a ring. In an example, a method can comprise radially-constraining and inverting the proximal end of a tubular mesh with an elastic band.

In an example, a method can comprise radially-constraining and inverting the proximal end of a tubular mesh with a cylinder. In an example, a method can comprise radially-constraining and inverting the distal end of a tubular mesh with a band. In an example, a method can comprise radially-constraining and inverting the distal end of a tubular mesh with a wire which is wound. In an example, a method can comprise radially-constraining the distal end of a tubular mesh and then inverting that end into the mesh in a proximal direction.

In an example, a method for treating a cerebral aneurysm can comprise dividing the mesh into a convex proximal portion of the mesh and a convex distal portion by radially-constraining a middle location on the mesh, wherein the middle location is somewhere between the proximal and distal ends. In an example, a method can comprise dividing a tubular mesh into a proximal portion and a distal portion by radially-constraining a middle location on the longitudinal axis of the mesh, wherein the middle location is midway between the proximal end of the mesh and the distal end of the mesh. In an example, a method can comprise dividing a tubular mesh into a proximal portion and a distal portion by radially-constraining a middle location on the longitudinal axis of the mesh, wherein the middle location is between 60% and 90% of the way from the proximal end of the mesh and the distal end of the mesh.

In an example, a method can comprise dividing a tubular mesh into a proximal and distal portion by radially-constraining a middle location on the longitudinal axis of the mesh, wherein the proximal portion is longer than the distal portion. In an example, a method can comprise dividing a tubular mesh into a proximal and distal portion by radially-constraining a middle location on the longitudinal axis of the mesh, wherein the proximal portion is wider than the distal portion.

In an example, a method can comprise placing an inner cylindrical member inside a tubular mesh at a middle location and placing an outer cylindrical member around the tubular mesh at that location, wherein the inner cylindrical member keeps a passage open within the mesh at that location and the outer cylindrical member radially-constrains the mesh at that location, and wherein the inner cylindrical member and the outer cylindrical member are coaxial. In an example, a method can comprise radially-constraining a middle location on a tubular mesh, wherein the radially-constrained portion has a diameter which is less than 10% of the diameter of the mesh before radial constraint.

In an example, a method can comprise radially-constraining a tubular mesh with an annular member around a middle location on the longitudinal axis of the mesh. In an example, a method can comprise radially-constraining a tubular mesh with an elastic band around a middle location on the longitudinal axis of the mesh. In an example, a method for treating a cerebral aneurysm can comprise dividing the mesh into a convex proximal portion of the mesh and a convex distal portion of the mesh, wherein the overall mesh has an hourglass shape after being radially constrained. In an example, a method for treating a cerebral aneurysm can comprise dividing the mesh into a convex proximal portion of the mesh and a convex distal portion of the mesh, wherein the proximal portion and the distal portion have globular shapes.

In an example, a method can comprise dividing a tubular mesh into a proximal portion and a distal portion by radially-constraining a middle location on the longitudinal axis of the mesh, wherein the middle location is between 20% and 40% of the way from the proximal end of the mesh and the distal end of the mesh. In an example, a method can comprise dividing a tubular mesh into a proximal portion and a distal portion by radially-constraining a middle location on the longitudinal axis of the mesh.

In an example, a method can comprise dividing a tubular mesh into a proximal and distal portion by radially-constraining a middle location on the longitudinal axis of the mesh, wherein the distal portion is longer than the proximal portion. In an example, a method can comprise dividing a tubular mesh into a proximal and distal portion by radially-constraining a middle location on the longitudinal axis of the mesh, wherein the distal portion is wider than the proximal portion. In an example, a method can comprise placing an inner cylindrical member inside a tubular mesh at a middle location and placing an outer cylindrical member around the tubular mesh at that location, wherein the inner cylindrical member keeps a passage open within the mesh at that location and the outer cylindrical member radially-constrains the mesh at that location, and wherein the mesh is pinched or crimped between the inner cylindrical member and the outer cylindrical member.

In an example, a method can comprise radially-constraining a middle location on a tubular mesh, wherein the radially-constrained portion has a diameter which is between 10% and 30% of the diameter of the mesh before radial constraint. In an example, a method can comprise radially-constraining a tubular mesh with a ring around a middle location on the longitudinal axis of the mesh. In an example, a method can comprise radially-constraining a tubular mesh with a wire which is wound around a middle location on the longitudinal axis of the mesh. In an example, a method for treating a cerebral aneurysm can comprise dividing the mesh into a convex proximal portion of the mesh and a convex distal portion of the mesh, wherein the overall mesh has a dumb-bell shape after being radially constrained.

In an example, a method for treating a cerebral aneurysm can comprise dividing the mesh into a convex proximal portion of the mesh and a convex distal portion of the mesh, wherein the convex proximal portion and the convex distal portion have spherical, oblate spherical, and/or ellipsoidal shapes. In an example, a method can comprise dividing a tubular mesh into a proximal portion and a distal portion by radially-constraining a middle location on the longitudinal axis of the mesh, wherein the middle location is between 30% and 60% of the way from the proximal end of the mesh and the distal end of the mesh.

In an example, a method can comprise dividing a tubular mesh into a proximal and distal portion by radially-constraining a middle location on the longitudinal axis of the mesh, wherein the proximal and distal portions are the same length. In an example, a method can comprise dividing a tubular mesh into a proximal and distal portion by radially-constraining a middle location on the longitudinal axis of the mesh, wherein the proximal portion is larger than the distal portion. In an example, a method can comprise placing an inner annular member inside a tubular mesh at a middle location and placing an outer annular member around the tubular mesh at that location, wherein the inner annular member keeps a passage open within the mesh at that location and the outer annular member radially-constrains the mesh at that location.

In an example, a method can comprise placing an inner ring inside a tubular mesh at a middle location and placing an outer ring around the tubular mesh at that location, wherein the inner ring keeps a passage open within the mesh at that location and the outer ring radially-constrains the mesh at that location, and wherein the mesh is pinched or crimped between the inner ring and the outer ring. In an example, a method can comprise radially-constraining a middle location on a tubular mesh, wherein the radially-constrained portion has a diameter which is between 25% and 50% of the diameter of the mesh before radial constraint.

In an example, a method can comprise radially-constraining a tubular mesh with a band around a middle location on the longitudinal axis of the mesh. In an example, a method can comprise radially-constraining a tubular mesh with a filament or strand around a middle location on the longitudinal axis of the mesh. In an example, a method for treating a cerebral aneurysm can comprise dividing the mesh into a convex proximal portion of the mesh and a convex distal portion of the mesh, wherein the overall mesh has a figure eight shape after being radially constrained. In an example, a method can comprise dividing a tubular mesh into a proximal portion and a distal portion by radially-constraining a middle location on the longitudinal axis of the mesh, wherein the middle location is between 50% and 75% of the way from the proximal end of the mesh and the distal end of the mesh.

In an example, a method can comprise dividing a tubular mesh into a proximal and distal portion by radially-constraining a middle location on the longitudinal axis of the mesh, wherein the proximal and distal portions are the same size. In an example, a method can comprise dividing a tubular mesh into a proximal and distal portion by radially-constraining a middle location on the longitudinal axis of the mesh, wherein the distal portion is larger than the proximal portion. In an example, a method can comprise placing an inner annular member inside a tubular mesh at a middle location and placing an outer annular member around the tubular mesh at that location, wherein the inner annular member keeps a passage open within the mesh at that location and the outer annular member radially-constrains the mesh at that location, and wherein the inner annular member and the outer annular member are coaxial.

In an example, a method can comprise radially-constraining a middle location on a tubular mesh, but still keeping a longitudinal pathway at that location through which embolic members and/or embolic material can be inserted. In an example, a method can comprise radially-constraining a tubular mesh with an outer annular member which goes around the outside the tubular mesh at a middle location, but keeping a pathway open within the tubular mesh at that location with an inner annular member.

In an example, a method can comprise radially-constraining a tubular mesh with a metal band around a middle location on the longitudinal axis of the mesh. In an example, a method can comprise radially-constraining a tubular mesh with a cylinder around a middle location on the longitudinal axis of the mesh. In an example, a method for treating a cerebral aneurysm can comprise dividing the mesh into a convex proximal portion of the mesh and a convex distal portion of the mesh, wherein the overall mesh has a peanut shape after being radially constrained.

In an example, a method for treating a cerebral aneurysm can comprise collapsing the proximal portion of a mesh onto itself by moving a middle location of the mesh and a proximal end of the mesh closer together. In an example, a method for treating a cerebral aneurysm can comprise collapsing the proximal portion of a mesh onto itself by moving a middle location of the mesh toward the proximal end of the mesh.

In an example, a circumferential portion (e.g. ring) of the proximal portion can be weaker and/or more flexible than the rest of the proximal portion so that the proximal portion folds, bends, and/or inverts along this ring to create a bowl shape. In an example, a proximal portion of a mesh can be collapsed by inserting embolic members and/or material into the distal portion of the mesh. In an example, a proximal portion of a mesh can be collapsed by inserting congealing liquid embolic material into the distal portion of the mesh. In an example, a proximal portion of a mesh can be collapsed by moving (e.g. pulling or pushing) the middle location of the mesh toward the proximal end of the mesh.

In an example, a proximal portion of a mesh can be collapsed by moving (e.g. pulling or pushing) the distal part of the proximal portion and the proximal part of the proximal portion closer together. In an example, a proximal portion of a mesh can be collapsed by moving the middle location of the mesh and the proximal end of the mesh closer together by pulling or pushing a wire, string, or rod. In an example, a proximal portion of a mesh can be collapsed by moving (e.g. pulling or pushing) the distal part of the proximal portion and the proximal part of the proximal portion closer together by rotating a wire, rod, or helically-threaded member.

In an example, a proximal portion of a mesh can be collapsed into a bowl (e.g. hemispherical) shape by inserting congealing liquid embolic material into the distal portion of the mesh. In an example, a proximal portion of a mesh can be collapsed into a bowl (e.g. hemispherical) shape by inserting "string-of-pearls" longitudinal embolic strands into the distal portion of the mesh. In an example, a proximal portion of a mesh can be inverted (e.g. folded in on itself) by inserting embolic members and/or material into the distal portion of the mesh, wherein accumulation of the embolic members and/or material in the distal portion of the mesh inverts the proximal portion by exerting pressure on the proximal portion.

In an example, a proximal portion of a mesh can be inverted (e.g. folded in on itself) by inserting congealing liquid embolic material into the distal portion of the mesh, wherein accumulation of the congealing liquid embolic material in the distal portion of the mesh inverts the proximal portion by exerting pressure on the proximal portion. In an example, a proximal portion of a mesh can be inverted (e.g. folded in on itself) by moving (e.g. pulling or pushing) the middle location of the mesh and the proximal end of the mesh closer together.

In an example, a proximal portion of a mesh can be inverted (e.g. folded in on itself) by moving (e.g. pulling or pushing) the proximal part of the proximal portion toward distal part of the proximal portion. In an example, a proximal portion of a mesh can be inverted (e.g. folded in on itself) by moving (e.g. pulling or pushing) the middle location of the mesh and the proximal end of the mesh closer together by rotating a wire, rod, or helically-threaded member. In an example, a proximal portion of a mesh can be inverted (e.g. folded in on itself) by rotating a wire, rod, or helically-threaded member. In an example, a proximal portion of a mesh can be inverted (e.g. folded in on itself) into a bowl (e.g. hemispherical) shape by inserting microsponges or beads into the distal portion of the mesh. In an example, an operator of the device can collapse the proximal portion of a mesh by pulling a catheter which is attached to a middle location of the mesh.

In an example, an operator of the device can collapse the proximal portion of the mesh by pumping embolic liquid into the distal portion of the mesh. In an example, an operator of the device can collapse the proximal portion of the mesh by applying electrical energy to part of the perimeter (e.g. a circumferential ring) of the proximal portion, wherein this electrical energy melts (or otherwise weakens) that part of the perimeter.

In an example, an operator of the device can invert (fold in on itself) the proximal portion of a mesh by rotating a helically-threaded rod (or other threaded-member) which is attached to a middle location of the mesh. In an example, an operator of the device can invert (fold in on itself) the proximal portion of the mesh by inserting coils into the distal portion of the mesh. In an example, a circumferential portion (e.g. ring) of the proximal portion can be weakened and/or partially-melted by application of electrical energy so that the proximal portion folds, bends, and/or inverts along this ring to create a bowl shape. In an example, a proximal portion of a mesh can be collapsed by inserting embolic members and/or material into the distal portion of the mesh, wherein accumulation of the embolic members and/or material in the distal portion of the mesh exerts pressure on the proximal portion which collapses the proximal portion.

In an example, a proximal portion of a mesh can be collapsed by inserting congealing liquid embolic material into the distal portion of the mesh, wherein accumulation of the congealing liquid embolic material in the distal portion of the mesh exerts pressure on the proximal portion which collapses the proximal portion. In an example, a proximal portion of a mesh can be collapsed by moving (e.g. pulling or pushing) the distal part of the proximal portion toward the proximal part of the proximal portion. In an example, a proximal portion of a mesh can be collapsed by moving (e.g. pulling or pushing) the proximal end of the mesh toward middle location of the mesh.

In an example, a proximal portion of a mesh can be collapsed by moving the distal part of the proximal portion and the proximal part of the proximal portion closer together by pulling a wire, string, or rod. In an example, a proximal portion of a mesh can be collapsed by pulling or pushing a wire, string, or rod. In an example, a proximal portion of a mesh can be collapsed into a bowl (e.g. hemispherical) shape by inserting embolic coils into the distal portion of the mesh. In an example, a proximal portion of a mesh can be inverted (e.g. folded in on itself) by inserting embolic members and/or material into the distal portion of the mesh.

In an example, a proximal portion of a mesh can be inverted (e.g. folded in on itself) by inserting congealing liquid embolic material into the distal portion of the mesh. In an example, a proximal portion of a mesh can be inverted (e.g. folded in on itself) by moving (e.g. pulling or pushing) the middle location of the mesh toward the proximal end of the mesh.

In an example, a proximal portion of a mesh can be inverted (e.g. folded in on itself) by moving (e.g. pulling or pushing) the distal part of the proximal portion and the proximal part of the proximal portion closer together. In an example, a proximal portion of a mesh can be inverted (e.g. folded in on itself) by moving the middle location of the mesh and the proximal end of the mesh closer together by pulling or pushing a wire, string, or rod. In an example, a proximal portion of a mesh can be inverted (e.g. folded in on itself) by moving (e.g. pulling or pushing) the distal part of the proximal portion and the proximal part of the proximal portion closer together by rotating a wire, rod, or helically-threaded member.

In an example, a proximal portion of a mesh can be inverted (e.g. folded in on itself) into a bowl (e.g. hemispherical) shape by inserting congealing liquid embolic material into the distal portion of the mesh. In an example, a proximal portion of a mesh can be inverted (e.g. folded in on itself) into a bowl (e.g. hemispherical) shape by inserting "string-of-pearls" longitudinal embolic strands into the distal portion of the mesh. In an example, an operator of the device can collapse the proximal portion of a mesh by rotating a helically-threaded rod (or other threaded-member) which is attached to a middle location of the mesh.

In an example, an operator of the device can collapse the proximal portion of the mesh by inserting coils into the distal portion of the mesh. In an example, an operator of the device can invert (fold in on itself) the proximal portion of a mesh by pulling a wire or string which is attached to a middle location of the mesh. In an example, an operator of the device can invert (fold in on itself) the proximal portion of a mesh by rotating a helically-threaded rod (or other threaded-member) which is attached to a middle location of the mesh and threaded through the proximal end of the mesh, wherein rotation of the rod pulls the middle toward the proximal end.

In an example, an operator of the device can invert (fold in on itself) the proximal portion of the mesh by inserting embolic material into the distal portion of the mesh. In an example, a cross-sectional circumferential portion (e.g. ring) of the proximal portion can be weaker and/or more flexible than the rest of the proximal portion so that the proximal portion folds, bends, and/or inverts along this ring to create a bowl shape when longitudinal pressure is applied to the proximal portion. In an example, a proximal portion of a mesh can be collapsed by inserting embolic members and/or material into the distal portion of the mesh, wherein accumulation of the embolic members and/or material in the distal portion of the mesh collapses the proximal portion by exerting pressure on the proximal portion.

In an example, a proximal portion of a mesh can be collapsed by inserting congealing liquid embolic material into the distal portion of the mesh, wherein accumulation of the congealing liquid embolic material in the distal portion of the mesh collapses the proximal portion by exerting pressure on the proximal portion. In an example, a proximal portion of a mesh can be collapsed by moving (e.g. pulling or pushing) the middle location of the mesh and the proximal end of the mesh closer together. In an example, a proximal portion of a mesh can be collapsed by moving (e.g. pulling or pushing) the proximal part of the proximal portion toward distal part of the proximal portion.

In an example, a proximal portion of a mesh can be collapsed by moving (e.g. pulling or pushing) the middle location of the mesh and the proximal end of the mesh closer together by rotating a wire, rod, or helically-threaded member. In an example, a proximal portion of a mesh can be collapsed by rotating a wire, rod, or helically-threaded member. In an example, a proximal portion of a mesh can be collapsed into a bowl (e.g. hemispherical) shape by inserting microsponges or beads into the distal portion of the mesh.

In an example, a proximal portion of a mesh can be inverted (e.g. folded in on itself) by inserting embolic members and/or material into the distal portion of the mesh, wherein accumulation of the embolic members and/or material in the distal portion of the mesh exerts pressure on the proximal portion which inverts the proximal portion. In an example, a proximal portion of a mesh can be inverted (e.g. folded in on itself) by inserting congealing liquid embolic material into the distal portion of the mesh, wherein accumulation of the congealing liquid embolic material in the distal portion of the mesh exerts pressure on the proximal portion which inverts the proximal portion.

In an example, a proximal portion of a mesh can be inverted (e.g. folded in on itself) by moving (e.g. pulling or pushing) the distal part of the proximal portion toward the proximal part of the proximal portion. In an example, a proximal portion of a mesh can be inverted (e.g. folded in on itself) by moving (e.g. pulling or pushing) the proximal end of the mesh toward middle location of the mesh. In an example, a proximal portion of a mesh can be inverted (e.g. folded in on itself) by moving the distal part of the proximal portion and the proximal part of the proximal portion closer together by pulling a wire, string, or rod. In an example, a proximal portion of a mesh can be inverted (e.g. folded in on itself) by pulling or pushing a wire, string, or rod.

In an example, a proximal portion of a mesh can be inverted (e.g. folded in on itself) into a bowl (e.g. hemispherical) shape by inserting embolic coils into the distal portion of the mesh. In an example, an operator of the device can collapse the proximal portion of a mesh by pulling a wire or string which is attached to a middle location of the mesh. In an example, an operator of the device can collapse the proximal portion of a mesh by rotating a helically-threaded rod (or other threaded-member) which is attached to a middle location of the mesh and threaded through the proximal end of the mesh, wherein rotation of the rod pulls the middle toward the proximal end.

In an example, an operator of the device can collapse the proximal portion of the mesh by inserting embolic material into the distal portion of the mesh. In an example, an operator of the device can invert (fold in on itself) the proximal portion of a mesh by pulling a catheter which is attached to a middle location of the mesh. In an example, an operator of the device can invert (fold in on itself) the proximal portion of the mesh by pumping embolic liquid into the distal portion of the mesh. In an example, an operator of the device can invert (fold in on itself) the proximal portion of the mesh by applying electrical energy to part of the perimeter (e.g. a circumferential ring) of the proximal portion, wherein this electrical energy melts (or otherwise weakens) that part of the perimeter.

In an example, a method for treating a cerebral aneurysm can comprise delivering a mesh device through a catheter to a cerebral aneurysm. In an example, a method for treating a cerebral aneurysm can comprise delivering a mesh device through a catheter for insertion into the sac of a cerebral aneurysm. In an example, a mesh device can be radially-compressed and longitudinally-expanded for insertion during delivery through a catheter for insertion into a cerebral aneurysm and then radially-expanded and longitudinally-contracted after insertion into the cerebral aneurysm.

In an example, a mesh device can be temporarily radially-compressed for insertion into a catheter and delivery through the catheter to the sac of a cerebral aneurysm. In an example, portions of a mesh device which have not yet been radially-constrained by annular members can be temporarily radially-compressed for insertion into a catheter and delivery through the catheter to the sac of a cerebral aneurysm. In an example, portions of a mesh device which have not yet been radially-constrained by annular members can be temporarily radially-compressed and longitudinally-expanded for insertion into a catheter and delivery through the catheter to the sac of a cerebral aneurysm.

In an example, the same catheter can be used to deliver a mesh device into an aneurysm sac and to deliver embolic members and/or material into a distal portion of the mesh device. In an example, the catheter can be detached and removed from a person's body after embolic members and/or material has been inserted into the distal portion of the device. In an example, the device can further comprise a push wire which pushes the mesh through a catheter into an aneurysm sac.

In an example, a method for treating a cerebral aneurysm can comprise inserting a mesh into the sac of the aneurysm, wherein the distal end of the mesh is closer to the dome of the aneurysm sac than the proximal end of the mesh, and wherein the proximal end of the mesh is closer to the neck of the aneurysm than the distal end of the mesh. In an example, the diameter of the proximal portion of a mesh can be at least 10% larger than the diameter of the aneurysm neck. In an example, the diameter of the proximal portion of a mesh can be at least 40% larger than the diameter of the aneurysm neck.

In an example, the distal end of a device exits the end of catheter into the aneurysm sac before the proximal end of the device. In an example, the distal end of a mesh is not in contact with wall of the aneurysm sac before the distal portion is expanded by being filled with embolic members and/or material, but is in contact with the wall after the distal portion has been expanded by being filled with embolic members and/or material. In an example, the distal portion of a mesh exits the end of catheter into the aneurysm sac before the proximal portion of the mesh. In an example, the proximal portion of a mesh can be held against the inner surface of the aneurysm neck by pressure from the distal portion after the distal portion has been expanded.

In an example, the proximal portion of a mesh can span between 25% and 50% of the height of an aneurysm sac and the distal portion of the mesh can span the remaining height of the aneurysm sac after the proximal portion has been compressed and the distal portion has been expanded, wherein the height of an aneurysm sac is the distance between the virtual plane which best fits the aneurysm neck and the wall of the aneurysm sac which is farthest from that virtual plane. In an example, the diameter of the proximal portion of a mesh can be at least 25% larger than the diameter of the aneurysm neck. In an example, the diameter of the proximal portion of a mesh is larger than the diameter of the aneurysm neck. In an example, the distal end of a mesh exits the end of catheter into the aneurysm sac before the proximal end of the mesh.

In an example, the distal part of the distal portion of a mesh can be in contact with the most distal part of the aneurysm sac after the distal portion has been expanded by being filled with embolic members and/or material. In an example, the distal portion of the mesh of a mesh can: have a generally-globular and radially-symmetric shape before it is expanded by being filled with embolic members and/or material; and have an irregular and radially-asymmetric shape (conforming to the wall contours of an irregularly-shaped aneurysm sac) after it is expanded by being filled with embolic members and/or material.

In an example, the proximal portion of a mesh can span between 20% and 40% of the height of an aneurysm sac and the distal portion of the mesh can span the remaining height of the aneurysm sac after the proximal portion has been compressed and the distal portion has been expanded, wherein the height of an aneurysm sac is the distance between the virtual plane which best fits the aneurysm neck and the wall of the aneurysm sac which is farthest from that virtual plane. In an example, when the distal portion of a mesh is expanded by being filled with embolic members and/or material: the proximal surface of the distal portion exerts pressure on the proximal portion which holds the proximal portion in place over the aneurysm neck; and the distal surface of the distal portion conforms to the wall contours of even an irregularly-shaped aneurysm sac.

In an example, a method for treating a cerebral aneurysm can comprise expanding the distal portion of a mesh by inserting embolic members and/or embolic material into the distal portion of the mesh. In an example, a selected length of a "string-of-pearl" embolic longitudinal strand or some other strand of embolic material can be automatically inserted into a distal portion of a mesh, wherein the length is selected based on prior analysis of (3D) imaging of the aneurysm and estimation of the aneurysm sac size and/or volume.

In an example, a selected length of a "string-of-pearl" embolic longitudinal strand or some other strand of embolic material can be automatically inserted into a distal portion of a mesh and then detached, wherein the length is selected based on prior analysis of (3D) imaging of the aneurysm and estimation of the aneurysm sac size and/or volume. In an example, a selected length of a "string-of-pearl" embolic longitudinal strand or some other strand of embolic material can be automatically inserted into a distal portion of a mesh, cut, and then detached, wherein the length is selected based on prior analysis of (3D) imaging of the aneurysm and estimation of the aneurysm sac size and/or volume.

In an example, a selected length of a "string-of-pearl" embolic longitudinal strand or some other strand of embolic material can be automatically inserted into a distal portion of a mesh, wherein the length is selected based on prior analysis of (3D) imaging of the aneurysm and estimation of the aneurysm sac size and/or volume, and wherein the strand is automatically cut and detached after the selected length has been inserted. In an example, a selected number of embolic members can be automatically inserted into a distal portion of a mesh, wherein the number of embolic members is selected based on prior analysis of (3D) imaging of the aneurysm and estimation of the aneurysm sac size and/or volume.

In an example, a selected quantity of embolic material can be automatically inserted into a distal portion of a mesh, wherein the quantity is selected based on prior analysis of (3D) imaging of the aneurysm and estimation of the aneurysm sac size and/or volume. In an example, a selected volume of embolic material can be automatically inserted into a distal portion of a mesh, wherein the volume is selected based on prior analysis of (3D) imaging of the aneurysm and estimation of the aneurysm sac volume and/or size.

In an example, embolic members and/or material can be automatically inserted into a distal portion of a mesh until a selected percentage and/or fraction of the aneurysm sac is filled based on analysis of prior (3D) imaging of the aneurysm sac. In an example, embolic members and/or material can be automatically inserted into a distal portion of a mesh until a selected pressure level is reached, wherein the pressure level is measured by a pressure sensor which is part of the device.

In an example, embolic members and/or material can be automatically inserted into a distal portion of a mesh until the aneurysm sac is filled as indicated by (3D) imaging of the aneurysm sac. In an example, embolic members and/or material can be inserted into the distal portion of a mesh through a lumen (opening, hole, ring, tube, or catheter) in the proximal part of the distal portion. In an example, embolic members and/or material can be inserted into the distal portion of a mesh through a lumen (opening, hole, ring, tube, or catheter) in the center of the proximal part of the distal portion.

In an example, embolic members and/or material can be inserted into the distal portion of a mesh through a ring, band, tube, or catheter through the middle section of the mesh, wherein the middle section separates the distal portion of the mesh from the proximal portion of the mesh. In an example, embolic members and/or material can be inserted into the distal portion of a mesh through a central lumen, hole, and/or opening in a ring, band, cylinder, tube, or catheter inside a middle section of a tubular mesh, wherein the middle section separates the distal portion of the mesh from the proximal portion of the mesh.

In an example, a "string-of-pearls" embolic longitudinal strands can comprise embolic components (e.g. balls, beads, polyhedrons) which are connected to each other by flexible longitudinal components (e.g. wires, strings, threads, sutures, strands, or coils), wherein lengths of the longitudinal components increase along the strand as one moves in a proximal-to-distal direction. In an example, a "string-of-pearls" embolic longitudinal strands can comprise embolic components (e.g. balls, beads, polyhedrons) which are connected to each other by flexible longitudinal components (e.g. wires, strings, threads, sutures, strands, or coils), wherein pairs of embolic components are connected by two longitudinal components.

In an example, a central opening (e.g. opening, lumen, or channel) can be maintained inside a tubular mesh for insertion of embolic members and/or material through the opening, even after the mesh has been radially-constrained. In an example, a circumferential ring around the longitudinal midpoint of a proximal portion of a mesh can be weaker, thinner, more elastic, and/or more flexible than the rest of the proximal portion so that the proximal portion can be more easily compressed from a globular shape to a bowl shape. In an example, a device can comprise a hyperboloid-shaped mesh before it is radially-constrained and/or inverted to form proximal and distal portions.

In an example, a device can further comprise a catheter (e.g. catheter or tube) which extends through the proximal portion of a mesh into the distal portion of the mesh, wherein embolic members and/or material is inserted through the catheter into the distal portion of the mesh. In an example, a device can further comprise a catheter (e.g. catheter or tube) which is removably attached to a middle location of the mesh, wherein embolic members and/or material is inserted through the catheter into the distal portion of the mesh.

In an example, a device can further comprise a pressure sensor which measures intrasacular pressure as embolic members and/or material accumulates in the distal portion of the device. In an example, a device can further comprise a rotating threaded mechanism (e.g. an Archimedes screw) which moves embolic members and/or material out of a catheter into a distal portion of a mesh. In an example, a device can further comprise a wire, string, or thread which is attached to the middle of the mesh, wherein the wire, string, or thread is pulled to (longitudinally) compress the proximal portion of a mesh. In an example, a device further comprises a cutting mechanism with one inch of the end of a catheter which cuts off sections of longitudinal embolic members, wherein the strands are inserted into a distal portion of the device.

In an example, a device further comprises a laser with one inch of the end of a catheter which cuts off sections of "string-of-pearls" embolic longitudinal strands, wherein the strands are inserted into a distal portion of the device. In an example, a device further comprises a laser with one inch of the end of a catheter which cuts off sections of polymer embolic strands, wherein the strands are inserted into a distal portion of the device. In an example, a device further comprises a sliding or rotating blade with one inch of the end of a catheter which cuts off sections of polymer coils, wherein the strands are inserted into a distal portion of the device. In an example, a device further comprises an electrical energy emitter with one inch of the end of a catheter which melts and detaches sections of embolic coils, wherein the strands are inserted into a distal portion of the device.

In an example, a distal portion of a mesh can be between 10% and 25% larger than the proximal portion of the mesh. In an example, a distal portion of a mesh can be more concave than a proximal portion of the mesh. In an example, a distal portion of a mesh can be more undulating than a proximal portion of the mesh. In an example, a distal portion of a mesh can be the same size as the proximal portion of the mesh. In an example, a distal portion of a mesh can have a cross-sectional width (e.g. cross-sectional diameter) which is between 40% and 60% of the pre-constrained length of the mesh after the mesh has been radially-constrained in a middle location and after the distal portion has been inverted or everted.

In an example, a distal portion of a mesh can have a cross-sectional width (e.g. cross-sectional diameter) which is between 50% and 75% of the pre-constrained length of the mesh after the mesh has been radially-constrained in a middle location and after the distal portion has been inverted or everted. In an example, a distal portion of a mesh can have a shape formed by inverting the most distal part of a sphere or spheroid along the longitudinal axis of a mesh. In an example, a distal portion of a mesh can have a shape which is a proximal-to-distal reflection, flip, and/or mirror-image of the shape of a proximal portion of the mesh. In an example, a distal portion of a mesh can have a shape which is a revolution (in 3D space) of a sinusoidal wave after the mesh has been radially-constrained in a middle location and at its distal end.

In an example, a mesh (to be radially-constrained to make this device) can have a pre-constrained length (along its longitudinal axis) and tapered pre-constrained widths (across cross-sections which are orthogonal to the longitudinal axis), wherein the minimum pre-constrained width is between 40% and 60% of the length. In an example, a mesh can be a honeycomb-shaped mesh (e.g. having hexagonal openings, holes, or pores). In an example, a mesh can be made by braiding or weaving wires or tubes.

In an example, a mesh can be made from strands or yarns. In an example, a mesh can be radially-constrained and inverted at its proximal end by an first annular member, radially-constrained and inverted at its distal end by a second annular member, and radially-constrained at a middle location between its proximal end and its distal end by a third annular member. In an example, a mesh can be radially-constrained at a location on its longitudinal axis by an outer annular member (e.g. cylinder, ring, or band) and an inner annular member (e.g. cylinder, ring, or band), wherein the mesh passes between the annular member and the inner annular member, and wherein the width of the outer annular member is 10% to 30% greater than the width of the inner annular member.

In an example, a mesh can be radially-constrained at a location on its longitudinal axis by an outer cylinder which goes around the outer surface of the mesh, wherein there is also an inner cylinder which is inside the mesh at that location to maintain a lumen (e.g. opening or hole) through which embolic members and/or material can be inserted (e.g. into the distal portion of the mesh). In an example, a mesh can be radially-constrained at a location on its longitudinal axis by an outer ring which goes around the outer surface of the mesh, wherein there is also an inner ring which is inside the mesh at that location to maintain a lumen (e.g. opening) through which embolic members and/or material can be inserted (e.g. into the distal portion of the mesh).

In an example, a mesh can be radially-constrained at a location on its longitudinal axis by an outer band which goes around the outer surface of the mesh, wherein there is an inner band which is inside the mesh at that location to maintain a lumen (e.g. opening) through which embolic members and/or material can be inserted (e.g. into the distal portion of the mesh). In an example, a mesh can be radially-constrained at one or more longitudinal locations by one or more bands. In an example, a mesh can be tapered, wherein the distal end is narrower than the proximal end.

In an example, a mesh can comprise a honeycomb weave of braid of wires, tubes, or strands (wherein there are hexagonal openings, holes, or pores between the wires, tubes, or strands. In an example, a mesh can have a dumbbell shape after the mesh has been radially-constrained, but before the proximal portion of the mesh has been compressed. In an example, a mesh can have an hourglass shape after the mesh has been radially-constrained, but before the proximal portion of the mesh has been compressed. In an example, a middle location of a mesh (wherein this mesh is radially-constrained at this middle location) can be midway between 60% and 80% of the way (in a proximal-to-distal direction) between the proximal end of the mesh and the distal end of the mesh.

In an example, a proximal portion of a mesh (after the mesh has been radially-constrained in a middle location, but before the proximal portion has been inverted or everted) can have a cross-sectional width (e.g. cross-sectional diameter) which is between 20% and 45% of the pre-constrained length of the mesh. In an example, a proximal portion of a mesh (after the mesh has been radially-constrained in a middle location and after the proximal portion has been inverted or everted) can have a cross-sectional width (e.g. cross-sectional diameter) which is between 50% and 75% of the pre-constrained length of the mesh.

In an example, a proximal portion of a mesh can be (longitudinally) compressed from a globular shape to a bowl shape when an operator pulls on a wire, string, or thread. In an example, a proximal portion of a mesh can be (longitudinally) compressed from a globular shape to a bowl shape by pressure from the accumulation of embolic members and/or material in the distal portion of the mesh. In an example, a proximal portion of a mesh can be between 20% and 45% larger than the distal portion of the mesh.

In an example, a proximal portion of a mesh can be compressed before the device is inserted into a catheter for delivery to an aneurysm sac. In an example, a proximal portion of a mesh can be compressed when a device operator rotates a (threaded) catheter or tube which is connected to the distal part of the proximal portion. In an example, a proximal portion of a mesh can be larger than the distal portion of the mesh. In an example, a proximal portion of a mesh can be more longitudinally-compressed than a distal portion of the mesh. In an example, a proximal portion of a mesh can be radially symmetric. In an example, a proximal portion of a mesh can have a globular, spherical, oblate spherical, and/or ellipsoidal shape after the mesh has been radially-constrained in a middle location. In an example, a proximal portion of a mesh can have a shape formed by inverting the most distal part of a sphere along the longitudinal axis of a mesh.

In an example, a proximal portion of a mesh can have a shape which is a revolution (in 3D space) of a sinusoidal wave after the mesh has been radially-constrained in a middle location. In an example, a proximal portion of a mesh is inverted, but the distal portion of the mesh is not inverted. In an example, accumulation of embolic members and/or material in a distal portion of the mesh causes the distal portion to push against the distal surface of the proximal portion of the mesh, thereby compressing the proximal portion.

In an example, an annular member which radially-constrains a longitudinal location on a mesh can have a length (parallel to the longitudinal axis of the mesh) which is less than 10% of the pre-constrained length of the mesh. In an example, embolic members and/or material inserted into the distal portion of a device comprise hydrogel pieces. In an example, embolic members and/or material inserted into the distal portion of a device comprise microsponges, balls, or beads. In an example, insertion of members and/or material into the distal portion of the mesh can be automatically stopped when intrasacular pressure monitored by a pressure sensor reaches a selected level.

In an example, the accumulation of hydrogel(s) inserted into a distal portion of the mesh causes the distal portion to push against the distal surface of the proximal portion of the mesh, thereby compressing the proximal portion from a globular (e.g. spherical) shape into a bowl (e.g. hemispherical) shape. In an example, the diameter of a distal portion of a mesh can be between 20% and 45% greater than the diameter of the proximal portion of the mesh. In an example, the diameter of a proximal portion of a mesh can be between 20% and 45% greater than the diameter of the distal portion of the mesh. In an example, the embolic members and/or material can be compressible, soft, compliant, and/or have low durometer levels. In an example, the length of a distal portion of a mesh can be at least 50% greater than the length of the proximal portion of the mesh.

In an example, the length of a proximal portion of a mesh can be between 20% and 45% greater than the length of the distal portion of the mesh. In an example, the proximal portion of a mesh can be tapered in a first direction, the distal portion of the mesh can be tapered in a second, and the second direction can be opposite the first direction. In an example, the proximal portion of a mesh can have a first durometer level, the distal portion of the mesh can have a second durometer level, and the second level can be less than the first level. In an example, the proximal portion of a mesh can have a first length, the distal portion of the mesh can have a second length, and the second length can be greater than the first length.

In an example, the proximal portion of a mesh can have a first maximum width, the distal portion of the mesh can have a second maximum width, and the second maximum width can be less than the first maximum width. In an example, the proximal portion of a mesh can have a first number of layers, the distal portion of the mesh can have a second number of layers, and the second number can be less than the first number. In an example, the proximal portion of a mesh can have a first strength level, the distal portion of the mesh can have a second strength level, and the second level can be less than the first level. In an example, the proximal portion of the device can have a bowl shape, the distal portion of the device can have a ball shape, and the ball-shaped distal portion can be nested in the concavity of the bowl-shaped proximal portion after the proximal portion has been collapsed.

In an example, the proximal portion of the device can have a substantially-hemispherical shape (e.g. bowl shape), the distal portion of the device can have a substantially-spherical shape (e.g. spherical, oblate spherical, or ellipsoidal shape), and the substantially-spherical distal portion can be nested in the concavity of the substantially-hemispherical proximal portion after the proximal portion has been collapsed. In an example, the quantity of embolic members and/or material which is inserted into the distal portion of the mesh can be based on the volume of the aneurysm sac which, in turn, is estimated by 3D imaging. In an example, the sizes of connected embolic components in a "string-of-pearls" longitudinal embolic strand can decrease in a proximal-to-distal direction along the strand.

In an example, the width of a distal portion of a mesh can be greater than the width of a proximal portion of the mesh. In an example, the width of a proximal portion of a mesh can be greater than the width of a distal portion of the mesh. In an example, there can be a middle annular member (e.g. ring, band, or cylinder) with a first inner diameter inside a mesh at a middle location on the longitudinal axis of the mesh and a proximal annular member (e.g. ring, band, or cylinder) with a second inner diameter inside the mesh at the proximal end of the mesh, wherein the middle annular member and the proximal annular member connect (e.g. snap, fit, hook) to each other when the proximal portion of the mesh is compressed.

In an example, there can be non-uniform distances (e.g. gaps) between the between the distal surface of the proximal portion of a device and the proximal surface of the distal portion of the device after the proximal portion has been collapsed, wherein these distances (e.g. gaps) decrease as a function of distance from the proximal end of the device. In an example, a "string-of-pearls" embolic longitudinal strand can comprise embolic components (e.g. balls, beads, polyhedrons) which are connected to each other by spans of flexible wires, strings, threads, sutures, strands, or coils, wherein the (average) lengths of the spans are at least twice the (average) widths of the embolic components.

In an example, a "string-of-pearls" embolic longitudinal strands can comprise embolic components (e.g. balls, beads, polyhedrons) which are connected to each other by flexible longitudinal components (e.g. wires, strings, threads, sutures, strands, or coils), wherein lengths of the longitudinal components decrease along the strand as one moves in a proximal-to-distal direction. In an example, a "string-of-pearls" embolic longitudinal strand can comprise embolic components (e.g. balls, beads, polyhedrons) which are connected to each other by spans of flexible wires, strings, threads, sutures, strands, or coils, wherein the (average) lengths of the spans are at least three times the (average) widths of the embolic components.

In an example, a "string-of-pearls" embolic longitudinal strands can comprise embolic components (e.g. balls, beads, polyhedrons) which are connected to each other by flexible longitudinal components (e.g. wires, strings, threads, sutures, strands, or coils), wherein the durometer levels of the embolic components increase along the strand as one moves in a proximal-to-distal direction. In an example, a "string-of-pearls" embolic longitudinal strands can comprise embolic components (e.g. balls, beads, polyhedrons) which are connected to each other by flexible longitudinal components (e.g. wires, strings, threads, sutures, strands, or coils), wherein the durometer levels of the embolic components decrease along the strand as one moves in a proximal-to-distal direction.

In an example, a "string-of-pearls" embolic longitudinal strands can comprise embolic components (e.g. balls, beads, polyhedrons) which are connected to each other by flexible longitudinal components (e.g. wires, strings, threads, sutures, strands, or coils), the embolic components are radially-asymmetric around the longitudinal components. In an example, a central opening (e.g. opening, lumen, or channel) can be maintained inside a tubular mesh for insertion of embolic members and/or material into the distal portion of the mesh, even after the mesh has been radially-constrained. In an example, a cylindrical opening (e.g. opening, lumen, or channel) can be maintained inside a tubular mesh for insertion of embolic members and/or material through the opening into the distal portion of the mesh, even after the mesh has been radially-constrained.

In an example, a device can comprise a tapered tubular mesh before it is radially-constrained and/or inverted to form proximal and distal portions. In an example, a device can further comprise a catheter (e.g. catheter or tube) which extends through the proximal portion of a mesh into the distal portion of the mesh, wherein embolic members and/or material is inserted through the catheter into the distal portion of the mesh, and wherein the catheter can be detached and removed after embolic members and/or material has been inserted into the distal portion of the mesh.

In an example, a device can further comprise a conveyor belt mechanism which moves embolic members and/or material out of a catheter into a distal portion of a mesh. In an example, a device can further comprise a pressure sensor which measures intrasacular pressure as embolic members and/or material accumulates in the distal portion of the device to avoid overfilling and/or undue pressure on the aneurysm sac walls. In an example, a device can further comprise a threaded member which is attached to the middle of the mesh, wherein rotation of the threaded member pulls the middle of the mesh toward the proximal end of the mesh, thereby compressing the proximal portion of the mesh.

In an example, a device can further comprise one or more rotating gears which move embolic members and/or material out of a catheter into a distal portion of a mesh. In an example, a device further comprises a cutting mechanism with one inch of the end of a catheter which cuts off sections of embolic coils, wherein the strands are inserted into a distal portion of the device. In an example, a device further comprises a laser with one inch of the end of a catheter which cuts off sections of longitudinal embolic members, wherein the strands are inserted into a distal portion of the device. In an example, a device further comprises a sliding or rotating blade with one inch of the end of a catheter which cuts off sections of "string-of-pearls" embolic longitudinal strands, wherein the strands are inserted into a distal portion of the device.

In an example, a device further comprises a sliding or rotating blade with one inch of the end of a catheter which cuts off sections of polymer embolic strands, wherein the strands are inserted into a distal portion of the device. In an example, a device further comprises an electrical energy emitter with one inch of the end of a catheter which melts and detaches sections of polymer coils, wherein the strands are inserted into a distal portion of the device. In an example, a distal portion of a mesh can be between 20% and 45% larger than the proximal portion of the mesh. In an example, a distal portion of a mesh can be more convex than a proximal portion of the mesh. In an example, a distal portion of a mesh can be radially asymmetric. In an example, a distal portion of a mesh can be thicker than a proximal portion of the mesh.

In an example, a distal portion of a mesh can have a cross-sectional width (e.g. cross-sectional diameter) which is between 20% and 45% of the pre-constrained length of the mesh after the mesh has been radially-constrained in a middle location, but before the distal portion has been inverted or everted. In an example, a distal portion of a mesh can have a globular, spherical, oblate spherical, and/or ellipsoidal shape after the mesh has been radially-constrained in a middle location and at its distal end. In an example, a distal portion of a mesh can have a shape formed by everting the most distal part of a sphere or spheroid along the longitudinal axis of a mesh.

In an example, a distal portion of a mesh can have a shape which is symmetric to the shape of a proximal portion of the mesh with respect to a virtual plane which is orthogonal to the longitudinal axis of the mesh. In an example, a distal portion of a mesh can have a shape which is closer to being spherical than the shape of a proximal portion of the mesh. In an example, a mesh (to be radially-constrained to make this device) can have a pre-constrained length (along its longitudinal axis) and tapered pre-constrained widths (across cross-sections which are orthogonal to the longitudinal axis), wherein the minimum pre-constrained width is between 20% and 45% of the length.

In an example, a mesh can be made by 3D printing. In an example, a mesh can be made by cutting holes in a balloon. In an example, a mesh can be made from wires or tubes. In an example, a mesh can be radially-constrained at a location on its longitudinal axis by two coaxial cylinders, wherein the mesh is (pinched, crimped, threaded, or adhered) between the two coaxial cylinders. In an example, a mesh can be radially-constrained at a location on its longitudinal axis by an outer annular member (e.g. cylinder, ring, or band) and an inner annular member (e.g. cylinder, ring, or band), wherein the mesh passes between the annular member and the inner annular member, and wherein the width of the outer annular member is 20% to 50% greater than the width of the inner annular member.

In an example, a mesh can be radially-constrained at a location on its longitudinal axis by two coaxial rings, wherein the mesh is (pinched, crimped, threaded, or adhered) between the two coaxial rings. In an example, a mesh can be radially-constrained at a location on its longitudinal axis by two coaxial bands, wherein the mesh is (pinched, crimped, threaded, or adhered) between the two coaxial bands. In an example, a mesh can be radially-constrained at its proximal end by an first annular member, radially-constrained at its distal end by a second annular member, and radially-constrained at a middle location between its proximal end and its distal end by a third annular member.

In an example, a mesh can be radially-constrained at one or more longitudinal locations by one or more toroidal members. In an example, a mesh can be tapered, wherein the proximal end is narrower than the distal end. In an example, a mesh can comprise an orthogonal weave of braid of wires, tubes, or strands (wherein the wires, tubes, or strands intersect each other at right angles). In an example, a mesh can have a figure eight shape after the mesh has been radially-constrained, but before the proximal portion of the mesh has been compressed.

In an example, a middle location of a mesh (wherein this mesh is radially-constrained at this middle location) can be midway between the proximal end of the mesh and the distal end of the mesh. In an example, a proximal portion of a device can have a bowl (e.g. hemispherical) shape, an outer layer of a distal portion of the device can have a globular (e.g. spheroidal) shape, and an inner layer of the distal portion can have a funnel (e.g. partial hyperbolic) shape. In an example, a proximal portion of a mesh (after the mesh has been radially-constrained in a middle location, but before the proximal portion has been inverted or everted) can have a cross-sectional width (e.g. cross-sectional diameter) which is between 50% and 75% of the pre-constrained length of the mesh.

In an example, a proximal portion of a mesh can be (longitudinally) compressed when an operator pulls on a wire, string, or thread. In an example, a proximal portion of a mesh can be (longitudinally) compressed from a globular shape to a bowl shape when an operator pulls on a wire, string, or thread which is attached to the middle portion of the mesh. In an example, a proximal portion of a mesh can be (longitudinally) compressed from a globular shape to a bowl shape by pressure from the distal portion of the mesh when embolic members and/or material are inserted into the distal portion of the mesh. In an example, a proximal portion of a mesh can be collapsed by magnetic attraction.

In an example, a proximal portion of a mesh can be compressed when a device operator pulls on a wire, string, or thread which is connected to the distal part of the proximal portion. In an example, a proximal portion of a mesh can be compressed when a device operator rotates a helical member (e.g. helical spring or helical-threaded rod) which is connected to the distal part of the proximal portion. In an example, a proximal portion of a mesh can be more arcuate than a distal portion of the mesh. In an example, a proximal portion of a mesh can be more tapered than a distal portion of the mesh. In an example, a proximal portion of a mesh can be tapered.

In an example, a proximal portion of a mesh can have a Saturn shape, wherein the circumferential rings of the Saturn shape can be melted by the application of electrical energy to more easily compress the proximal portion from a globular shape to a bowl shape. In an example, a proximal portion of a mesh can have a shape formed by everting the most distal part of a sphere along the longitudinal axis of a mesh. In an example, a proximal portion of a mesh can have a shape which is a revolution (in 3D space) of one phase of a sinusoidal wave (e.g. which is a common shape for a Christmas tree decoration) after the mesh has been radially-constrained in a middle location.

In an example, a selected circumferential ring of a proximal portion of a mesh can be weaker, thinner, and/or more flexible than the rest of the proximal portion so that the proximal portion can be more easily compressed from a globular shape to a bowl shape. In an example, accumulation of embolic members and/or material in a distal portion of the mesh causes the distal portion to push against the distal surface of the proximal portion of the mesh, thereby compressing the proximal portion into a bowl (e.g. hemispherical) shape.

In an example, an annular member which radially-constrains a longitudinal location on a mesh can have a length (parallel to the longitudinal axis of the mesh) which is between 5% and 15% of the pre-constrained length of the mesh. In an example, embolic members and/or material inserted into the distal portion of a device comprise embolic liquid or gel. In an example, embolic members and/or material inserted into the distal portion of a device comprise "string-of-pearls" embolic strands, wherein "string-of-pearls" longitudinal embolic strands are embolic balls, beads, polyhedrons, microsponges, hydrogels or other embolic components which are connected to each other by spans of flexible wires, strings, threads, sutures, strands, or coils.

In an example, the accumulation of congealing liquid or gel inserted into a distal portion of the mesh causes the distal portion to push against the distal surface of the proximal portion of the mesh, thereby compressing the proximal portion from a globular (e.g. spherical) shape into a bowl (e.g. hemispherical) shape. In an example, the accumulation of microsponges or embolic spheres inserted into a distal portion of the mesh causes the distal portion to push against the distal surface of the proximal portion of the mesh, thereby compressing the proximal portion from a globular (e.g. spherical) shape into a bowl (e.g. hemispherical) shape.

In an example, the diameter of a distal portion of a mesh can be greater than the diameter of a proximal portion of the mesh. In an example, the diameter of a proximal portion of a mesh can be greater than the diameter of a distal portion of the mesh. In an example, the embolic members and/or material can expand due to interaction with blood when inserted into the distal portion of the device. In an example, the length of a distal portion of a mesh can be between 10% and 25% greater than the length of the proximal portion of the mesh. In an example, the length of a proximal portion of a mesh can be at least 50% greater than the length of the distal portion of the mesh.

In an example, the proximal portion of a mesh can have a first average width, the distal portion of the mesh can have a second average width, and the second average width can be greater than the first average width. In an example, the proximal portion of a mesh can have a first elasticity level, the distal portion of the mesh can have a second elasticity level, and the second level can be greater than the first level. In an example, the proximal portion of a mesh can have a first level of flexibility, the distal portion of the mesh can have a second level of flexibility, and the second level can be less than the first level. In an example, the proximal portion of a mesh can have a first mesh density, the distal portion of the mesh can have a second mesh density, and the second mesh density can be greater than the first mesh density.

In an example, the proximal portion of a mesh can have a first porosity level, the distal portion of the mesh can have a second porosity level, and the second level can be greater than the first level. In an example, the proximal portion of a mesh can have mesh openings (e.g. mesh pores or holes) with a first average size, the distal portion of the mesh can have mesh openings (e.g. mesh pores or holes) with a second average size, and the second average size can be greater than the first average size.

In an example, the proximal portion of the device can have a bowl shape and the distal portion of the device can have a ball shape after the proximal portion has been collapsed, but before the distal portion has been expanded. In an example, the proximal portion of the device can have a substantially-hemispherical shape (e.g. bowl shape), the distal portion of the device can have a substantially-spherical shape (e.g. spherical, oblate spherical, or ellipsoidal shape), and the substantially-spherical distal portion can be nested in the concavity of the substantially-hemispherical proximal portion after the proximal portion has been collapsed, but before the distal portion has been expanded.

In an example, the quantity of embolic members and/or material which is inserted into the distal portion of the mesh can be based on intrasacular pressure which is monitored by a pressure sensor within the aneurysm sac. In an example, the width of a distal portion of a mesh can be at least 50% greater than the width of the proximal portion of the mesh. In an example, the width of a proximal portion of a mesh can be at least 50% greater than the width of the distal portion of the mesh. In an example, there can be a middle annular member (e.g. ring, band, or cylinder) inside a mesh at a middle location on the longitudinal axis of the mesh and a proximal annular member (e.g. ring, band, or cylinder) inside the mesh at the proximal end of the mesh, wherein the middle annular member and the proximal annular member move toward each other when the proximal portion of the mesh is compressed.

In an example, there can be a middle annular member (e.g. ring, band, or cylinder) inside a mesh at a middle location on the longitudinal axis of the mesh and a proximal annular member (e.g. ring, band, or cylinder) inside the mesh at the proximal end of the mesh, wherein the middle annular member and the proximal annular member become nested when the proximal portion of the mesh is compressed. In an example, there can be non-uniform distances (e.g. gaps) between the between the distal surface of the proximal portion of a device and the proximal surface of the distal portion of the device after the proximal portion has been collapsed, wherein these distances (e.g. gaps) increase and then decrease as function of distance from the proximal end of the device.

In an example, a "string-of-pearls" embolic longitudinal strand can comprise embolic components (e.g. balls, beads, polyhedrons) which are connected to each other by spans of flexible wires, strings, threads, sutures, strands, or coils, wherein the centers of the embolic components are connected by the wires, strings, threads, sutures, strands, or coils. In an example, a "string-of-pearls" embolic longitudinal strands can comprise embolic components (e.g. balls, beads, polyhedrons) which are connected to each other by flexible longitudinal components (e.g. wires, strings, threads, sutures, strands, or coils), wherein the sizes of the embolic components increase along the strand as one moves in a proximal-to-distal direction. In an example, a "string-of-pearls" embolic longitudinal strands can comprise embolic components (e.g. balls, beads, polyhedrons) which are connected to each other by flexible longitudinal components (e.g. wires, strings, threads, sutures, strands, or coils), wherein the sizes of the embolic components decrease along the strand as one moves in a proximal-to-distal direction.

In an example, a central opening (e.g. opening, lumen, or channel) between the proximal and distal portions of a tubular mesh can be maintained inside the mesh even after the mesh has been radially-constrained, wherein embolic members and/or material is inserted through this opening from the proximal portion into the distal portion of the mesh. In an example, a central opening (e.g. opening, lumen, or channel) can be maintained by an annular, toroidal, and/or cylindrical member inside a tubular mesh so that embolic members and/or material can be inserted through that opening into the distal portion of the mesh after the mesh has been radially-constrained.

In an example, a device can comprise a dumbbell-shaped mesh before it is radially-constrained and/or inverted to form proximal and distal portions. In an example, a device can comprise a tubular mesh before it is radially-constrained and/or inverted to form proximal and distal portions. In an example, a device can further comprise a catheter (e.g. catheter or tube) which extends distally through the middle location of the mesh, wherein embolic members and/or material is inserted through the catheter into the distal portion of the mesh. In an example, a device can further comprise a fluid flow mechanism (e.g. a stream of pumped liquid) which moves embolic members and/or material out of a catheter into a distal portion of a mesh. In an example, a device can further comprise a pressure sensor.

In an example, a device can further comprise a threaded member which is attached to the middle of the mesh, wherein rotation of the threaded member pulls the middle of the mesh toward the proximal end of the mesh, thereby compressing the proximal portion of the mesh from a globular shape to a bowl shape. In an example, a device can have three layers, an outer layer with a bowl (e.g. hemispherical) shape, a middle layer with a globular (e.g. spherical) shape, and an inner layer with a funnel (e.g. partial hyperbolic) shape. In an example, a device further comprises a cutting mechanism with one inch of the end of a catheter which cuts off sections of polymer coils, wherein the strands are inserted into a distal portion of the device.

In an example, a device further comprises a laser with one inch of the end of a catheter which cuts off sections of embolic coils, wherein the strands are inserted into a distal portion of the device. In an example, a device further comprises a sliding or rotating blade with one inch of the end of a catheter which cuts off sections of longitudinal embolic members, wherein the strands are inserted into a distal portion of the device. In an example, a device further comprises an electrical energy emitter with one inch of the end of a catheter which melts and detaches sections of "string-of-pearls" embolic longitudinal strands, wherein the strands are inserted into a distal portion of the device.

In an example, a device further comprises an electrical energy emitter with one inch of the end of a catheter which melts and detaches sections of polymer embolic strands, wherein the strands are inserted into a distal portion of the device. In an example, a distal portion of a mesh can be larger than the proximal portion of the mesh. In an example, a distal portion of a mesh can be more longitudinally-compressed than a proximal portion of the mesh. In an example, a distal portion of a mesh can be radially symmetric. In an example, a distal portion of a mesh can have a barrel, apple, or cardioid shape after the mesh has been radially-constrained in a middle location and at its distal end.

In an example, a distal portion of a mesh can have a cross-sectional width (e.g. cross-sectional diameter) which is between 20% and 45% of the pre-constrained length of the mesh after the mesh has been radially-constrained in a middle location and after the distal portion has been inverted or everted. In an example, a distal portion of a mesh can have a shape formed by inverting a portion of a sphere or spheroid along the longitudinal axis of a mesh. In an example, a distal portion of a mesh can have a shape formed by inverting the most proximal part of a sphere or spheroid along the longitudinal axis of a mesh. In an example, a distal portion of a mesh can have a shape which is a revolution (in 3D space) of one phase of a sinusoidal wave after the mesh has been radially-constrained in a middle location and at its distal end. In an example, a distal portion of a mesh is inverted and the proximal portion of the mesh is not everted.

In an example, a mesh (to be radially-constrained to make this device) can have a pre-constrained length (along its longitudinal axis) and tapered pre-constrained widths (across cross-sections which are orthogonal to the longitudinal axis), wherein the maximum pre-constrained width is between 40% and 60% of the length. In an example, a mesh can be made by braiding or weaving metal wires (or tubes) and polymer strands (or yarns). In an example, a mesh can be made by laser cutting holes in a balloon. In an example, a mesh can be radially-constrained and everted at its proximal end by an first annular member, radially-constrained and everted at its distal end by a second annular member, and radially-constrained at a middle location between its proximal end and its distal end by a third annular member.

In an example, a mesh can be radially-constrained at a location on its longitudinal axis by an outer cylinder and an inner cylinder, wherein the mesh is (pinched, crimped, threaded, or adhered) between the outer cylinder and the inner cylinder. In an example, a mesh can be radially-constrained at a location on its longitudinal axis by an outer annular member (e.g. cylinder, ring, or band) and an inner annular member (e.g. cylinder, ring, or band), wherein the mesh passes between the annular member and the inner annular member, and wherein the width of the outer annular member is more than 50% greater than the width of the inner annular member.

In an example, a mesh can be radially-constrained at a location on its longitudinal axis by an outer ring and an inner ring, wherein the mesh is (pinched, crimped, threaded, or adhered) between the outer ring and the inner ring. In an example, a mesh can be radially-constrained at a location on its longitudinal axis by an outer band and an inner band, wherein the mesh is (pinched, crimped, threaded, or adhered) between the outer band and the inner band. In an example, a mesh can be radially-constrained at one or more longitudinal locations by one or more annular members. In an example, a mesh can be tapered, wherein the cross-sectional width of the mesh increases with distance from its proximal end.

In an example, a mesh can be woven or braided from strands or yarns. In an example, a mesh can comprise an orthogonal weave of braid of longitudinal wires, tubes, or strands and circular wires, tubes, or strands (wherein the wires, tubes, or strands intersect each other at right angles). In an example, a mesh can have a funnel shape after the mesh has been radially-constrained, but before the proximal portion of the mesh has been compressed. In an example, a middle location of a mesh (wherein this mesh is radially-constrained at this middle location) can be midway between 40% and 60% of the way (in a proximal-to-distal direction) between the proximal end of the mesh and the distal end of the mesh.

In an example, a proximal portion of a device can have a bowl (e.g. hemispherical) shape and a distal portion of a device can have a cardioid shape (e.g. a globular outer layer and a funnel-shaped inner layer). In an example, a proximal portion of a mesh (after the mesh has been radially-constrained in a middle location and after the proximal portion has been inverted or everted) can have a cross-sectional width (e.g. cross-sectional diameter) which is between 40% and 60% of the pre-constrained length of the mesh. In an example, a proximal portion of a mesh can be (longitudinally) compressed when an operator pulls on a wire, string, or thread which is attached to the middle portion of the mesh.

In an example, a proximal portion of a mesh can be (longitudinally) compressed from a globular shape to a bowl shape when an operator pulls on a wire, string, or thread which is attached to an annular member which radially-constrains a middle portion of the mesh. In an example, a proximal portion of a mesh can be at least 50% larger than the distal portion of the mesh. In an example, a proximal portion of a mesh can be collapsed by magnetic attraction between a first annular member which radially-constrains a proximal end of the mesh and a second annular member which radially constrains the middle of the mesh.

In an example, a proximal portion of a mesh can be compressed when a device operator pulls on a catheter or tube which is connected to the distal part of the proximal portion. In an example, a proximal portion of a mesh can be compressed when a device operator injects embolic members and/or material into the distal portion of the mesh. In an example, a proximal portion of a mesh can be more concave than a distal portion of the mesh. In an example, a proximal portion of a mesh can be more undulating than a distal portion of the mesh.

In an example, a proximal portion of a mesh can be thicker than a distal portion of the mesh. In an example, a proximal portion of a mesh can have a shape formed by inverting a portion of a sphere along the longitudinal axis of a mesh. In an example, a proximal portion of a mesh can have a shape formed by inverting the most proximal part of a sphere along the longitudinal axis of a mesh. In an example, a proximal portion of a mesh can have a shape which is closer to being spherical than the shape of a distal portion of the mesh. In an example, a tubular mesh (to be radially-constrained to make this device) can have a pre-constrained length (along its longitudinal axis) and a uniform pre-constrained width (across cross-sections which are orthogonal to the longitudinal axis), wherein this uniform width is between 40% and 60% of the length.

In an example, accumulation of embolic members and/or material in a distal portion of the mesh causes the distal portion to push against the distal surface of the proximal portion of the mesh, thereby compressing the proximal portion from a globular (e.g. spherical) shape into a bowl (e.g. hemispherical) shape. In an example, an oblate spheroid shape can be formed by compressing a sphere along an axis which is parallel to the longitudinal axis of a mesh. In an example, embolic members and/or material inserted into the distal portion of a device comprise congealing liquid or gel. In an example, embolic members and/or material inserted into the distal portion of a device comprise "string-of-pearls" embolic strands, wherein "string-of-pearls" longitudinal embolic strands are embolic balls, beads, polyhedrons, microsponges, hydrogels or other embolic components which are connected to each other by spans of flexible wires, strings, threads, sutures, strands, or coils.

In an example, the accumulation of embolic coils inserted into a distal portion of the mesh causes the distal portion to push against the distal surface of the proximal portion of the mesh, thereby compressing the proximal portion from a globular (e.g. spherical) shape into a bowl (e.g. hemispherical) shape. In an example, the diameter of a distal portion of a mesh can be at least 50% greater than the diameter of the proximal portion of the mesh. In an example, the diameter of a proximal portion of a mesh can be at least 50% greater than the diameter of the distal portion of the mesh. In an example, the distances between connected embolic components in a "string-of-pearls" longitudinal embolic strand can increase in a proximal-to-distal direction along the strand. In an example, the embolic members and/or material can expand when inserted into the distal portion of the device.

In an example, the length of a distal portion of a mesh can be between 20% and 45% greater than the length of the proximal portion of the mesh. In an example, the proximal portion of a mesh can be made with wires, tubes, or strands having a first average width, the distal portion of the mesh can be made with wires, tubes, or strands having a second average width, and the second average width can be greater than the first average width. In an example, the proximal portion of a mesh can have a first average width, the distal portion of the mesh can have a second average width, and the second average width can be less than the first average width.

In an example, the proximal portion of a mesh can have a first elasticity level, the distal portion of the mesh can have a second elasticity level, and the second level can be less than the first level. In an example, the proximal portion of a mesh can have a first length, the distal portion of the mesh can have a second length, and the second length can be less than the first length. In an example, the proximal portion of a mesh can have a first mesh density, the distal portion of the mesh can have a second mesh density, and the second mesh density can be less than the first mesh density. In an example, the proximal portion of a mesh can have a first porosity level, the distal portion of the mesh can have a second porosity level, and the second level can be less than the first level.

In an example, the proximal portion of a mesh can have mesh openings (e.g. mesh pores or holes) with a first average size, the distal portion of the mesh can have mesh openings (e.g. mesh pores or holes) with a second average size, and the second average size can be less than the first average size. In an example, the proximal portion of the device can have a bowl shape, the distal portion of the device can have a ball shape, and the ball-shaped distal portion can be nested in the concavity of the bowl-shaped proximal portion after the proximal portion has been collapsed, but before the distal portion has been expanded. In an example, the quantity of embolic members and/or material which is inserted into the distal portion of the mesh can be based on 3D imaging of the aneurysm sac.

In an example, the shapes of connected embolic components in a "string-of-pearls" longitudinal embolic strand can vary with proximal-to-distal distance along the strand. In an example, the width of a distal portion of a mesh can be between 10% and 25% greater than the width of the proximal portion of the mesh. In an example, the width of a proximal portion of a mesh can be between 10% and 25% greater than the width of the distal portion of the mesh. In an example, there can be a middle annular member (e.g. ring, band, or cylinder) with a first inner diameter inside a mesh at a middle location on the longitudinal axis of the mesh and a proximal annular member (e.g. ring, band, or cylinder) with a second inner diameter inside the mesh at the proximal end of the mesh, wherein the middle annular member and the proximal annular member fit into each other when the proximal portion of the mesh is compressed.

In an example, there can be a uniform distance (e.g. gap) between the distal surface of the proximal portion of a device and the proximal surface of the distal portion of the device after the proximal portion has been collapsed. In an example, there can be proximal-to-distal variation in the sizes of connected embolic components in a "string-of-pearls" longitudinal embolic strand. In an example, a "string-of-pearls" embolic longitudinal strands can comprise embolic components (e.g. balls, beads, polyhedrons) which are connected to each other by flexible longitudinal components (e.g. wires, strings, threads, sutures, strands, or coils), wherein distances between embolic components increase along the strand as one moves in a proximal-to-distal direction.

In an example, a "string-of-pearls" embolic longitudinal strands can comprise embolic components (e.g. balls, beads, polyhedrons) which are connected to each other by flexible longitudinal components (e.g. wires, strings, threads, sutures, strands, or coils), wherein distances between embolic components decrease along the strand as one moves in a proximal-to-distal direction. In an example, a "string-of-pearls" embolic longitudinal strands can comprise embolic components (e.g. balls, beads, polyhedrons) which are connected to each other by flexible longitudinal components (e.g. wires, strings, threads, sutures, strands, or coils), wherein the flexible longitudinal components are helical.

In an example, a central opening (e.g. opening, lumen, or channel) between the proximal and distal portions of a tubular mesh can be maintained inside the mesh by an annular member inside the mesh even after the mesh has been radially-constrained, wherein embolic members and/or material is inserted through this opening from the proximal portion into the distal portion of the mesh. In an example, a circumferential ring around a middle section of a proximal portion of a mesh can be selectively melted by the application of electrical energy so that the proximal portion can be more easily compressed from a globular shape to a bowl shape.

In an example, a device can comprise a frustum-shaped mesh before it is radially-constrained and/or inverted to form proximal and distal portions. In an example, a device can comprise an hourglass-shaped mesh before it is radially-constrained and/or inverted to form proximal and distal portions. In an example, a device can further comprise a catheter (e.g. catheter or tube) which is attached to a middle location of the mesh, wherein embolic members and/or material is inserted through the catheter into the distal portion of the mesh. In an example, a device can further comprise a peristaltic mechanism (e.g. a peristaltic pump) which moves embolic members and/or material out of a catheter into a distal portion of a mesh.

In an example, a device can further comprise a pusher wire which moves embolic members and/or material out of a catheter into a distal portion of a mesh. In an example, a device can further comprise a wire, string, or thread which is pulled to (longitudinally) compress the proximal portion of a mesh. In an example, a device further comprises a cutting mechanism with one inch of the end of a catheter which cuts off sections of "string-of-pearls" embolic longitudinal strands, wherein the strands are inserted into a distal portion of the device.

In an example, a device further comprises a cutting mechanism with one inch of the end of a catheter which cuts off sections of polymer embolic strands, wherein the strands are inserted into a distal portion of the device. In an example, a device further comprises a laser with one inch of the end of a catheter which cuts off sections of polymer coils, wherein the strands are inserted into a distal portion of the device. In an example, a device further comprises a sliding or rotating blade with one inch of the end of a catheter which cuts off sections of embolic coils, wherein the strands are inserted into a distal portion of the device. In an example, a device further comprises an electrical energy emitter with one inch of the end of a catheter which melts and detaches sections of longitudinal embolic members, wherein the strands are inserted into a distal portion of the device.

In an example, a distal portion of a mesh can be at least 50% larger than the proximal portion of the mesh. In an example, a distal portion of a mesh can be more arcuate than a proximal portion of the mesh. In an example, a distal portion of a mesh can be more tapered than a proximal portion of the mesh. In an example, a distal portion of a mesh can be tapered. In an example, a distal portion of a mesh can have a cross-sectional width (e.g. cross-sectional diameter) which is between 40% and 60% of the pre-constrained length of the mesh after the mesh has been radially-constrained in a middle location, but before the distal portion has been inverted or everted.

In an example, a distal portion of a mesh can have a cross-sectional width (e.g. cross-sectional diameter) which is between 50% and 75% of the pre-constrained length of the mesh after the mesh has been radially-constrained in a middle location, but before the distal portion has been inverted or everted. In an example, a distal portion of a mesh can have a shape formed by everting a portion of a sphere or spheroid along the longitudinal axis of a mesh. In an example, a distal portion of a mesh can have a shape formed by everting the most proximal part of a sphere or spheroid along the longitudinal axis of a mesh. In an example, a distal portion of a mesh can have a shape which is a revolution (in 3D space) of one phase of a sinusoidal wave (e.g. a common shape for a Christmas tree decoration) after the mesh has been radially-constrained in a middle location and at its distal end.

In an example, a distal portion of a mesh is inverted, but the proximal portion of the mesh is not inverted. In an example, a mesh (to be radially-constrained to make this device) can have a pre-constrained length (along its longitudinal axis) and tapered pre-constrained widths (across cross-sections which are orthogonal to the longitudinal axis), wherein the maximum pre-constrained width is between 20% and 45% of the length. In an example, a mesh can be made by braiding or weaving strands or yarns.

In an example, a mesh can be made by laser cutting. In an example, a mesh can be radially-constrained and everted at its proximal end by an first annular member, radially-constrained and inverted at its distal end by a second annular member, and radially-constrained at a middle location between its proximal end and its distal end by a third annular member. In an example, a mesh can be radially-constrained at a location on its longitudinal axis by an outer annular member (e.g. cylinder, ring, or band) and an inner annular member (e.g. cylinder, ring, or band), wherein the mesh is (pinched, crimped, threaded, or adhered) between the outer annular member and the inner annular member.

In an example, a mesh can be radially-constrained at a location on its longitudinal axis by an outer cylinder and an inner cylinder, wherein the mesh is (pinched, crimped, threaded, or adhered) between the outer cylinder and the inner cylinder, and wherein embolic members and/or material can be inserted (e.g. into the distal portion of the mesh) through the central lumen (e.g. opening or hole) of the inner cylinder. In an example, a mesh can be radially-constrained at a location on its longitudinal axis by an outer ring and an inner ring, wherein the mesh is (pinched, crimped, threaded, or adhered) between the outer ring and the inner ring, and wherein embolic members and/or material can be inserted (e.g. into the distal portion of the mesh) through the lumen (e.g. opening) of the inner ring.

In an example, a mesh can be radially-constrained at a location on its longitudinal axis by an outer band and an inner band, wherein the mesh is (pinched, crimped, threaded, or adhered) between the outer band and the inner band, and wherein embolic members and/or material can be inserted (e.g. into the distal portion of the mesh) through the lumen (e.g. opening) of the inner band. In an example, a mesh can be radially-constrained at one or more longitudinal locations by one or more rings. In an example, a mesh can be tapered, wherein the cross-sectional width of the mesh decreases with distance from its proximal end. In an example, a mesh can be woven or braided from wires or tubes.

In an example, a mesh can have a 3D hyperbola of revolution shape after the mesh has been radially-constrained, but before the proximal portion of the mesh has been compressed. In an example, a mesh can have a hyperboloid shape after the mesh has been radially-constrained, but before the proximal portion of the mesh has been compressed. In an example, a middle location of a mesh (wherein this mesh is radially-constrained at this middle location) can be midway between 20% and 45% of the way (in a proximal-to-distal direction) between the proximal end of the mesh and the distal end of the mesh. In an example, a proximal portion of a mesh (after the mesh has been radially-constrained in a middle location, but before the proximal portion has been inverted or everted) can have a cross-sectional width (e.g. cross-sectional diameter) which is between 40% and 60% of the pre-constrained length of the mesh.

In an example, a proximal portion of a mesh (after the mesh has been radially-constrained in a middle location and after the proximal portion has been inverted or everted) can have a cross-sectional width (e.g. cross-sectional diameter) which is between 20% and 45% of the pre-constrained length of the mesh. In an example, a proximal portion of a mesh can be (longitudinally) compressed when an operator pulls on a wire, string, or thread which is attached to an annular member which radially-constrains a middle portion of the mesh.

In an example, a proximal portion of a mesh can be (longitudinally) compressed by pressure from the accumulation of embolic members and/or material in the distal portion of the mesh. In an example, a proximal portion of a mesh can be between 10% and 25% larger than the distal portion of the mesh. In an example, a proximal portion of a mesh can be compressed after the device is inserted into a catheter for delivery to an aneurysm sac; this has the advantage of spreading out the maximum radial mass of the device as it is delivered through the catheter. In an example, a proximal portion of a mesh can be compressed when a device operator rotates a (threaded) wire which is connected to the distal part of the proximal portion. In an example, a proximal portion of a mesh can be inverted and the distal portion of the mesh can be everted.

In an example, a proximal portion of a mesh can be more convex than a distal portion of the mesh. In an example, a proximal portion of a mesh can be radially asymmetric. In an example, a proximal portion of a mesh can have a barrel, apple, or cardioid shape after the mesh has been radially-constrained in a middle location. In an example, a proximal portion of a mesh can have a shape formed by everting a portion of a sphere along the longitudinal axis of a mesh. In an example, a proximal portion of a mesh can have a shape formed by everting the most proximal part of a sphere along the longitudinal axis of a mesh. In an example, a proximal portion of a mesh can have a shape which is a proximal-to-distal reflection, flip, and/or mirror-image of the shape of a distal portion of the mesh.

In an example, a tubular mesh (to be radially-constrained to make this device) can have a pre-constrained length (along its longitudinal axis) and a uniform pre-constrained width (across cross-sections which are orthogonal to the longitudinal axis), wherein this uniform width is between 20% and 45% of the length. In an example, an annular (e.g. ring) part of a proximal portion of a mesh can be weaker, thinner, and/or more flexible than the rest of the proximal portion so that the proximal portion can be more easily compressed from a globular shape to a bowl shape. In an example, an oblate spheroid shape can be formed by compressing a sphere along an axis which is orthogonal to the longitudinal axis of a mesh.

In an example, embolic members and/or material inserted into the distal portion of a device comprise embolic coils or ribbons. In an example, insertion of members and/or material into the distal portion of the mesh can be stopped when intrasacular pressure monitored by a pressure sensor reaches a selected level. In an example, the accumulation of embolic strands inserted into a distal portion of the mesh causes the distal portion to push against the distal surface of the proximal portion of the mesh, thereby compressing the proximal portion from a globular (e.g. spherical) shape into a bowl (e.g. hemispherical) shape.

In an example, the diameter of a distal portion of a mesh can be between 10% and 25% greater than the diameter of the proximal portion of the mesh. In an example, the diameter of a proximal portion of a mesh can be between 10% and 25% greater than the diameter of the distal portion of the mesh. In an example, the distances between connected embolic components in a "string-of-pearls" longitudinal embolic strand can decrease in a proximal-to-distal direction along the strand. In an example, the embolic members and/or material can self-expand due to interaction with blood when inserted into the distal portion of the device. In an example, the length of a proximal portion of a mesh can be between 10% and 25% greater than the length of the distal portion of the mesh.

In an example, the proximal portion of a mesh can be made with wires, tubes, or strands having a first average width, the distal portion of the mesh can be made with wires, tubes, or strands having a second average width, and the second average width can be less than the first average width. In an example, the proximal portion of a mesh can have a first durometer level, the distal portion of the mesh can have a second durometer level, and the second level can be greater than the first level. In an example, the proximal portion of a mesh can have a first level of flexibility, the distal portion of the mesh can have a second level of flexibility, and the second level can be greater than the first level.

In an example, the proximal portion of a mesh can have a first maximum width, the distal portion of the mesh can have a second maximum width, and the second maximum width can be greater than the first maximum width. In an example, the proximal portion of a mesh can have a first number of layers, the distal portion of the mesh can have a second number of layers, and the second number can be greater than the first number. In an example, the proximal portion of a mesh can have a first strength level, the distal portion of the mesh can have a second strength level, and the second level can be greater than the first level. In an example, the proximal portion of the device can have a bowl shape and the distal portion of the device can have a ball shape after the proximal portion has been collapsed.

In an example, the proximal portion of the device can have a bowl shape and the distal portion of the device can have a ball shape after the proximal portion has been collapsed, but before the distal portion has been expanded. In an example, the quantity of embolic members and/or material which is inserted into the distal portion of the mesh can be based on 3D imaging of the aneurysm sac prior to the device insertion procedure. In an example, the sizes of connected embolic components in a "string-of-pearls" longitudinal embolic strand can increase in a proximal-to-distal direction along the strand. In an example, the width of a distal portion of a mesh can be between 20% and 45% greater than the width of the proximal portion of the mesh.

In an example, the width of a proximal portion of a mesh can be between 20% and 45% greater than the width of the distal portion of the mesh. In an example, there can be a middle annular member (e.g. ring, band, or cylinder) inside a mesh at a middle location on the longitudinal axis of the mesh and a proximal annular member (e.g. ring, band, or cylinder) inside the mesh at the proximal end of the mesh, wherein the middle annular member and the proximal annular member connect with each other, attach to each other, link to each other, and/or fit into each other when the proximal portion of the mesh is compressed. In an example, there can be non-uniform distances (e.g. gaps) between the between the distal surface of the proximal portion of a device and the proximal surface of the distal portion of the device after the proximal portion has been collapsed, wherein these distances (e.g. gaps) increase as a function of distance from the proximal end of the device. Method and device variations discussed above can be applied to the examples shown in the following figures where relevant.

Having concluded the introductory section, FIGS. 1-13 are now discussed in detail. FIG. 1 shows an example of a method for treating a cerebral aneurysm comprising: 101 forming a longitudinal tubular mesh, wherein the mesh has a proximal end, a distal end, a longitudinal axis between the proximal end and the distal end, and radial cross-sections which are orthogonal to the longitudinal axis; 102 radially-constraining the proximal end and the distal end of the mesh; 103 dividing the mesh into a convex proximal portion of the mesh and a convex distal portion by radially-constraining a middle location on the mesh, wherein the middle location is somewhere between the proximal and distal ends; 104 collapsing the proximal portion onto itself by moving the middle location and the proximal end of the mesh closer together; 105 delivering the mesh through a catheter to a cerebral aneurysm; 106 inserting the mesh into the sac of the aneurysm, wherein the distal end of the mesh is closer to the dome of the aneurysm sac than the proximal end of the mesh, and wherein the proximal end of the mesh is closer to the neck of the aneurysm than the distal end of the mesh; and 107 expanding the distal portion by inserting embolic members and/or embolic material into the distal portion. Variations on this method discussed elsewhere in this disclosure or priority-linked disclosures can also be applied to this example where relevant.

Figure 3:
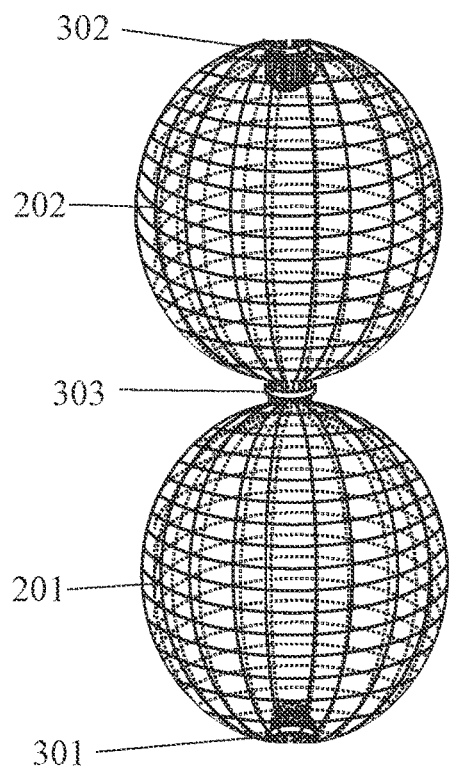
Figure 4:
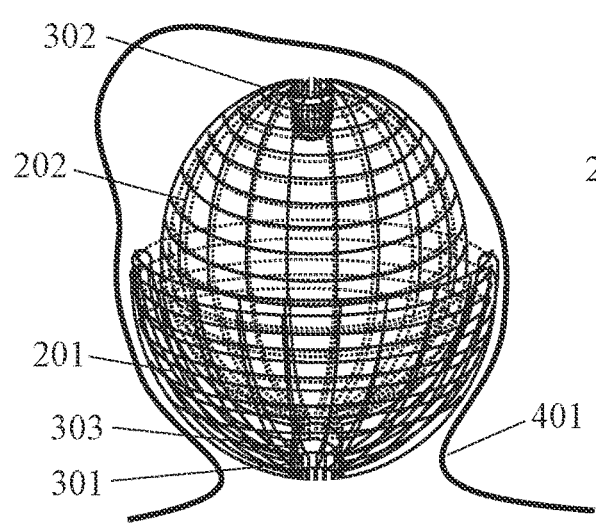
Figure 5:
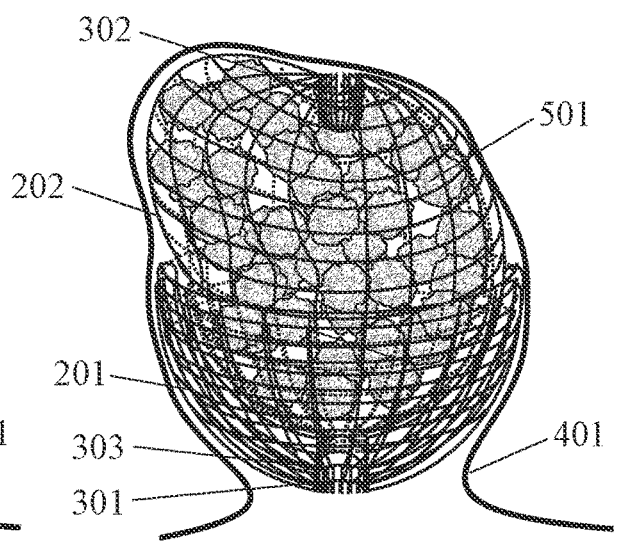

FIGS. 2-5 show four sequential views of an example of a device for treating a cerebral aneurysm. FIG. 2 shows this device at a first point in time wherein it starts out as a tubular mesh. FIG. 3 shows this device at a second point in time after the ends of the tubular mesh have been radially constrained and a middle location of the tubular mesh has also been radially constrained, thereby dividing the tubular mesh into a convex distal portion and a convex proximal portion. FIG. 4 shows this device at a third point in time after the mesh has been inserted into the sac of an irregularly-shaped cerebral aneurysm and the proximal portion of the mesh has been longitudinally collapsed onto itself into a hemispherical or bowl shape. In an example, the proximal portion can be collapsed before being inserted into the aneurysm sac. Alternatively, the proximal portion can be collapsed after being inserted into the aneurysm sac. FIG. 5 shows this device at a fourth point in time after the distal portion of the mesh has been expanded into conformity with walls of the irregularly-shaped aneurysm sac by being filled with embolic members and/or embolic material.

With respect to specific components, FIGS. 2-5 show an example of a device for treating a cerebral aneurysm comprising: a proximal portion 201 and a distal portion 202 of a longitudinal tubular mesh; a proximal annular member 301 which radially-constrains the proximal end of the mesh; a distal annular member 302 which radially-constrains the distal end of the mesh; a middle annular member 303 which radially-constrains a middle location of the mesh, wherein the middle location is somewhere between the proximal and distal ends of the mesh; and embolic members and/or embolic material 501 which is inserted into the distal portion of the mesh, wherein the mesh is configured to be inserted into an aneurysm sac 401, and wherein insertion of the embolic members and/or embolic material expands the distal portion of the mesh to conform to the walls of even an irregularly-shaped aneurysm sac. Variations on this device discussed elsewhere in this disclosure or priority-linked disclosures can also be applied to this example where relevant.

Relating FIGS. 2-5 to the method described in FIG. 1, FIG. 2 shows a device after the tubular mesh has been formed, but before it has been radially-constrained. FIG. 3 shows the device after the ends and middle of the mesh have been radially constrained, but before the proximal portion of the mesh has been collapsed. FIG. 3 shows the device after the proximal portion of the mesh has been collapsed, but before the distal portion of the mesh has been expanded by being filled with embolic members and/or embolic material. FIG. 4 shows the device after the distal portion of the mesh has expanded by being filled with embolic members and/or embolic material. Variations on this method discussed elsewhere in this disclosure or priority-linked disclosures can also be applied to this example where relevant.

FIGS. 6-9 show four sequential views of another example of a device for treating a cerebral aneurysm. This example is like the one shown in FIGS. 2-5, except that it includes a catheter which extends through the proximal portion of the mesh into the distal portion of the mesh. This catheter is used to deliver embolic members and/or material into the distal portion of the mesh. In this example, this catheter is removed after embolic members and/or material have been inserted into the distal portion of the mesh.

Figure 6:
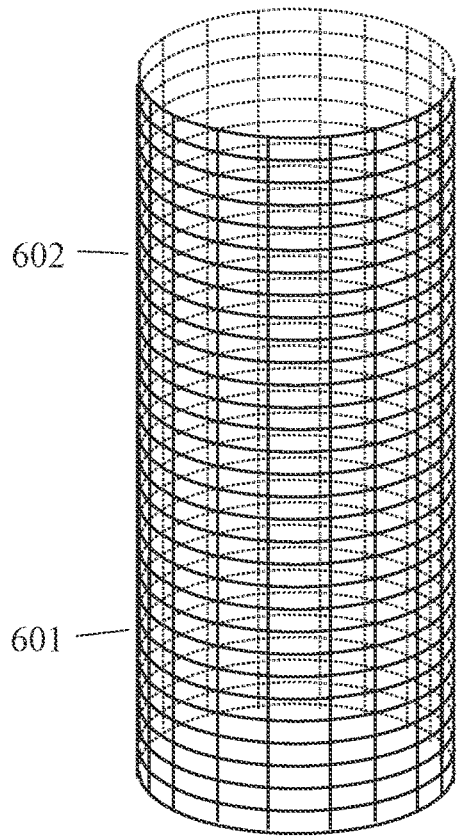
FIGS. 6-9 show four sequential views of a mesh device like the one shown in FIGS. 2-5, except that it also includes a catheter for inserting embolic members and/or material through the proximal portion of the device into the distal portion of the device.
Figure 7:
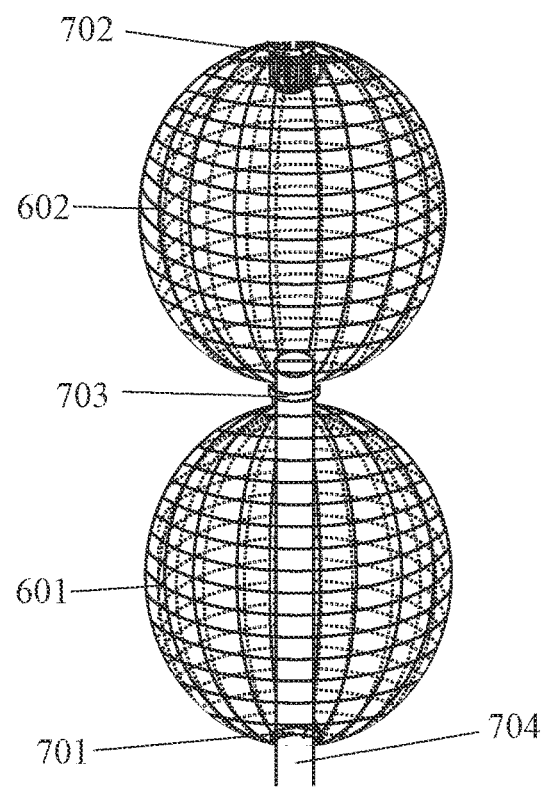
Figure 8:
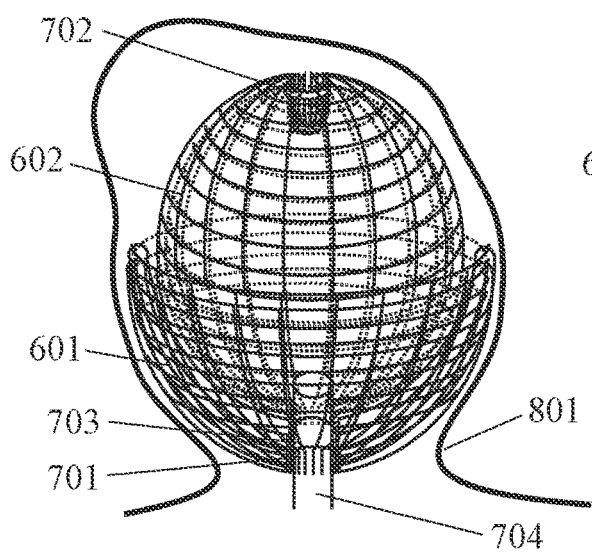
Figure 9:
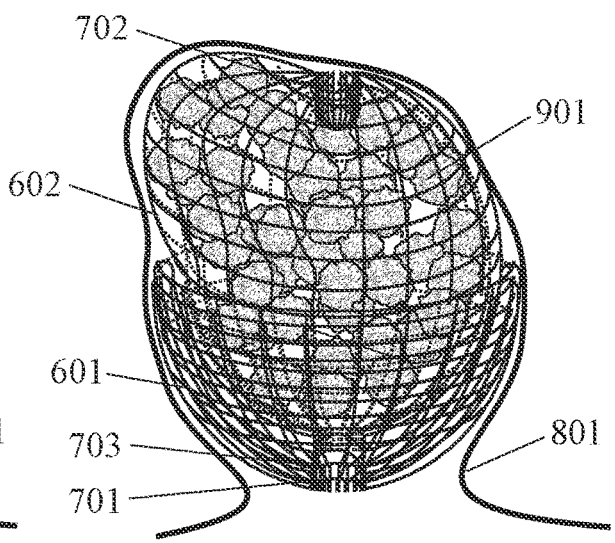

FIG. 6 shows this device at a first point in time wherein it starts out as a tubular mesh. FIG. 7 shows this device at a second point in time after the ends of the tubular mesh have been radially constrained and a middle location of the tubular mesh has also been radially constrained, thereby dividing the tubular mesh into a convex distal portion and a convex proximal portion. FIG. 8 shows this device at a third point in time after the mesh has been inserted into the sac of an irregularly-shaped cerebral aneurysm and the proximal portion of the mesh has been longitudinally collapsed onto itself into a hemispherical or bowl shape. In an example, the proximal portion can be collapsed before being inserted into the aneurysm sac. Alternatively, the proximal portion can be collapsed after being inserted into the aneurysm sac. FIG. 9 shows this device at a fourth point in time: after the distal portion of the mesh has been expanded into conformity with walls of the irregularly-shaped aneurysm sac by being filled with embolic members and/or embolic material; and after the catheter has been detached and removed.

With respect to specific components, FIGS. 6-9 show an example of a device for treating a cerebral aneurysm comprising: a proximal portion 601 and a distal portion 602 of a longitudinal tubular mesh; a proximal annular member 701 which radially-constrains the proximal end of the mesh; a distal annular member 702 which radially-constrains the distal end of the mesh; a middle annular member 703 which radially-constrains a middle location of the mesh, wherein the middle location is somewhere between the proximal and distal ends of the mesh; a catheter 704 which extends into the distal portion; and embolic members and/or embolic material 901 which is inserted into the distal portion of the mesh, wherein the mesh is configured to be inserted into an aneurysm sac 801, and wherein insertion of the embolic members and/or embolic material expands the distal portion of the mesh to conform to the walls of even an irregularly-shaped aneurysm sac. Variations on this device discussed elsewhere in this disclosure or priority-linked disclosures can also be applied to this example where relevant.

Relating FIGS. 6-9 to the method described in FIG. 1, FIG. 6 shows a device after the tubular mesh has been formed, but before it has been radially-constrained. FIG. 7 shows the device after the ends and middle of the mesh have been radially constrained, but before the proximal portion of the mesh has been collapsed. FIG. 8 shows the device after the proximal portion of the mesh has been collapsed, but before the distal portion of the mesh has been expanded by being filled with embolic members and/or embolic material. FIG. 9 shows the device after the distal portion of the mesh has expanded by being filled with embolic members and/or embolic material. Variations on this method discussed elsewhere in this disclosure or priority-linked disclosures can also be applied to this example where relevant.

Figure 10:
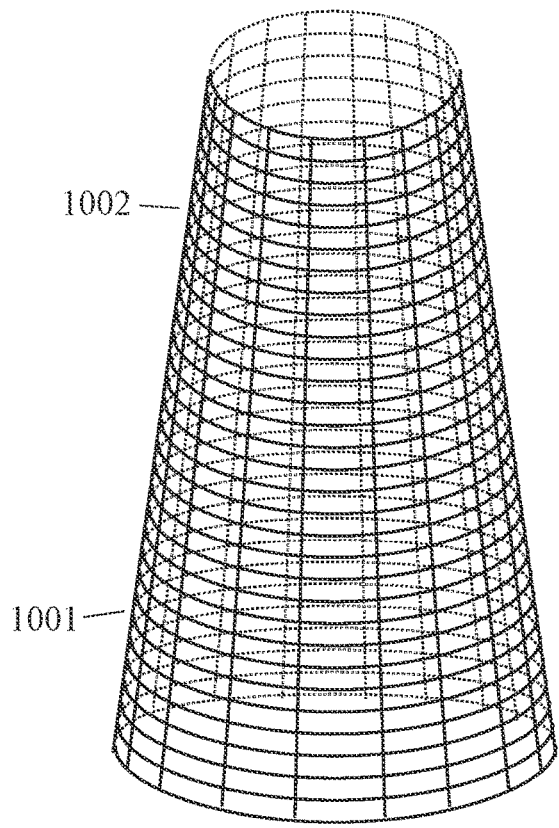
FIGS. 10-13 show four sequential views of a mesh device like the one shown in FIGS. 2-5, except that the tubular mesh from which the device is formed is tapered.
Figure 11:
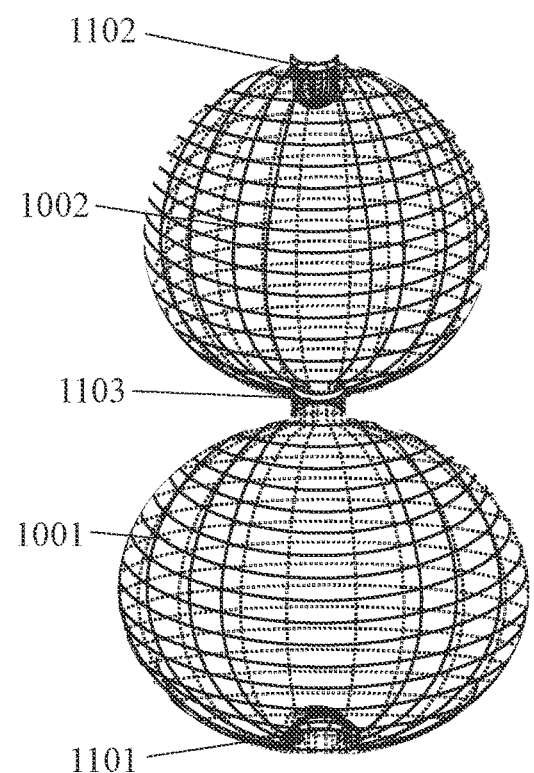
Figure 12:
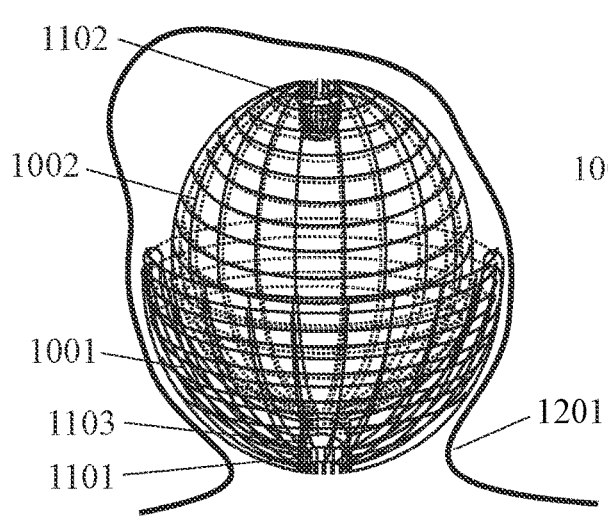
Figure 13:
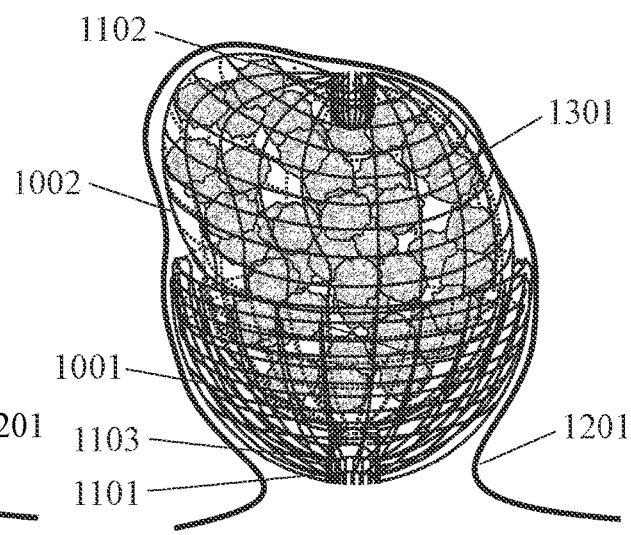

FIGS. 10-13 show four sequential views of another example of a device for treating a cerebral aneurysm. This example is like the one shown in FIGS. 2-5, except that the tubular mesh is tapered, being narrower at its distal end than at its proximal end. FIG. 10 shows this device at a first point in time wherein it starts out as a tubular mesh. FIG. 11 shows this device at a second point in time after the ends of the tubular mesh have been radially constrained and a middle location of the tubular mesh has also been radially constrained, thereby dividing the tubular mesh into a convex distal portion and a convex proximal portion. FIG. 12 shows this device at a third point in time after the mesh has been inserted into the sac of an irregularly-shaped cerebral aneurysm and the proximal portion of the mesh has been longitudinally collapsed onto itself into a hemispherical or bowl shape. In an example, the proximal portion can be collapsed before being inserted into the aneurysm sac. Alternatively, the proximal portion can be collapsed after being inserted into the aneurysm sac. FIG. 13 shows this device at a fourth point in time after the distal portion of the mesh has been expanded into conformity with walls of the irregularly-shaped aneurysm sac by being filled with embolic members and/or embolic material.

With respect to specific components, FIGS. 10-13 show an example of a device for treating a cerebral aneurysm comprising: a proximal portion 1001 and a distal portion 1002 of a tapered tubular mesh; a proximal annular member 1101 which radially-constrains the proximal end of the mesh; a distal annular member 1102 which radially-constrains the distal end of the mesh; a middle annular member 1103 which radially-constrains a middle location of the mesh, wherein the middle location is somewhere between the proximal and distal ends of the mesh; and embolic members and/or embolic material 1301 which is inserted into the distal portion of the mesh, wherein the mesh is configured to be inserted into an aneurysm sac 1201, and wherein insertion of the embolic members and/or embolic material expands the distal portion of the mesh to conform to the walls of even an irregularly-shaped aneurysm sac. Variations on this device discussed elsewhere in this disclosure or priority-linked disclosures can also be applied to this example where relevant.

Relating FIGS. 10-13 to the method described in FIG. 1, FIG. 10 shows a device after the tubular mesh has been formed, but before it has been radially-constrained. FIG. 11 shows the device after the ends and middle of the mesh have been radially constrained, but before the proximal portion of the mesh has been collapsed. FIG. 12 shows the device after the proximal portion of the mesh has been collapsed, but before the distal portion of the mesh has been expanded by being filled with embolic members and/or embolic material. FIG. 13 shows the device after the distal portion of the mesh has expanded by being filled with embolic members and/or embolic material. Variations on this method discussed elsewhere in this disclosure or priority-linked disclosures can also be applied to this example where relevant.

I claim:

1. A method for treating a cerebral aneurysm comprising:
forming a longitudinal tubular mesh, wherein the mesh has a proximal end, a distal end, a longitudinal axis between the proximal end and the distal end, and radial cross-sections which are orthogonal to the longitudinal axis;
radially-constraining the proximal end and the distal end of the mesh;
dividing the mesh into a convex proximal portion of the mesh and a convex distal portion of the mesh by radially-constraining a middle location on the mesh, wherein the middle location is somewhere between the proximal and distal ends;
collapsing the proximal portion onto itself by moving the middle location and the proximal end of the mesh closer together;
delivering the mesh through a catheter to a cerebral aneurysm;
inserting the mesh into the sac of the aneurysm, wherein the distal end of the mesh is closer to the dome of the aneurysm sac than the proximal end of the mesh, and wherein the proximal end of the mesh is closer to the neck of the aneurysm than the distal end of the mesh; and
expanding the distal portion by inserting embolic members and/or embolic material into the distal portion.

2. A method for treating a cerebral aneurysm comprising:
forming a longitudinal tubular mesh, wherein the mesh has a proximal end, a distal end, a longitudinal axis between the proximal end and the distal end, and radial cross-sections which are orthogonal to the longitudinal axis;
radially-constraining the proximal end and the distal end of the mesh;
dividing the mesh into a convex proximal portion of the mesh and a convex distal portion of the mesh by radially-constraining a middle location on the mesh, wherein the middle location is somewhere between the proximal and distal ends;
delivering the mesh through a catheter to a cerebral aneurysm; inserting the mesh into the sac of the aneurysm, wherein the distal end of the mesh is closer to the dome of the aneurysm sac than the proximal end of the mesh, and wherein the proximal end of the mesh is closer to the neck of the aneurysm than the distal end of the mesh;
collapsing the proximal portion onto itself by moving the middle location and the proximal end of the mesh closer together; and
expanding the distal portion by inserting embolic members and/or embolic material into the distal portion.

* * * * *